(12) United States Patent
Galán García et al.

(10) Patent No.: US 12,382,827 B2
(45) Date of Patent: Aug. 5, 2025

(54) COMPOUND AND AN ORGANIC SEMICONDUCTING LAYER, AN ORGANIC ELECTRONIC DEVICE, A DISPLAY DEVICE AND A LIGHTING DEVICE COMPRISING THE SAME

(71) Applicant: Novaled GmbH, Dresden (DE)

(72) Inventors: Elena Galán García, Dresden (DE); Benjamin Schulze, Dresden (DE)

(73) Assignee: Novaled GmbH, Dresden (DE)

( * ) Notice: Subject to any disclaimer, the term of this patent is extended or adjusted under 35 U.S.C. 154(b) by 722 days.

(21) Appl. No.: 17/622,730

(22) PCT Filed: Jul. 15, 2020

(86) PCT No.: PCT/EP2020/069963
§ 371 (c)(1),
(2) Date: Dec. 24, 2021

(87) PCT Pub. No.: WO2021/009206
PCT Pub. Date: Jan. 21, 2021

(65) Prior Publication Data
US 2022/0165958 A1  May 26, 2022

(30) Foreign Application Priority Data
Jul. 15, 2019 (EP) .................... 19186200

(51) Int. Cl.
*H10K 85/60* (2023.01)
*C07D 401/04* (2006.01)
(Continued)

(52) U.S. Cl.
CPC ......... *H10K 85/654* (2023.02); *C07D 401/04* (2013.01); *C07D 401/10* (2013.01);
(Continued)

(58) Field of Classification Search
CPC .. C07D 401/04; C07D 401/10; C07D 251/24; C07D 241/12; C07D 241/38;
(Continued)

(56) References Cited

U.S. PATENT DOCUMENTS 9,780,310 B2  10/2017  Oka et al.
10,529,929 B2  1/2020  Cho et al.
(Continued)

FOREIGN PATENT DOCUMENTS

CN  106892901      6/2017
CN  106892901 A *  6/2017
(Continued)

OTHER PUBLICATIONS

Oyamada et al., Chemistry Letters, 33(8), 2004, 1034-1035.*
(Continued)

*Primary Examiner* — Vu A Nguyen
(74) *Attorney, Agent, or Firm* — Eversheds Sutherland (US) LLP

(57) ABSTRACT

The present invention relates to a compound represented by the following Formula (I), a semiconducting layer comprising this compound, an organic electronic device comprising said organic semiconducting layer, as well as to a device comprising the organic electronic device.

(I)

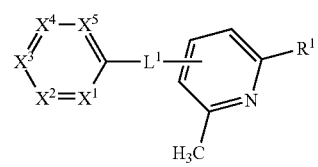

14 Claims, 2 Drawing Sheets

(51) Int. Cl.
*C07D 401/10* (2006.01)
*C07D 401/14* (2006.01)
*C09K 11/06* (2006.01)
*H10K 50/16* (2023.01)

(52) U.S. Cl.
CPC ............ *C07D 401/14* (2013.01); *C09K 11/06* (2013.01); *H10K 85/615* (2023.02); *C09K 2211/1018* (2013.01); *H10K 50/16* (2023.02)

(58) Field of Classification Search
CPC .. C07D 241/42; C07D 239/26; C07D 239/74; H10K 85/615; H10K 85/654
See application file for complete search history.

(56) References Cited

U.S. PATENT DOCUMENTS

| | | | | |
|---|---|---|---|---|
| 2013/0281693 | A1* | 10/2013 | Inoue | C09K 11/06 544/225 |
| 2017/0092880 | A1* | 3/2017 | Boudreault | H10K 85/40 |
| 2017/0186964 | A1* | 6/2017 | Cho | H10K 85/342 |
| 2017/0186975 | A1* | 6/2017 | Kim | H10K 85/324 |

FOREIGN PATENT DOCUMENTS

| | | | |
|---|---|---|---|
| EP | 3048654 | A2 | 7/2016 |
| JP | 2004284971 | | 10/2004 |
| JP | 2004284971 | A * | 10/2004 |
| JP | 2017105717 | | 6/2017 |
| KR | 20170058618 | | 5/2017 |
| KR | 20170058625 | | 5/2017 |
| KR | 20170090139 | | 8/2017 |
| WO | 2016175292 | A1 | 11/2016 |
| WO | WO-2018079211 | A1 * | 5/2018 ............. C09K 11/06 |

OTHER PUBLICATIONS

Notification of First Office Action issued in China application No. 202080048401.8, dated Sep. 23, 2023 (27 pages).
Communication pursuant to Article 94(3) EPC issued in European application No. 19186200.2, dated Oct. 31, 2023 (6 pages).
International Search Report and Written Opinion for PCT/EP2020/069963, Sep. 9, 2020.
Communication pursuant to Article 94(3) EPC issued in European application No. 20742686.7, dated Mar. 1, 2024 (6 pages).

* cited by examiner

COMPOUND AND AN ORGANIC SEMICONDUCTING LAYER, AN ORGANIC ELECTRONIC DEVICE, A DISPLAY DEVICE AND A LIGHTING DEVICE COMPRISING THE SAME

CROSS-REFERENCE TO RELATED APPLICATIONS

This application is a U.S. national phase application of PCT/EP2020/069963, filed Jul. 15, 2020, which claims priority to European Application No. 19186200.2, filed Jul. 15, 2019. The content of these applications is incorporated by reference herein.

The present invention relates to a compound as well as to an organic semiconducting layer comprising the same. The invention further relates to an organic electronic device comprising the organic semiconducting layer, respectively the compound. Furthermore, the invention is related to a display device or a lighting device comprising the organic electronic device.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer (HTL), an emission layer (EML), an electron transport layer (ETL), and a cathode, which are sequentially stacked on a substrate. In this regard, the HTL, the EML, and the ETL are thin films formed from organic and/or organometallic compounds.

When a voltage is applied to the anode and the cathode, holes injected from the anode electrode move to the EML, via the HTL, and electrons injected from the cathode electrode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency.

Compounds comprising triazine groups are known in the art and used in organic electronics applications, especially as electron transport materials.

However, there is still a need to improve the electronic properties of respective compounds for use in organic electronic devices, in particular to provide compounds having a LUMO further away from vacuum level, a higher dipole moment, improved melting point and suitable rate on-set temperature compared to compounds known in the art. Furthermore, there is still a need to provide compounds suitable to improve the performance of organic electronic devices, in particular to improve efficiency, lifetime and driving voltage thereof, at best to provide a high efficiency with improved trade of with respect to the driving voltage.

It is therefore an object of the present invention to provide novel organic electronic devices and compounds for use therein overcoming drawbacks of the prior art, in particular to provide novel compounds having improved properties, in particular melting points and/or glass transition temperatures and/or electronic properties and/or rate onset temperature which may be suitable to improve the performance of organic electronic devices, in particular when used in an electron transport layer thereof.

SUMMARY OF THE INVENTION

The above object is achieved by a compound represented by the following Formula (I)

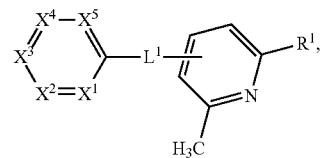

wherein $R^1$ selected from the group consisting of H, $CH_3$, ethyl, n-propyl, iso-propyl, n-butyl, sec-butyl, iso-butyl and tert-butyl;

$L^1$ represents a direct bond or is $C_6$ to $C_{18}$ arylene;

$X^1$ to $X^5$ are independently selected from the group consisting of $CR^2$ and N, wherein 2 to 4 of $X^1$ to $X^5$ are N and 1 to 3 of $X^1$ to $X^5$ are independently selected $CR^2$;

$R^2$ is independently selected from the group consisting of H, substituted or unsubstituted $C_6$ to $C_{36}$ aryl, substituted or unsubstituted $C_3$ to $C_{36}$ heteroaryl, and a group represented by the following Formula (II)

 (II), wherein the asterisk symbol "*" represents the binding position of the structure according to Formula II to the C-atom in the respective group $CR^2$;

two adjacent $R^2$ can be linked together to form a ring;

the one or more substituent(s), if present in one or more of the groups $R^2$ are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$; wherein Y is O or S, and $R^3$ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl, and $C_3$-$C_{20}$ heteroaryl;

at least one of $R^2$ is represented by the Formula (II);

in Formula (II) $L^2$ represents a direct bond or is a substituted or unsubstituted $C_6$ to $C_{24}$ arylene group or a substituted or unsubstituted $C_3$ to $C_{20}$ heteroarylene;

$Ar^1$ is selected from the group consisting of substituted or unsubstituted $C_6$ to $C_{36}$ aryl, substituted or unsubstituted $C_3$ to $C_{36}$ heteroaryl; and substituted or unsubstituted $C_2$ to $C_6$ alkenyl, wherein the one or more substituent(s), if present in $L^2$ or $Ar^1$, are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and PY $(R^3)_2$, wherein Y is O or S, and $R^3$ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl; and wherein it is provided that in case that $L^2$ represents a direct bond $Ar^1$ is not phenyl or biphenyl.

In a further embodiment compound represented by the following Formula (I)

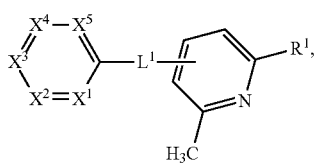

(I)

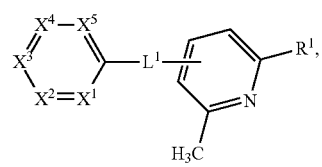

(I)

wherein $R^1$ is H;

$L^1$ represents a direct bond or is $C_6$ to $C_{18}$ arylene;

$X^1$ to $X^5$ are independently selected from the group consisting of $CR^2$ and N, wherein 2 to 4 of $X^1$ to $X^5$ are N and 1 to 3 of $X^1$ to $X^5$ are independently selected $CR^2$;

$R^2$ is independently selected from the group consisting of H, substituted or unsubstituted $C_6$ to $C_{36}$ aryl, substituted or unsubstituted $C_3$ to $C_{36}$ heteroaryl, and a group represented by the following Formula (II)

$$*-L^2-Ar^1 \qquad (II),$$

wherein the asterisk symbol "*" represents the binding position of the structure according to Formula II to the C-atom in the respective group $CR^2$;

two adjacent $R^2$ can be linked together to form a ring;

the one or more substituent(s), if present in one or more of the groups $R^2$ are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$; wherein Y is O or S, and $R^3$ are independently selected from the group consisting of $C_1$-$C_{20}$ linear alkyl, $C_1$-$C_{20}$ alkoxy, $C_3$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl, and $C_3$-$C_{20}$ heteroaryl;

at least one of $R^2$ is represented by the Formula (II);

in Formula (II) $L^2$ represents a direct bond or is a substituted or unsubstituted $C_6$ to $C_{24}$ arylene group or a substituted or unsubstituted $C_3$ to $C_{20}$ heteroarylene;

$Ar^1$ is selected from the group consisting of substituted or unsubstituted $C_6$ to $C_{36}$ aryl, substituted or unsubstituted $C_3$ to $C_{36}$ heteroaryl; and substituted or unsubstituted $C_2$ to $C_6$ alkenyl, wherein the one or more substituent(s), if present in $L^2$ or $Ar^1$, are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and PY $(R^3)_2$, wherein Y is O or S, and $R^3$ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl; and wherein it is provided that in case that $L^2$ represents a direct bond $Ar^1$ is not phenyl or biphenyl.

In a further embodiment compound represented by the following Formula (I)

wherein $R^1$ is $CH_3$, ethyl, n-propyl or iso-propyl;

$L^1$ represents a direct bond or is $C_6$ to $C_{18}$ arylene;

$X^1$ to $X^5$ are independently selected from the group consisting of $CR^2$ and N, wherein 2 to 4 of $X^1$ to $X^5$ are N and 1 to 3 of $X^1$ to $X^5$ are independently selected $CR^2$;

$R^2$ is independently selected from the group consisting of H, substituted or unsubstituted $C_6$ to $C_{36}$ aryl, substituted or unsubstituted $C_3$ to $C_{36}$ heteroaryl, and a group represented by the following Formula (II)

$$*-L^2-Ar^1 \qquad (II),$$

wherein the asterisk symbol "*" represents the binding position of the structure according to Formula II to the C-atom in the respective group $CR^2$;

two adjacent $R^2$ can be linked together to form a ring;

the one or more substituent(s), if present in one or more of the groups $R^2$ are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$; wherein Y is O or S, and $R^3$ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl, and $C_3$-$C_{20}$ heteroaryl;

at least one of $R^2$ is represented by the Formula (II);

in Formula (II) $L^2$ represents a direct bond or is a substituted or unsubstituted $C_6$ to $C_{24}$ arylene group or a substituted or unsubstituted $C_3$ to $C_{20}$ heteroarylene;

$Ar^1$ is selected from the group consisting of substituted or unsubstituted $C_6$ to $C_{36}$ aryl, substituted or unsubstituted $C_3$ to $C_{36}$ heteroaryl; and substituted or unsubstituted $C_2$ to $C_6$ alkenyl, wherein the one or more substituent(s), if present in $L^2$ or $Ar^1$, are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and PY $(R^3)_2$, wherein Y is O or S, and $R^3$ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl; and wherein it is provided that in case that $L^2$ represents a direct bond $Ar^1$ is not phenyl or biphenyl.

In a further embodiment wherein the compound of Formula (I) is represented by Formula (I-a)

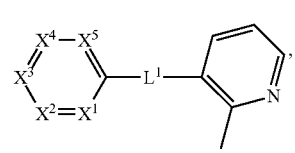

(I-a)

wherein

L¹ represents a direct bond or is $C_6$ to $C_{18}$ arylene;

$X^1$ to $X^5$ are independently selected from the group consisting of $CR^2$ and N, wherein 2 to 4 of $X^1$ to $X^5$ are N and 1 to 3 of $X^1$ to $X^5$ are independently selected $CR^2$;

$R^2$ is independently selected from the group consisting of H, substituted or unsubstituted $C_6$ to $C_{36}$ aryl, substituted or unsubstituted $C_3$ to $C_{36}$ heteroaryl, and a group represented by the following Formula (II)

$$*-L^2-Ar^1 \quad (II),$$

wherein the asterisk symbol "*" represents the binding position of the structure according to Formula II to the C-atom in the respective group $CR^2$;

two adjacent $R^2$ can be linked together to form a ring;

the one or more substituent(s), if present in one or more of the groups $R^2$ are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$; wherein Y is O or S, and $R^3$ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl, and $C_3$-$C_{20}$ heteroaryl;

at least one of $R^2$ is represented by the Formula (II);

in Formula (II) $L^2$ represents a direct bond or is a substituted or unsubstituted $C_6$ to $C_{24}$ arylene group or a substituted or unsubstituted $C_3$ to $C_{20}$ heteroarylene;

$Ar^1$ is selected from the group consisting of substituted or unsubstituted $C_6$ to $C_{36}$ aryl, substituted or unsubstituted $C_3$ to $C_{36}$ heteroaryl; and substituted or unsubstituted $C_2$ to $C_6$ alkenyl, wherein the one or more substituent(s), if present in $L^2$ or $Ar^1$, are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$, wherein Y is O or S, and $R^3$ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl; and wherein it is provided that in case that $L^2$ represents a direct bond $Ar^1$ is not phenyl or biphenyl.

In a further embodiment wherein the compound of Formula (I) is represented by Formula (I-b) or (I-c) or (I-d)

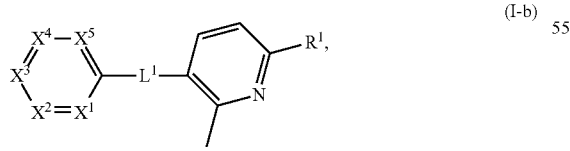

(I-b)

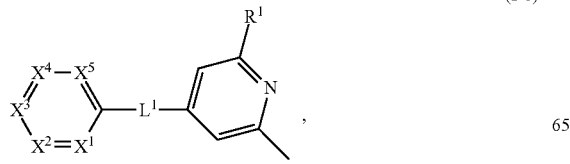

(I-c)

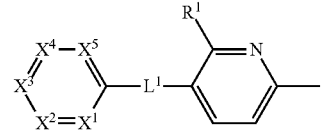

(I-d)

wherein $R^1$ is selected from the group consisting of $CH_3$, ethyl, n-propyl, iso-propyl, n-butyl, sec-butyl, iso-butyl and tert-butyl;

$L^1$ represents a direct bond or is $C_6$ to $C_{18}$ arylene;

$X^1$ to $X^5$ are independently selected from the group consisting of $CR^2$ and N, wherein 2 to 4 of $X^1$ to $X^5$ are N and 1 to 3 of $X^1$ to $X^5$ are independently selected $CR^2$;

$R^2$ is independently selected from the group consisting of H, substituted or unsubstituted $C_6$ to $C_{36}$ aryl, substituted or unsubstituted $C_3$ to $C_{36}$ heteroaryl, and a group represented by the following Formula (II)

$$*-L^2-Ar^1 \quad (II),$$

wherein the asterisk symbol "*" represents the binding position of the structure according to Formula II to the C-atom in the respective group $CR^2$;

two adjacent $R^2$ can be linked together to form a ring;

the one or more substituent(s), if present in one or more of the groups $R^2$ are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$; wherein Y is O or S, and $R^3$ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl, and $C_3$-$C_{20}$ heteroaryl;

at least one of $R^2$ is represented by the Formula (II);

in Formula (II) $L^2$ represents a direct bond or is a substituted or unsubstituted $C_6$ to $C_{24}$ arylene group or a substituted or unsubstituted $C_3$ to $C_{20}$ heteroarylene;

$Ar^1$ is selected from the group consisting of substituted or unsubstituted $C_6$ to $C_{36}$ aryl, substituted or unsubstituted $C_3$ to $C_{36}$ heteroaryl; and substituted or unsubstituted $C_2$ to $C_6$ alkenyl, wherein the one or more substituent(s), if present in $L^2$ or $Ar^1$, are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$, wherein Y is O or S, and $R^3$ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl; and wherein it is provided that in case that $L^2$ represents a direct bond $Ar^1$ is not phenyl or biphenyl.

It was surprising found by the inventors that compounds of Formula (I) above have a LUMO further away from vacuum level, a higher dipole moment and improved melting point and rate onset temperature compared to compounds known in the art. Furthermore, it was surprisingly found that organic electronic devices comprising such compounds show improved performance, in particular show improved efficiency, lifetime and driving voltage.

It was in particular found by the inventors that the compounds of Formula (I) above are suitable to improve efficiency in trade off with respect to the driving voltage of an OLED device comprising the same, in particular if the compound of Formula (I) is comprised in an electrone transport material thereof.

The term "direct bond" as used herein refers to a single bond connecting the respective moieties connected with the direct bond.

In case that two adjacent $X^1$ to $X^5$ are $CR^2$, the two adjacent $R^2$ can be linked together to form a ring. In this case, the selection of $R^2$ is not limited to the groups mentioned above. Rather, in this case, the two $R^2$ may be independently selected from alkyl, alkenyl, or, in more general, acyl. In this regard, it is preferred that the two adjacent $R^2$ form together an aromatic ring which may, in one embodiment, be a 6-membered aromatic ring. Exemplary respective embodiments are as follows.

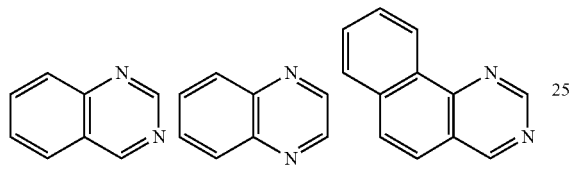

In the above exemplary embodiments, the uttermost right hand ring comprising the nitrogen atoms is the ring encompassing the moieties $X^1$ to $X^5$ of Formula (I).

An exemplary respective compounds may, therefore, be as follows

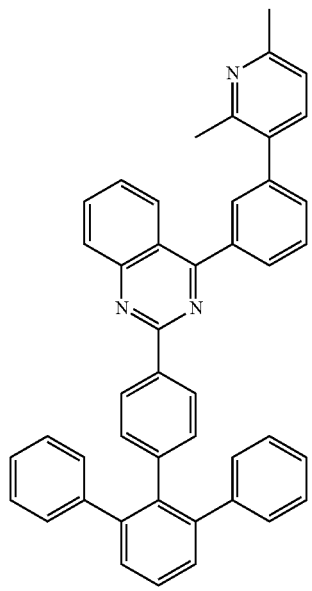

wherein it has to be understood that this is only for clarification and not limiting for the respective feature.

In accordance with the invention, it is provided that in case that $L^2$ represents a direct bond $Ar^1$ is not phenyl or biphenyl. In this regard, it may in particular be provided that the following compounds are excluded.

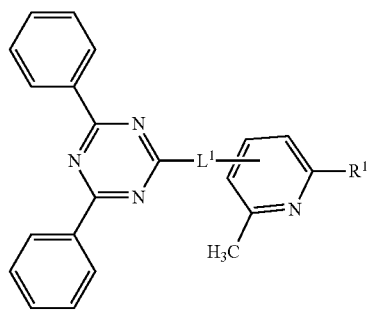

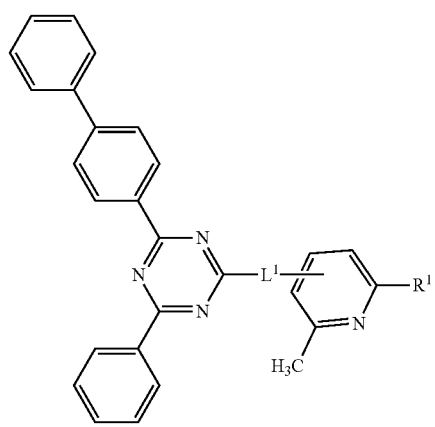

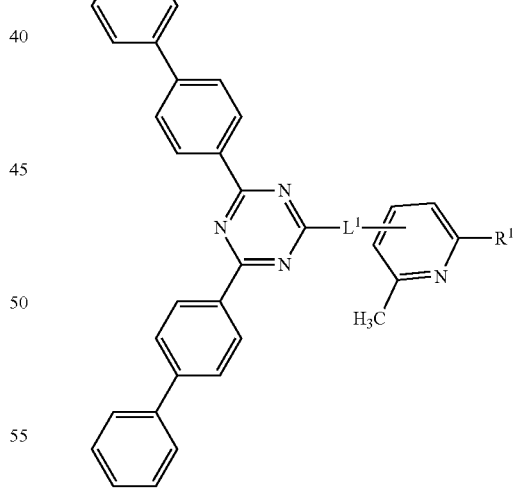

It was further surprisingly found by the inventors that certain embodiments are particularly advantageous for achieving the technical effect of improving OLED efficiency, lifetime and driving voltage. Such embodiments are described in the following. In this regard, it was found by the inventors that the properties can be further improved when combining to or more of these embodiments.

The compound of Formula (I) may be represented by one of the following formulas (III) to (IX)

(III)
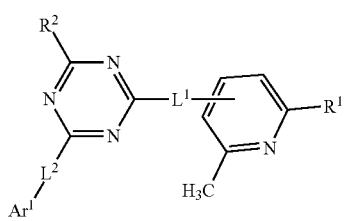

(IV)
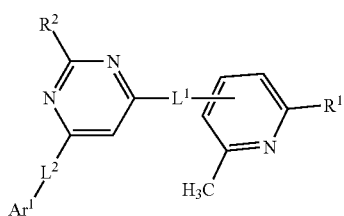

(V)
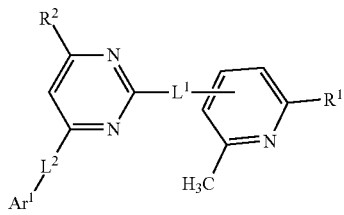

(VI)
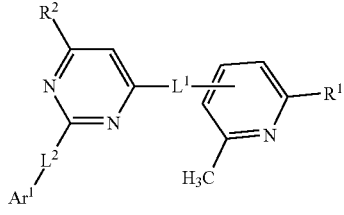

(VII)
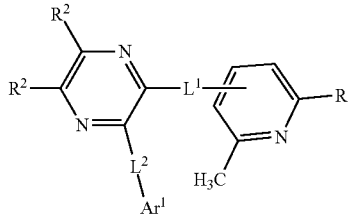

(VIII)
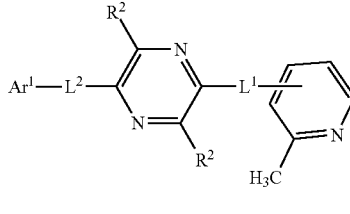

(IX)
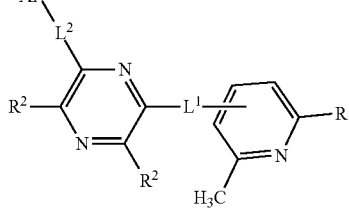

In the above Formula (I) as well as in the Formulas (III) to (VII) binding of the moiety $R^1$ to the pyridin moiety may be in each position not covered by the $CH_3$ or the $R^1$ group.

Possible binding positions are labeled in the following formula by the asterisk symbols "*"

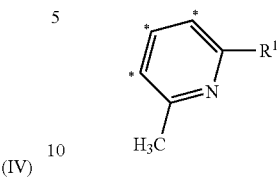

$R^1$ may be H, $CH_3$, ethyl ($C_2H_5$), propyl ($C_3H_7$), in particular n-propyl or iso-propyl.

In a further embodiment $R^1$ is H or $CH_3$, alternatively $CH_3$.

In a further embodiment $L^1$ represents a single bond or is selected from the group consisting of phenylene, biphenylene, triphenylene, and naphthylene.

$L^1$ may be a direct bond or a group selected from the following structures C1 to C20.

C1
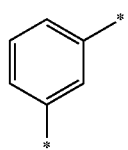

C2
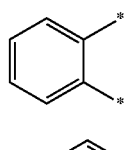

C3
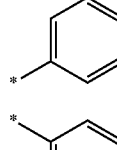

C4
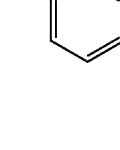

C5
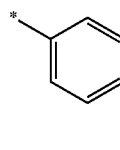

C6
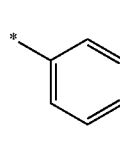

C7
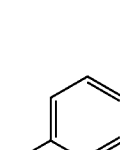

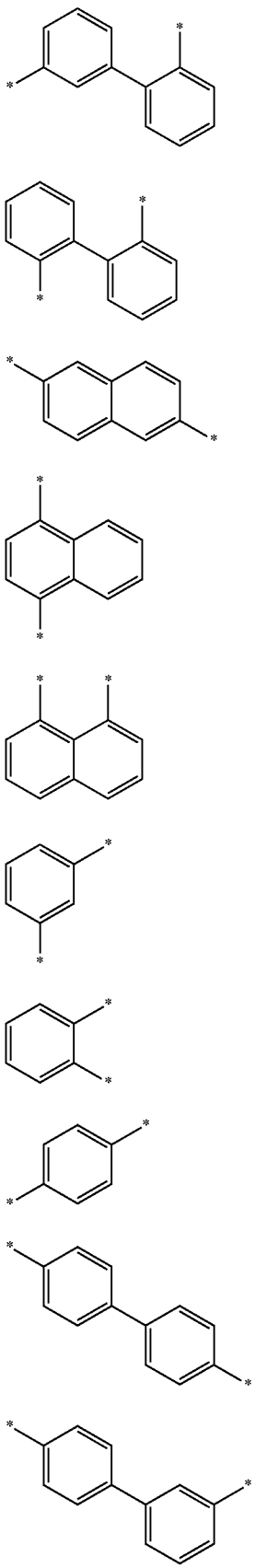

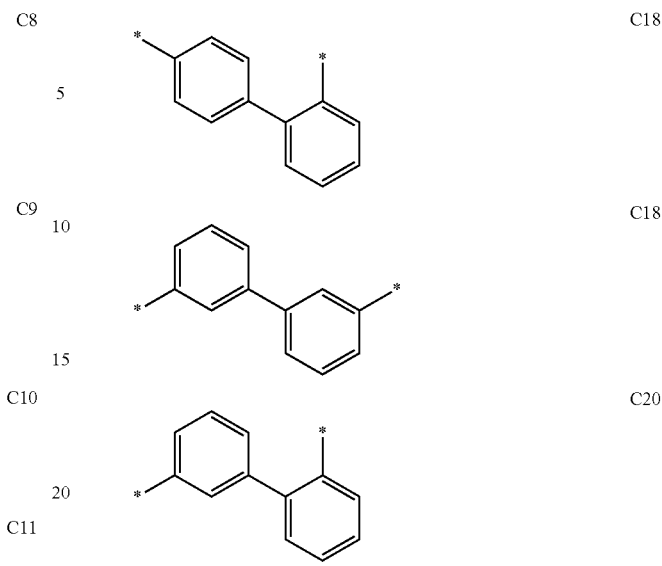

In a further embodiment L¹ represents a direct bond or is phenylene.

In one embodiment, it may be provided that or three of $X^1$ to $X^5$ are N.

In one embodiment, the six-membered ring of Formula (I) containing $X^1$ to $X^5$ is selected from the following structures.

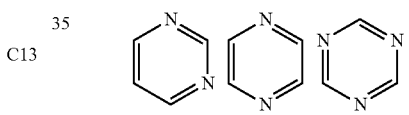

In a further embodiment $R^2$ is independently selected from the group consisting of phenyl, biphenyl, terphenyl, phenantherenyl, benzophenantherenyl, naphthyl, fluorenyl, dimethyl fluorenyl, diphenylfluorenyl, 9,9'-spirobi[fluorene], pyrenyl, crysenyl, fluoranthenyl, tetraphenylethenyl, nitrile, spiro[fluorene-9,9'-xanthene], benzothiophenyl, dibenzofuranyl, carbazolyl, benzothiphenyl, benzofuranyl, benzooxazolyl, benzothiazolyl, quinazolinyl, quinoxalinyl, and quinolinyl, and the group represented by the Formula (II)

$$*-L^2-Ar^1 \quad (II),$$

wherein the respective groups may independently be substituted or unsubstituted, wherein the one or more substituent(s), if present in one or more of the groups $R^2$, are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$, wherein Y is O or S, and $R^3$ are independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl.

$R^2$ may be independently selected from the group consisting of the following compounds D1 to D69.

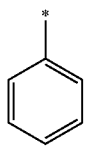
D1
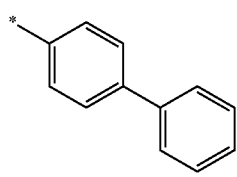
D2
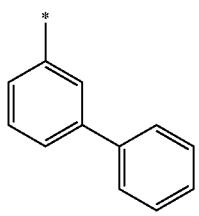
D3
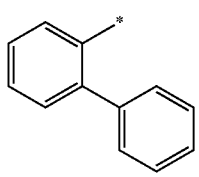
D4
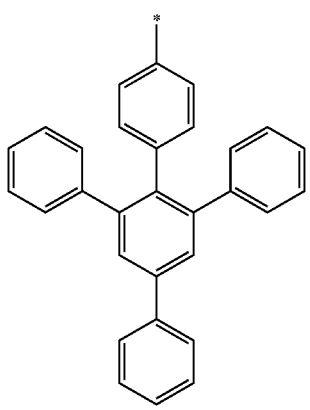
D5
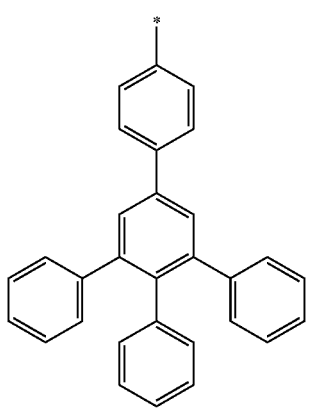
D6
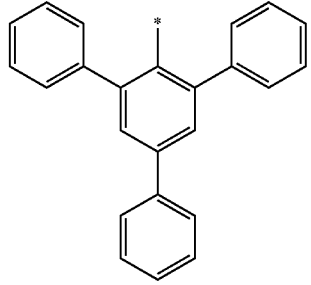
D7
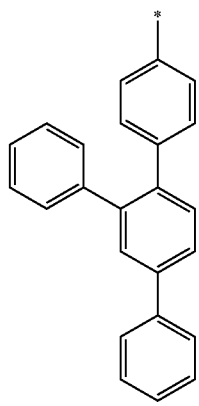
D8
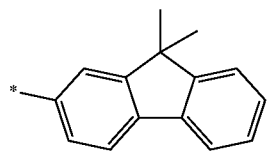
D9
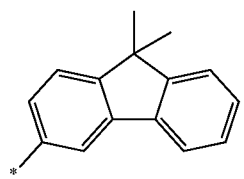
D10
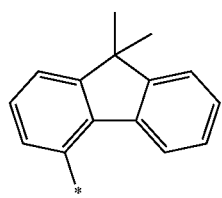
D11
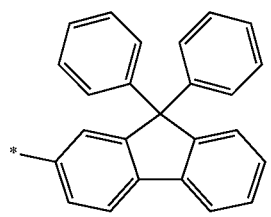
D12

-continued
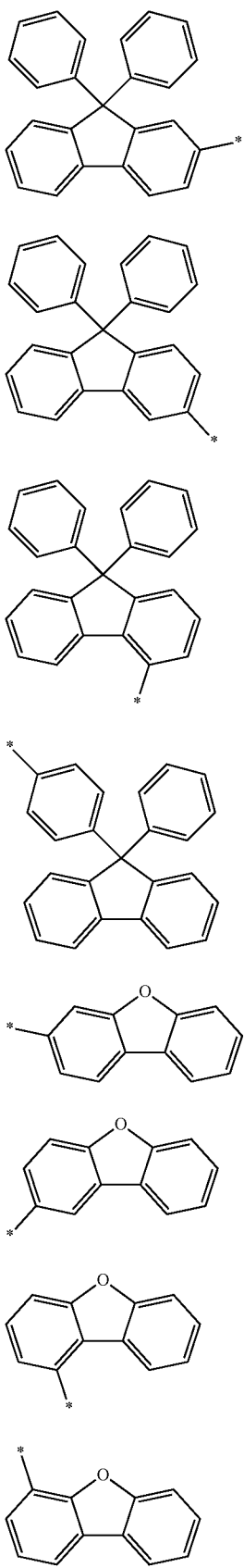
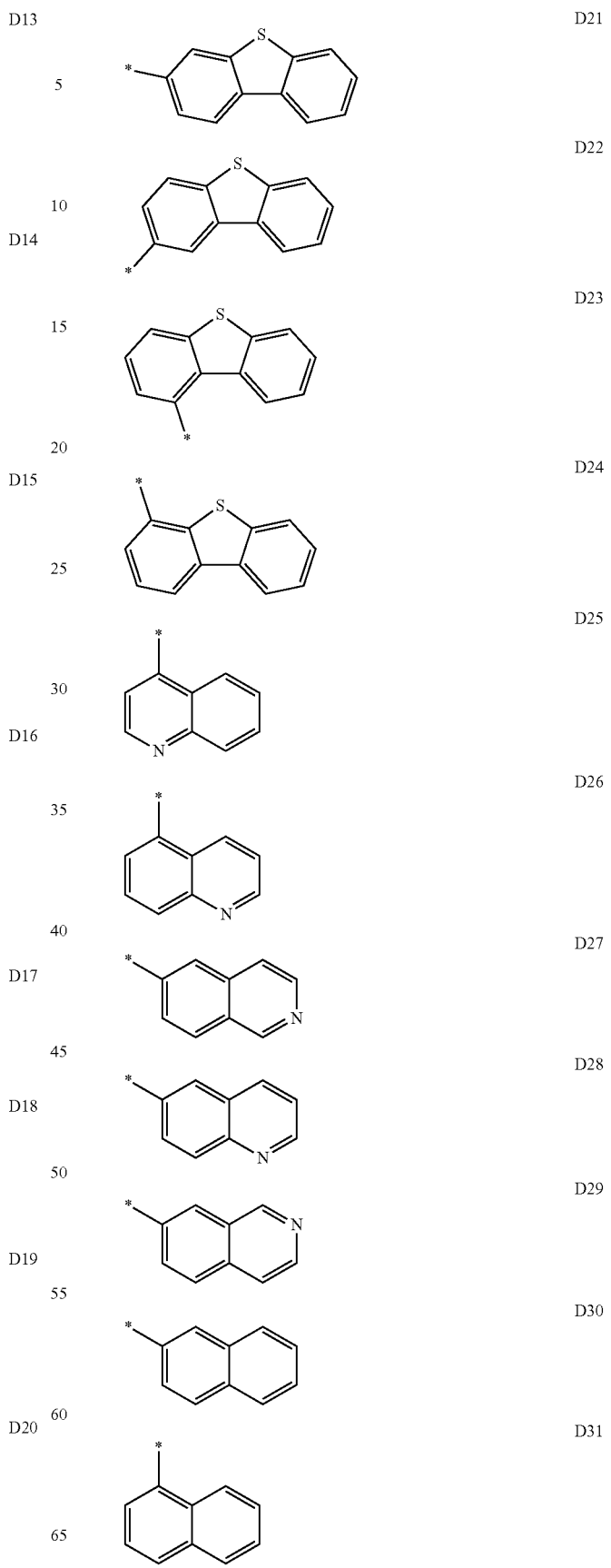

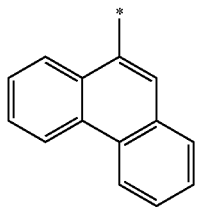
D32
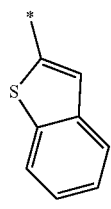
D40
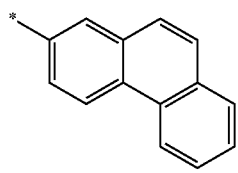
D33
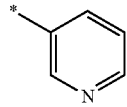
D41
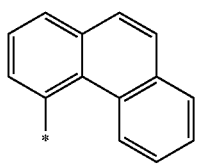
D34
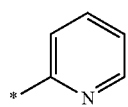
D42
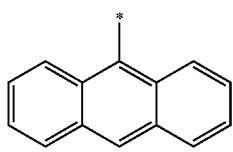
D35
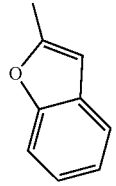
D43
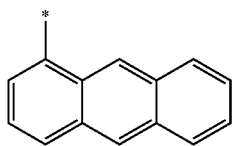
D36
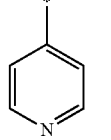
D44
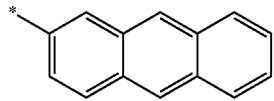
D37
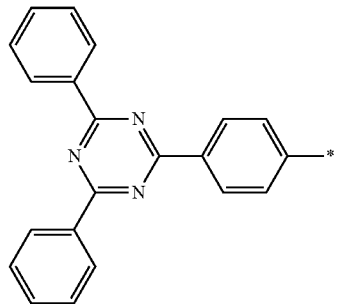
D45
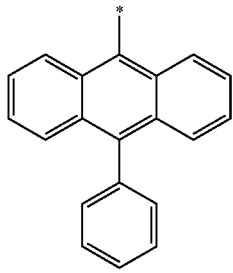
D38
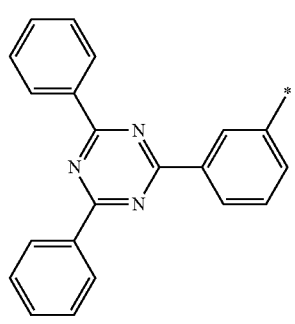
D46
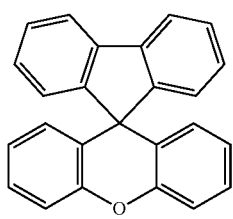
D39

-continued
D47
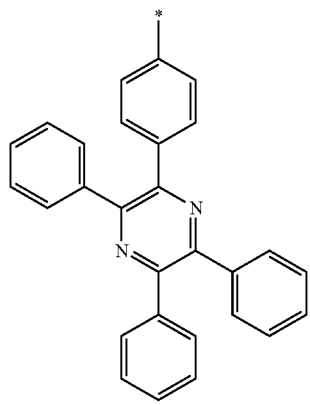
D48
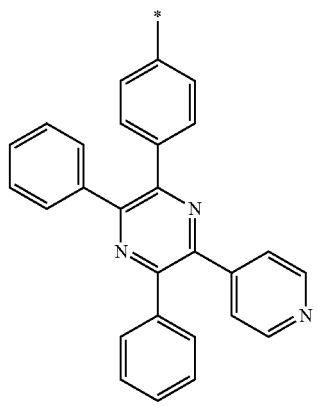
D49
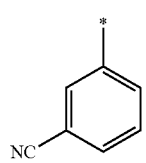
D50
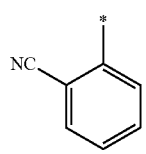
D51
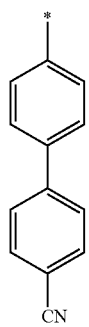
-continued
D52
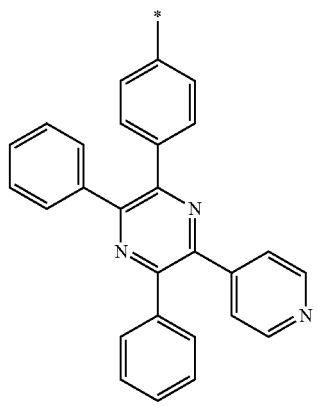
D53
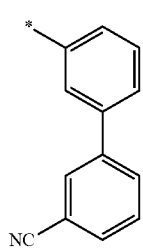
D54
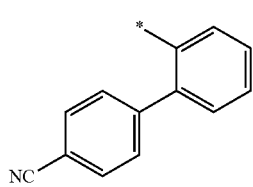
D55
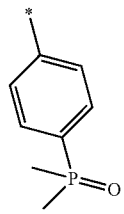
D56
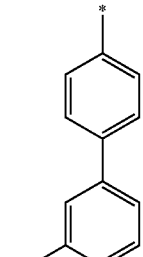
D57
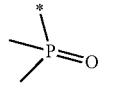

D58 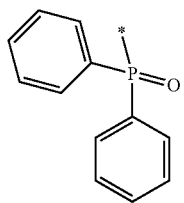

D59 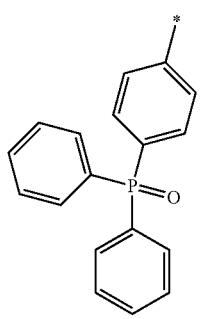

D60 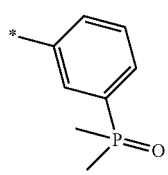

D61 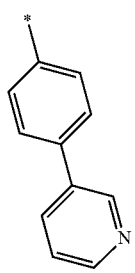

D62 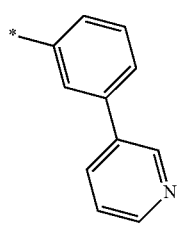

D63 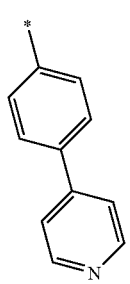

D64 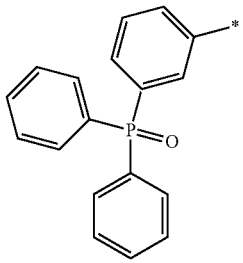

D65 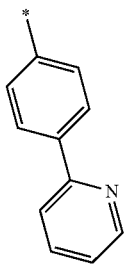

D66 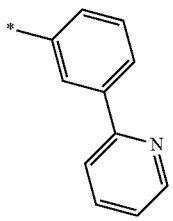

D67 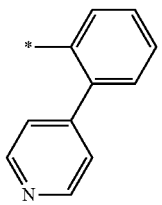

D68 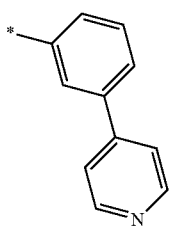

D69 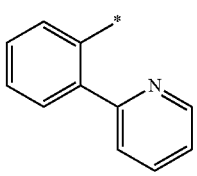

In a further embodiment $L^2$ represents a direct bond or is selected from the group consisting of phenylene, biphenylene, triphenylene, naphthylene, dibenzofurene, dibenzothiophene, carbazolene, pyridine, phenylpyridine, quinoline.

In a further embodiment, it may be provided that all $L^2$ groups comprised in the compound of Formula (I) are independently selected from the following group of structures.

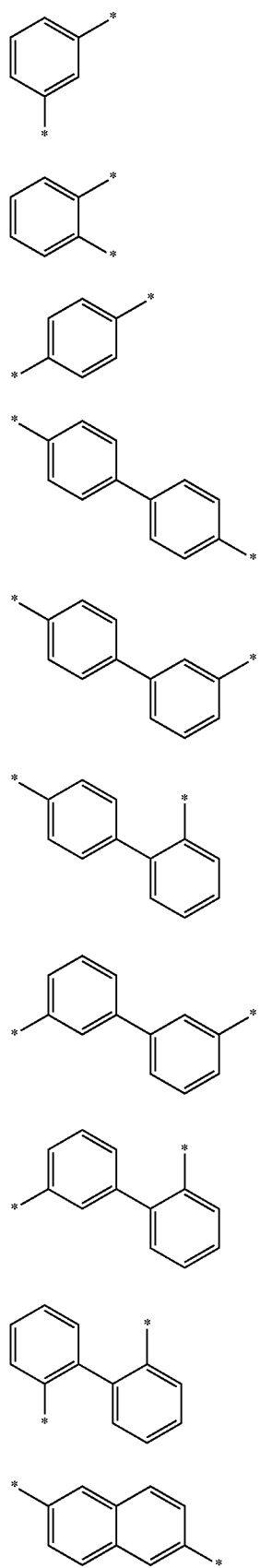
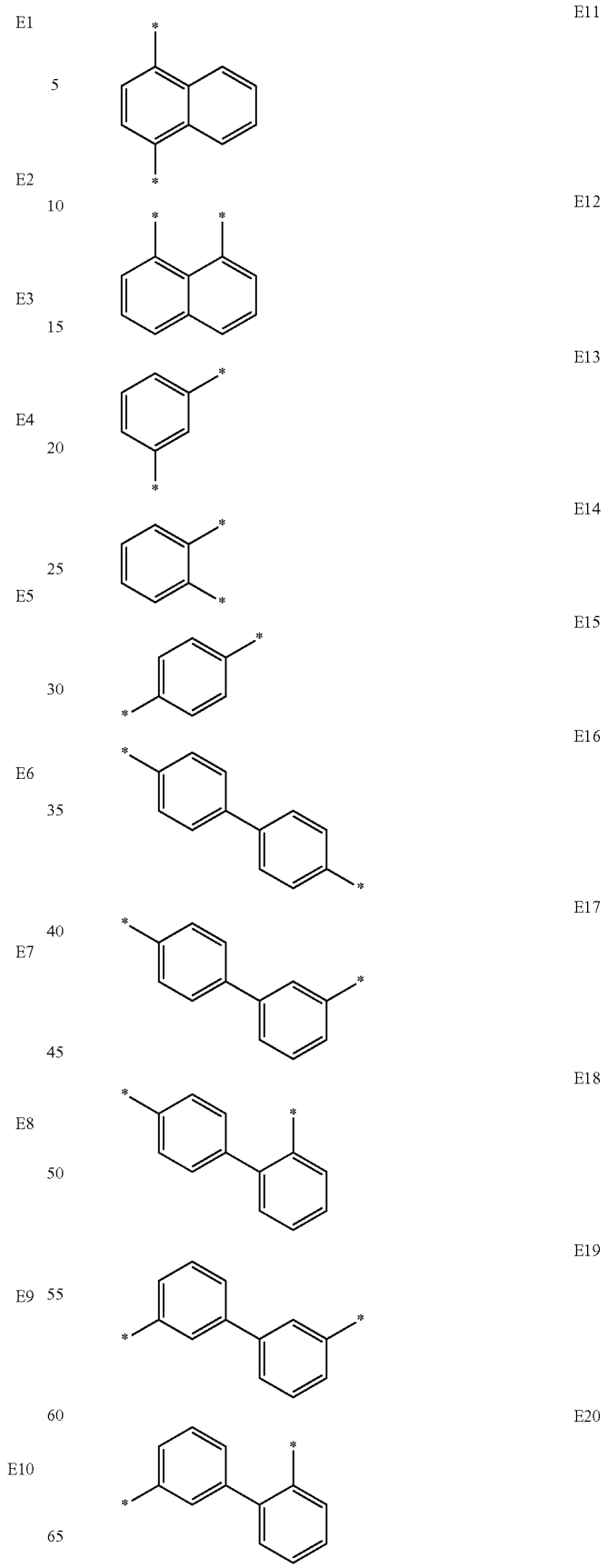

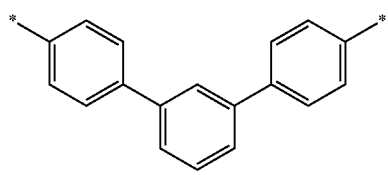 E21
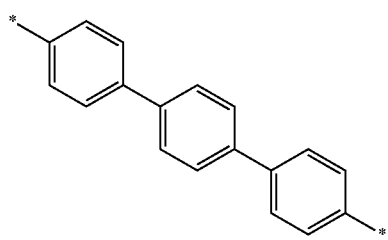 E22
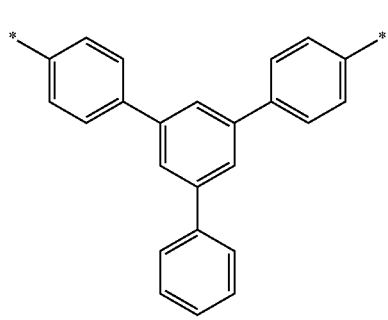 E23
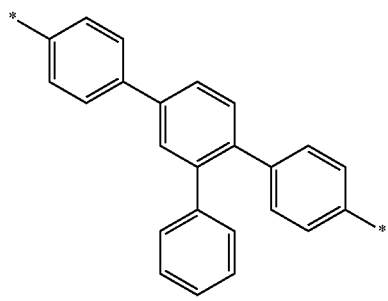 E24
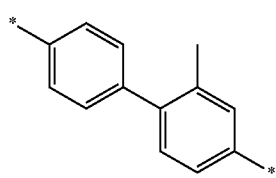 E25
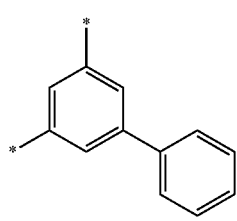 E26
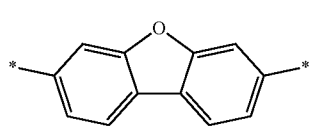 E27
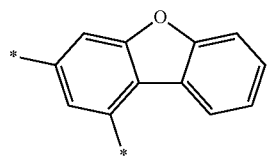 E28
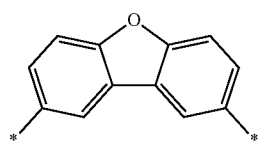 E29
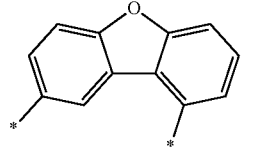 E30
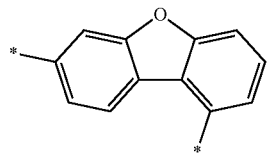 E31
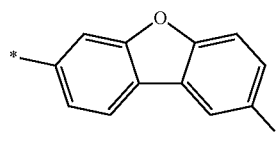 E32
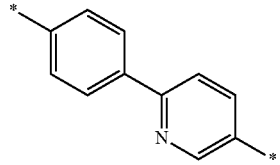 E33
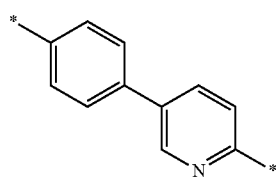 E34
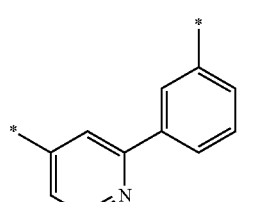 E35
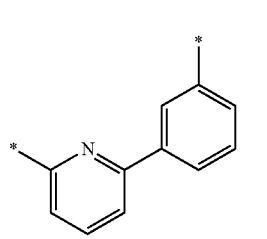 E36

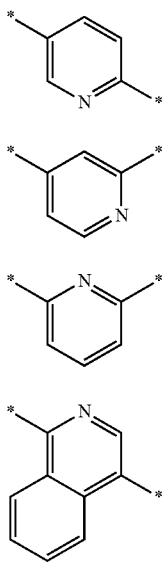

E37

E38

E39

E40

Ar¹ may be independently selected from the group consisting of phenyl, biphenyl, terphenyl, phenantherenyl, benzophenantherenyl, naphthyl, fluorenyl, dimethyl fluorenyl, diphenylfluorenyl, 9,9'-spirobi[fluorene], pyrenyl, crysenyl, fluoranthenyl, tetraphenylethenyl, nitrile, spiro[fluorene-9,9'-xanthene], benzothiophenyl, dibenzofuranyl, carbazolyl, benzothiphenyl, benzofuranyl, benzooxazolyl, benzothiazolyl, benzimidazolyl, quinazolinyl, quinoxalinyl, quinolinyl, acridinyl, benzacridinyl, dibenzoacridinyl, pyridinyl, pyrmidinyl, pyrazinyl and triazinyl wherein the respective groups may independently be substituted or unsubstituted, wherein the one or more substituent(s) if present in one or more of the groups R² are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$, wherein Y is O or S, and R³ are independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl.

All groups Ar¹ which are comprised in the compound of Formula (I) may be independently selected from the following group of structures.

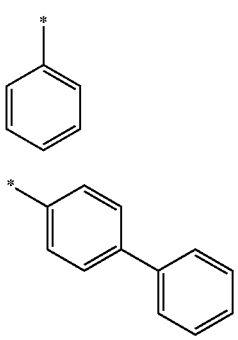

F1

F2

F3

F4

F5

F6

F7

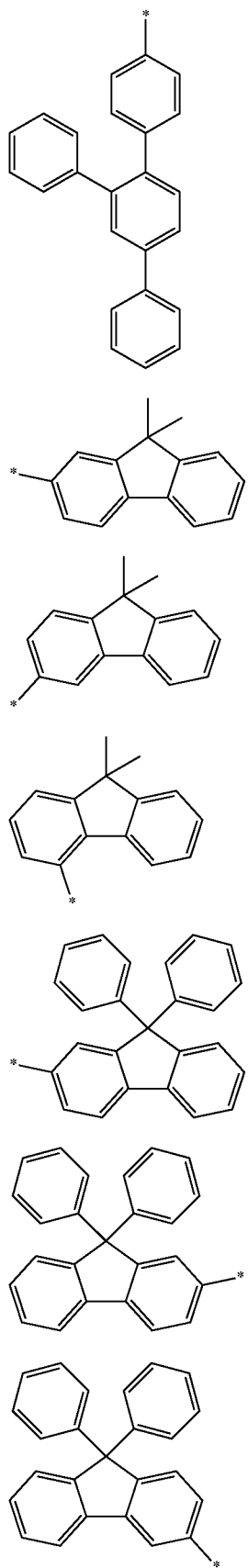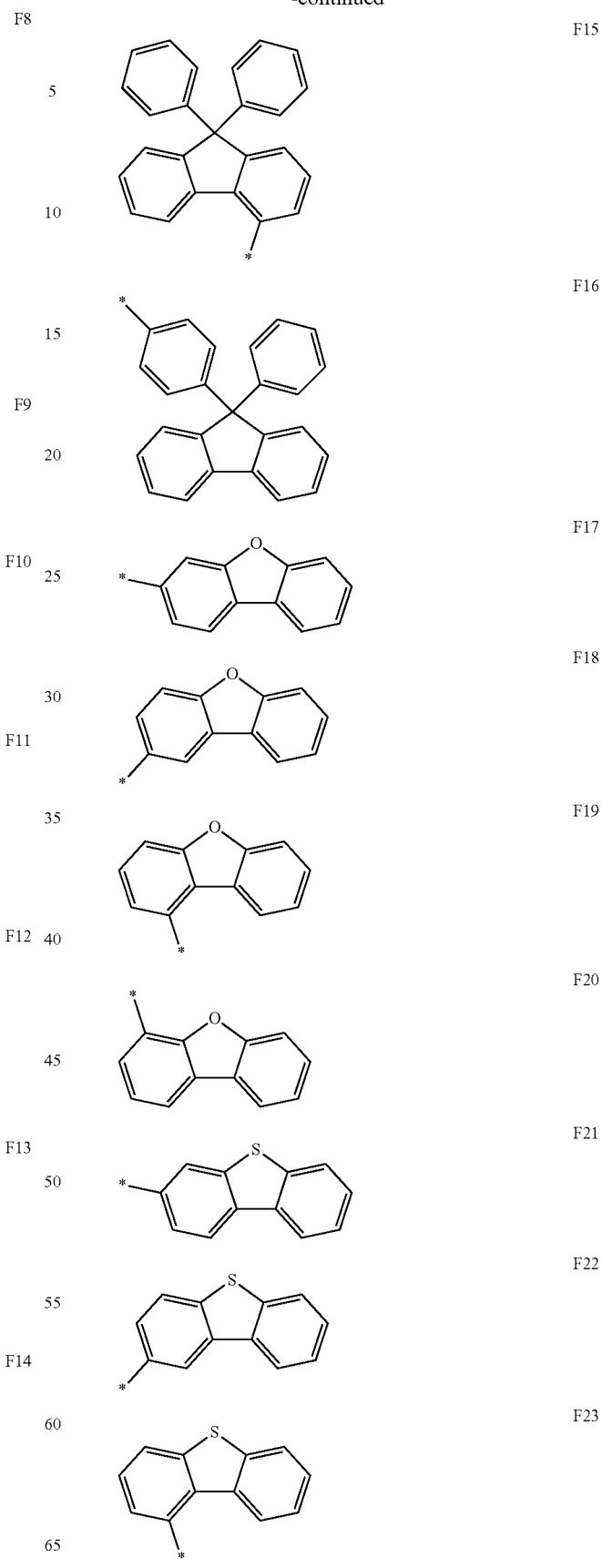

-continued
F24 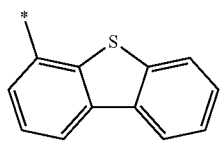
F25 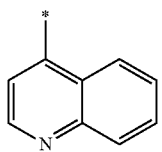
F26 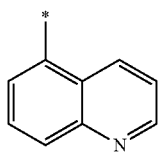
F27 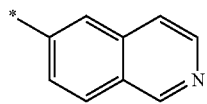
F28 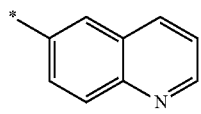
F29 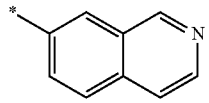
F30 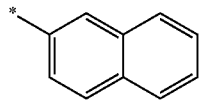
F31 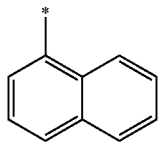
F32 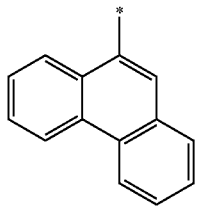
F33 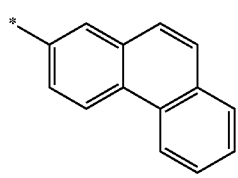
-continued
F34 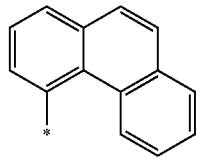
F35 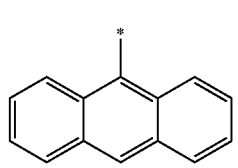
F36 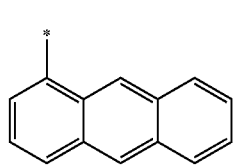
F37 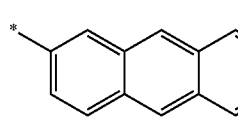
F38 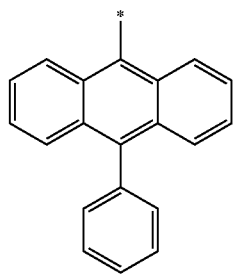
F39 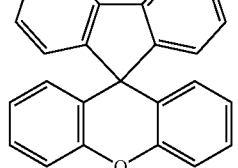
F40 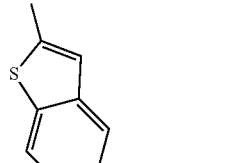
F41 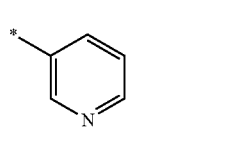
F42 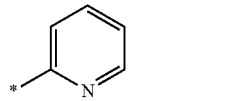

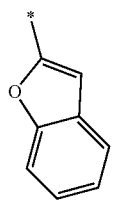
F43
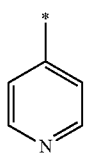
F44
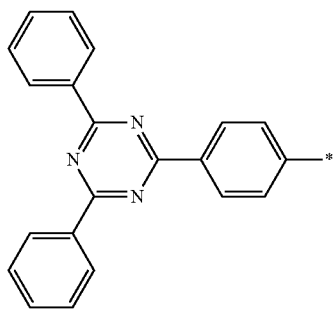
F45
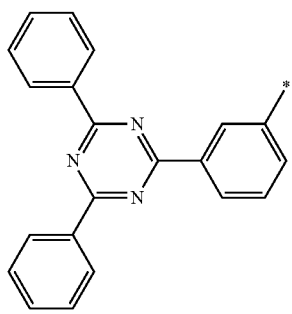
F46
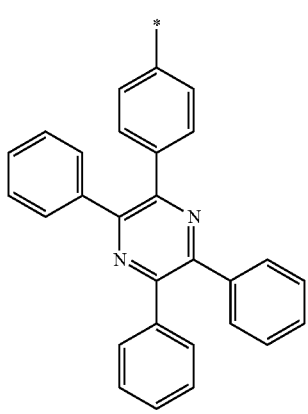
F47
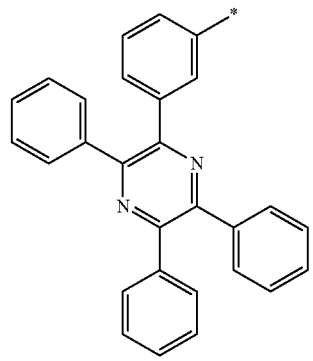
F48
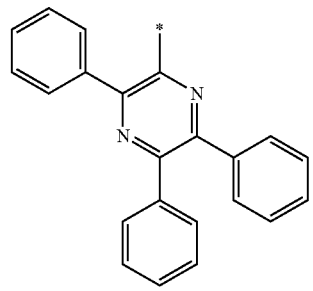
F49
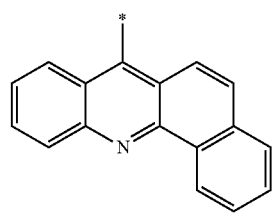
F50
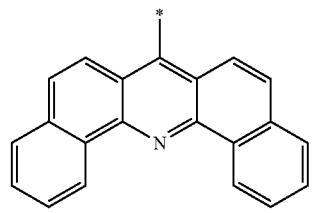
F51
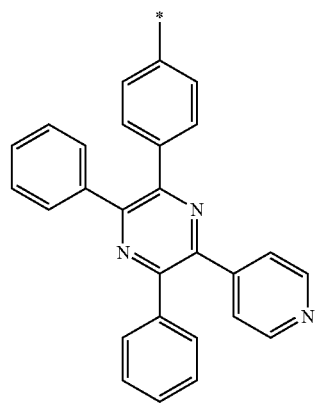
F52

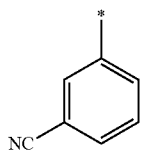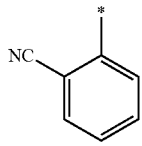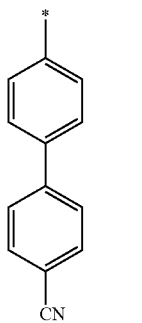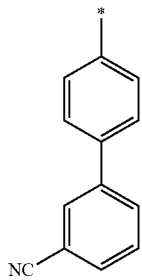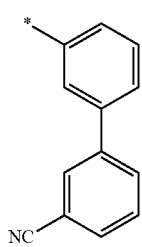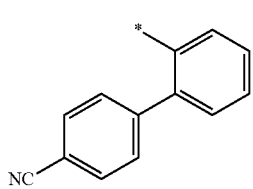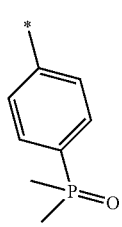
F53
F54
F55
F56
F57
F58
F59
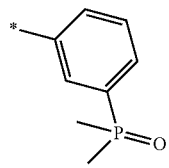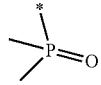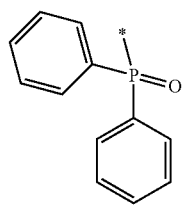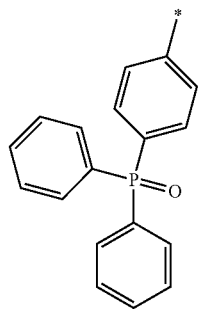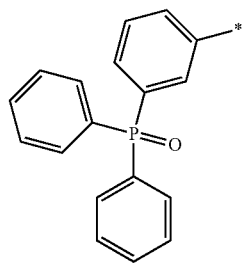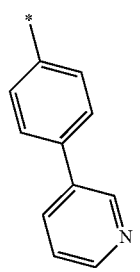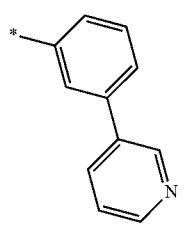
F60
F61
F62
F63
F64
F65
F66

-continued
F67 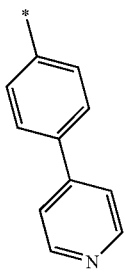
F68 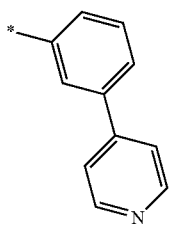
F69 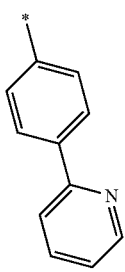
F70 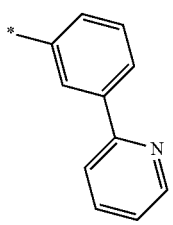
F71 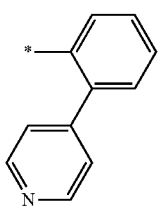
F72 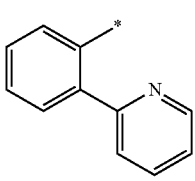
It may be provided that the compound according to Formula (I) is selected from the following groups of compounds 1 to 186.
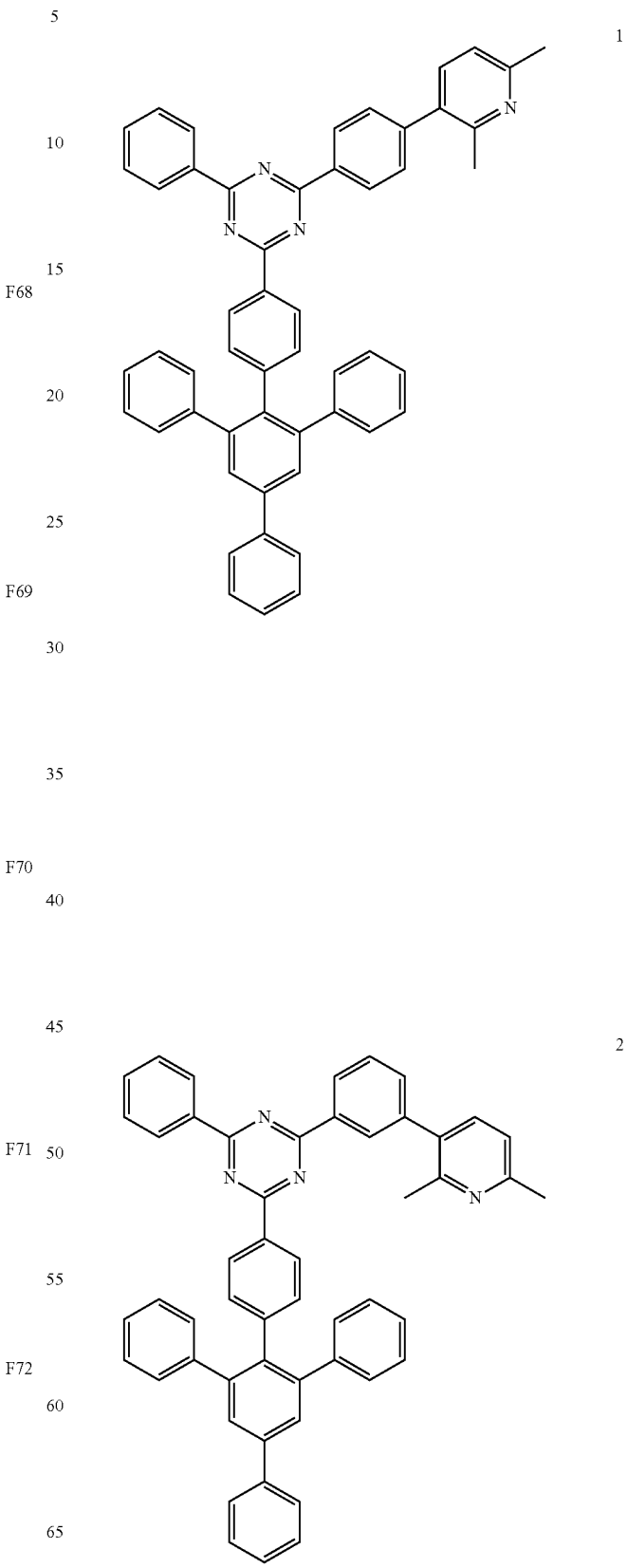

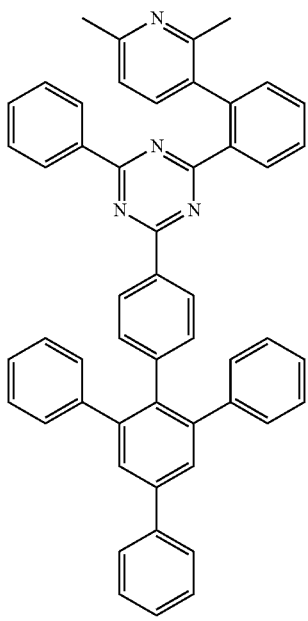
3
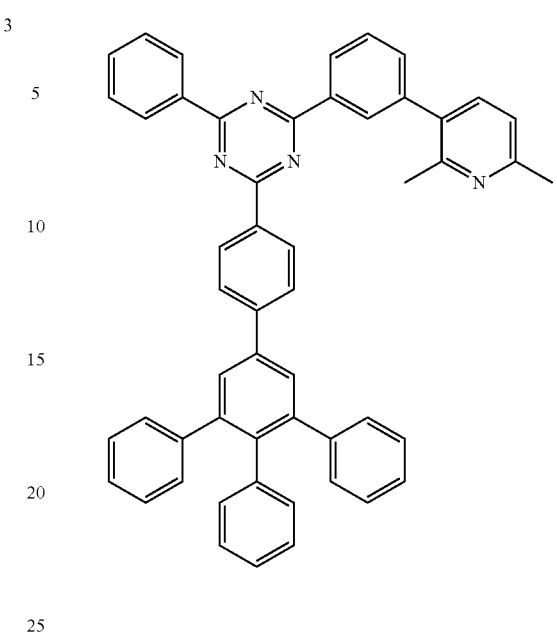
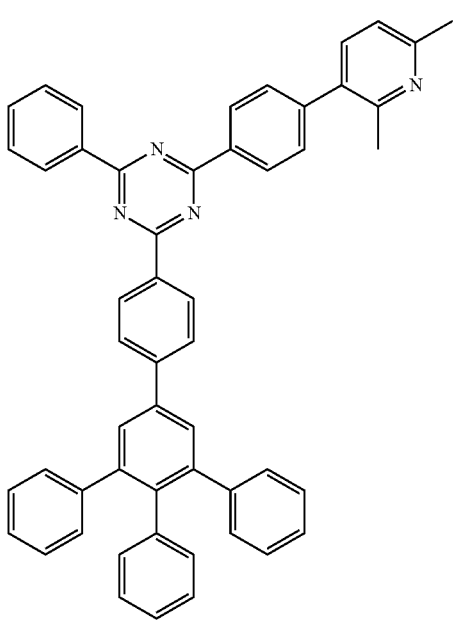
4
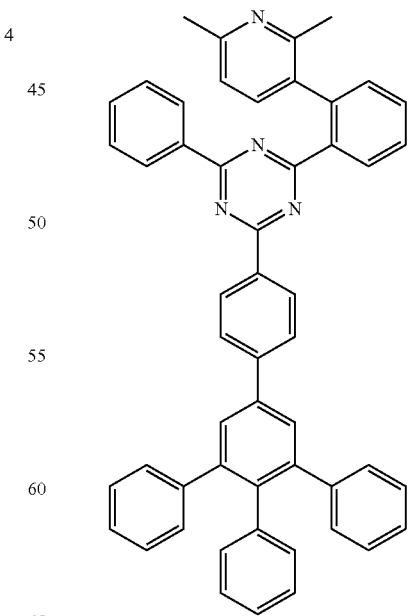

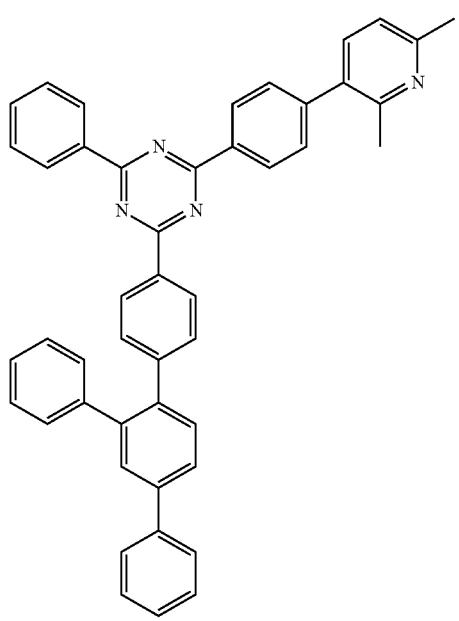
7
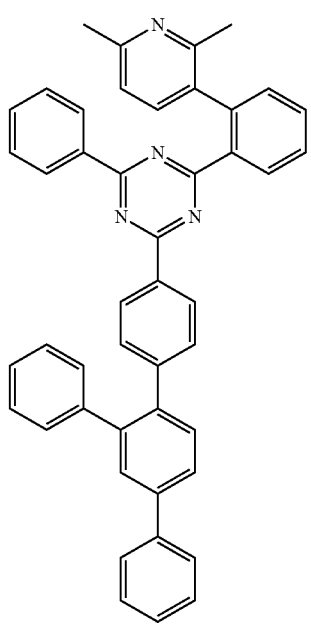
9
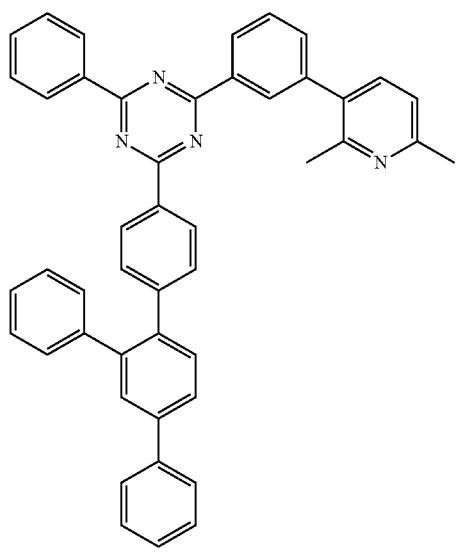
8

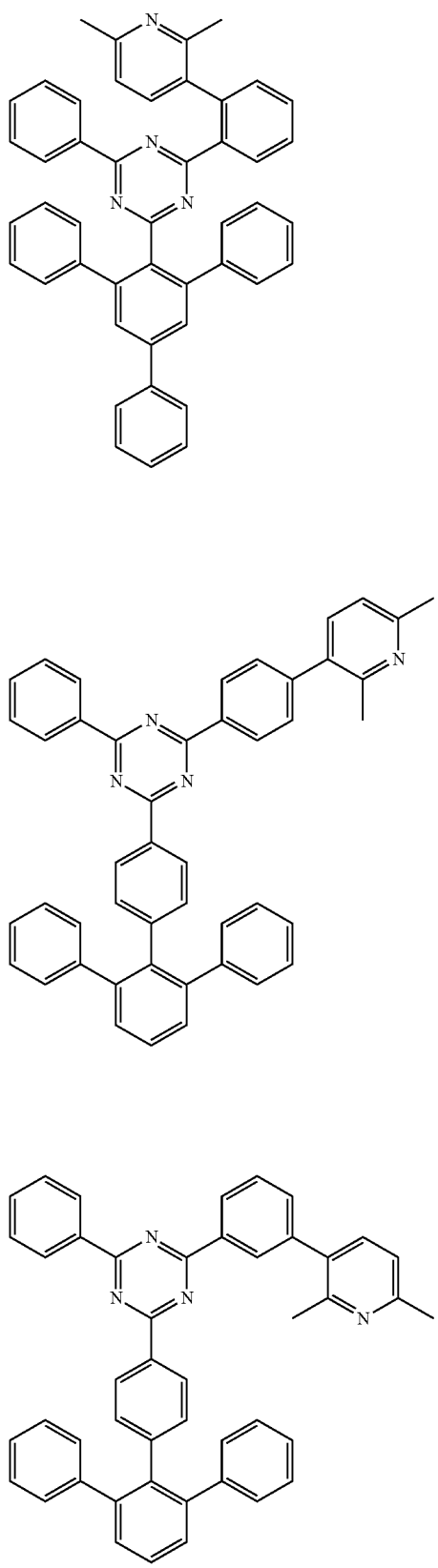
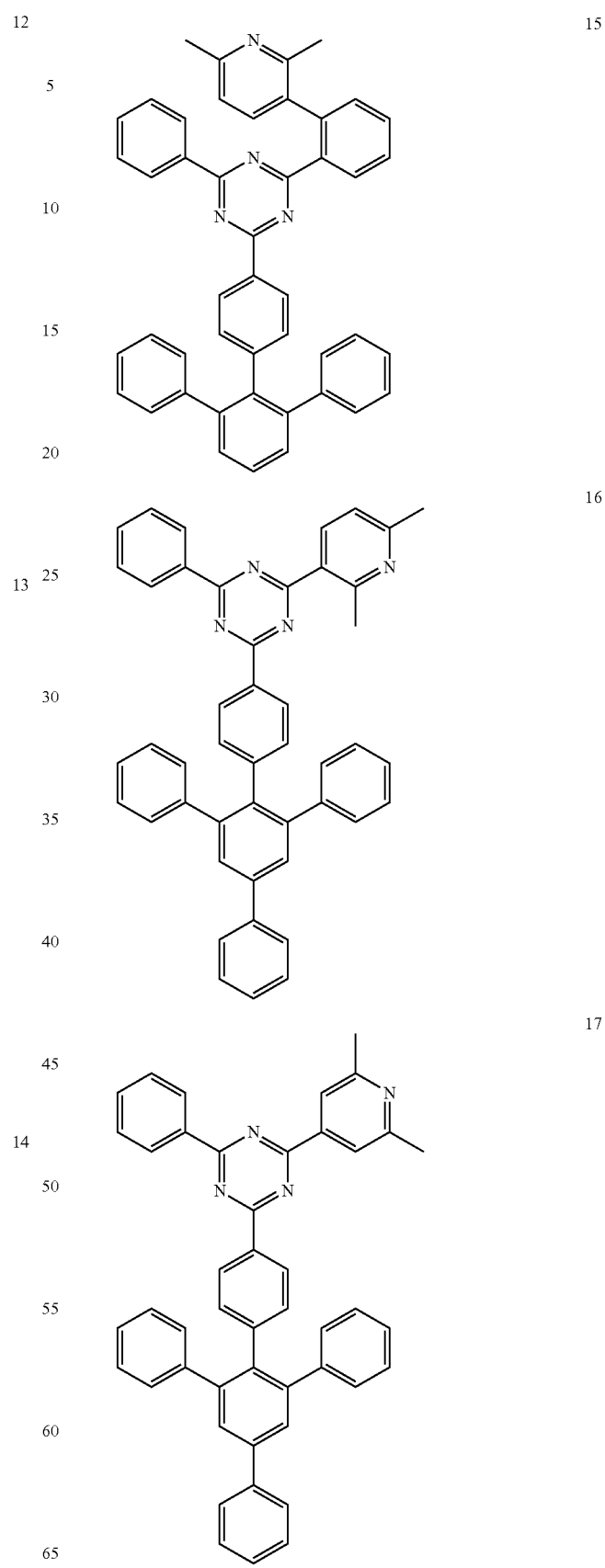

18
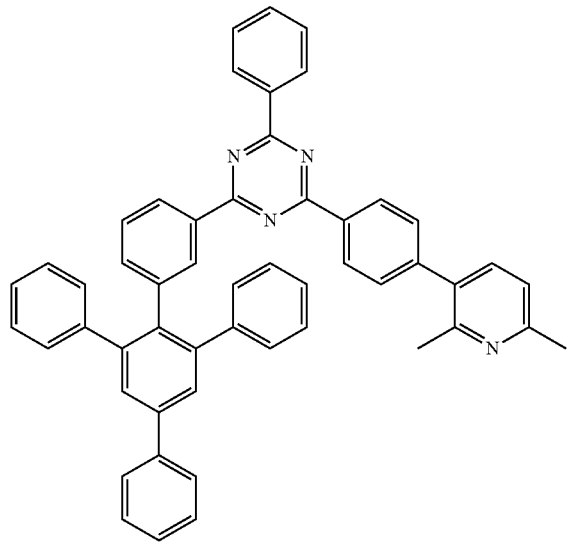
20
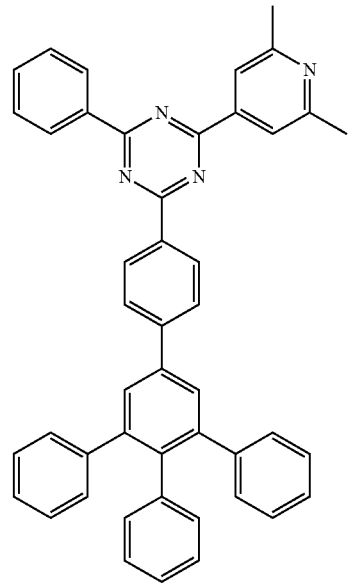
19
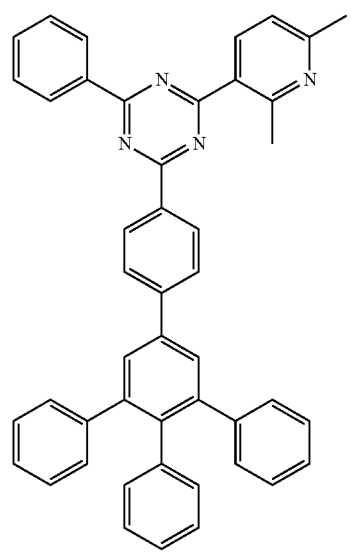
21
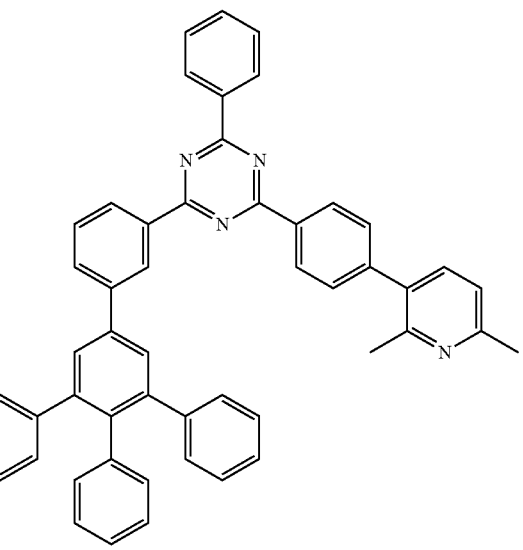

22
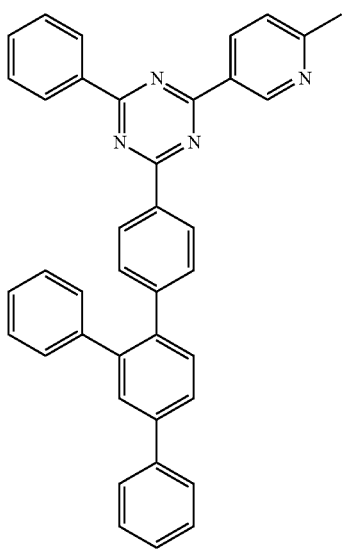
23
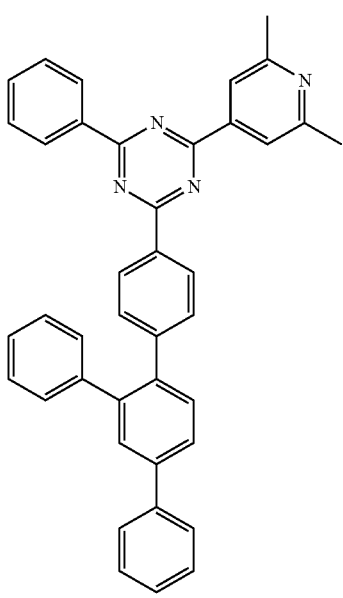
24
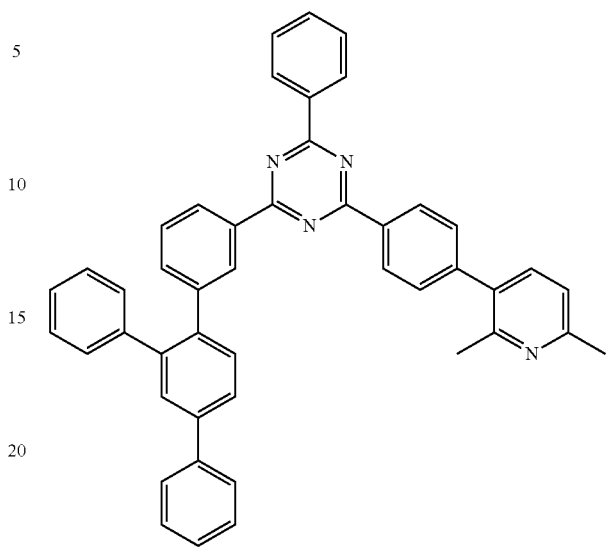
25
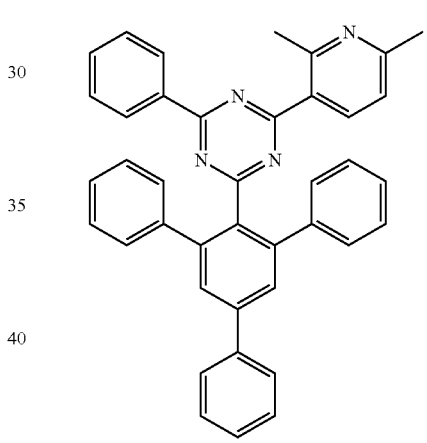
26
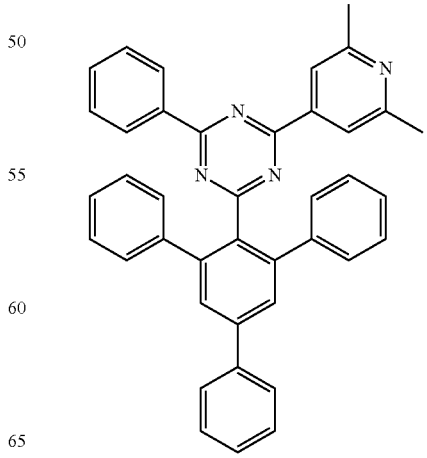

27
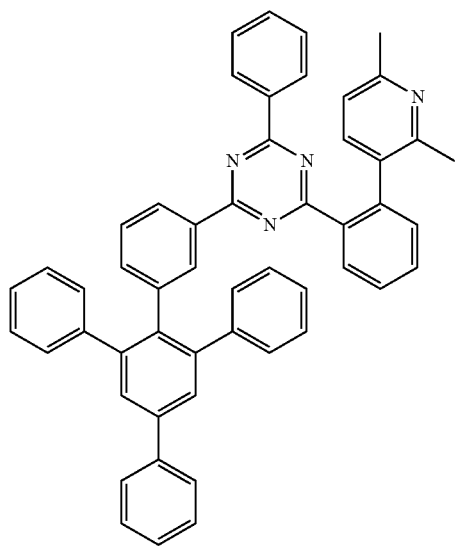
28
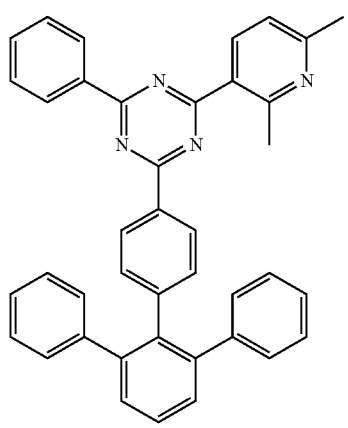
29
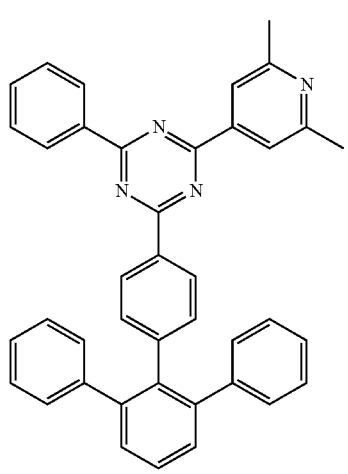
30
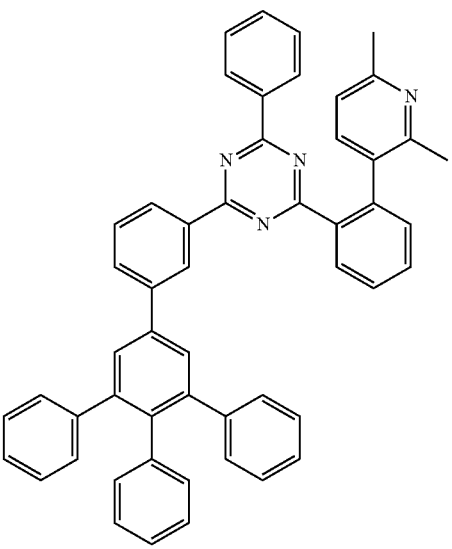
31
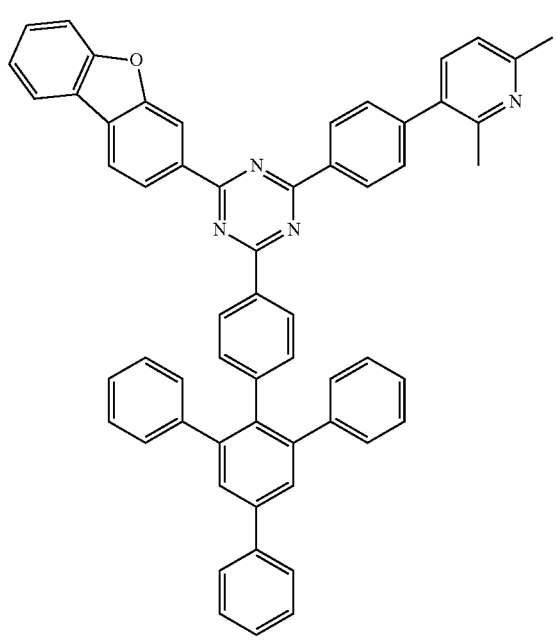

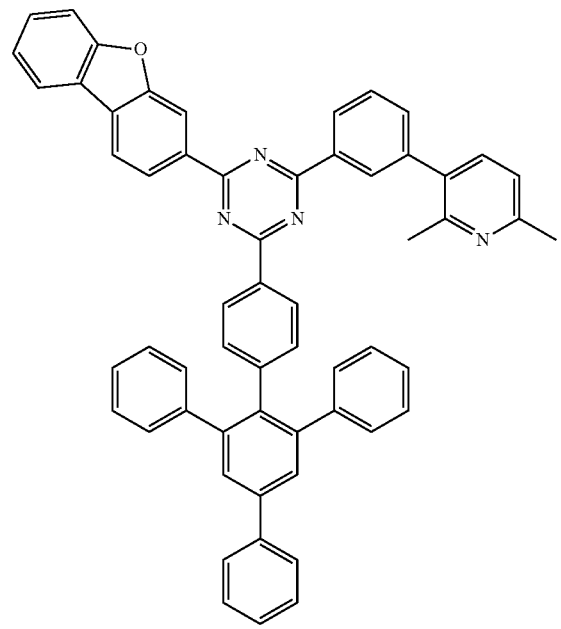
32
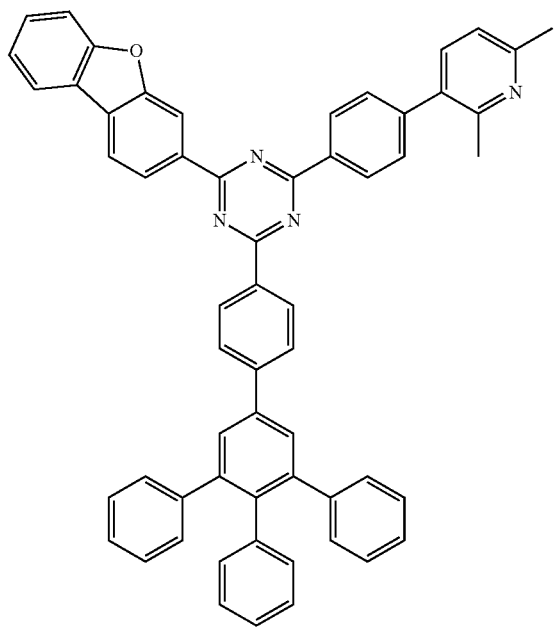
34
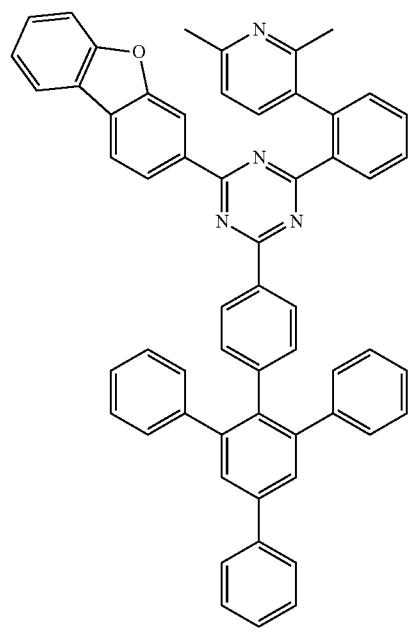
33
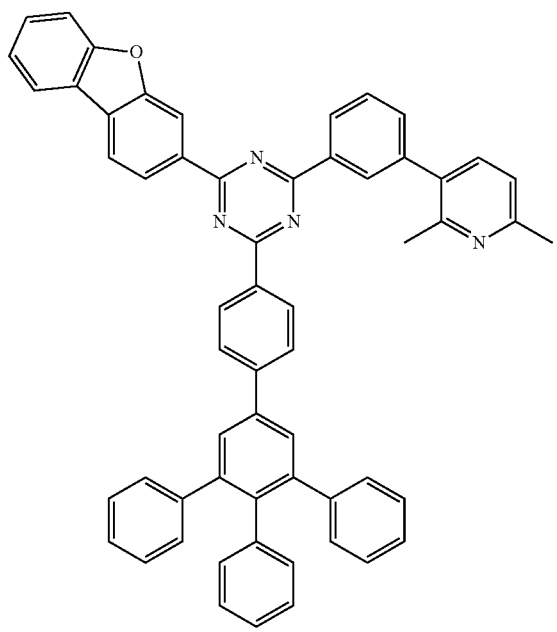
35

36
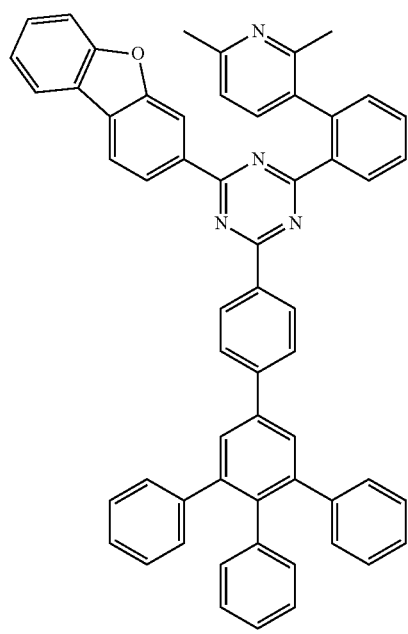
37
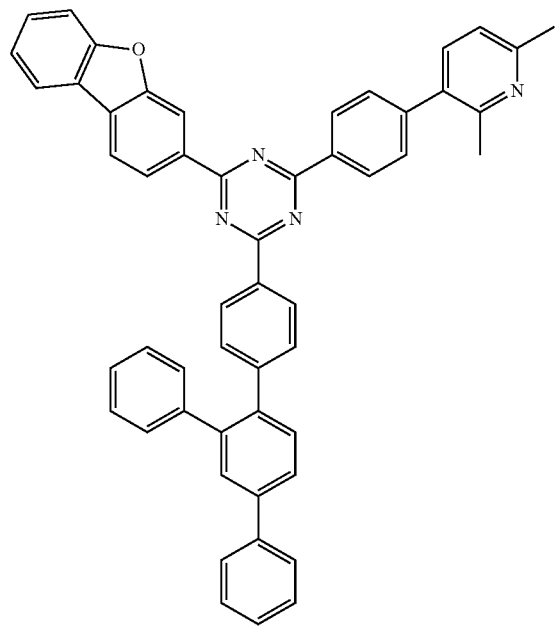
38
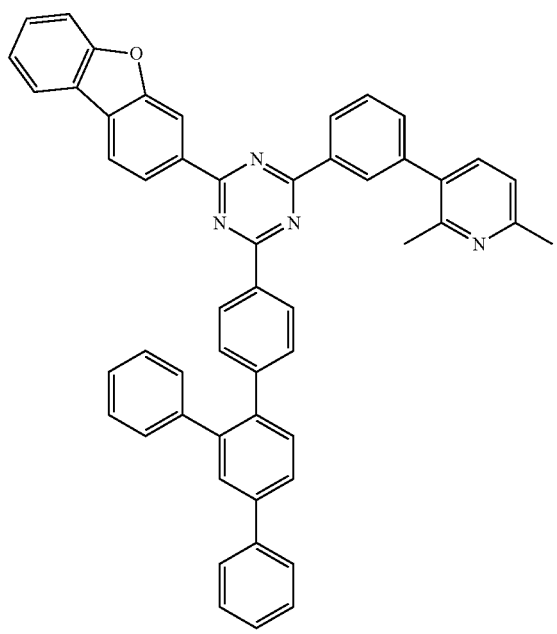
39
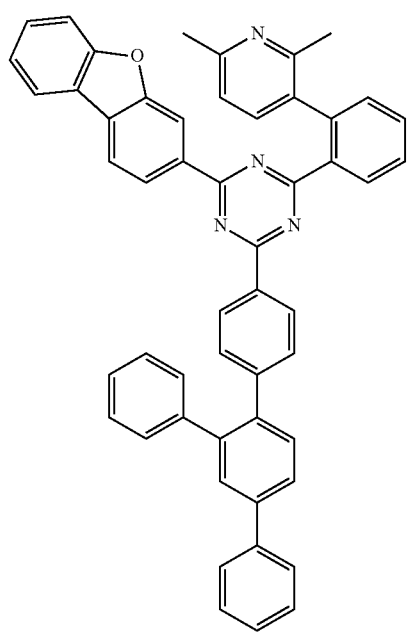

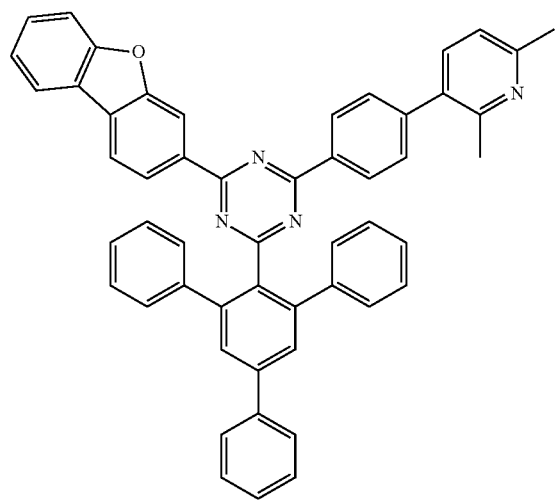
40
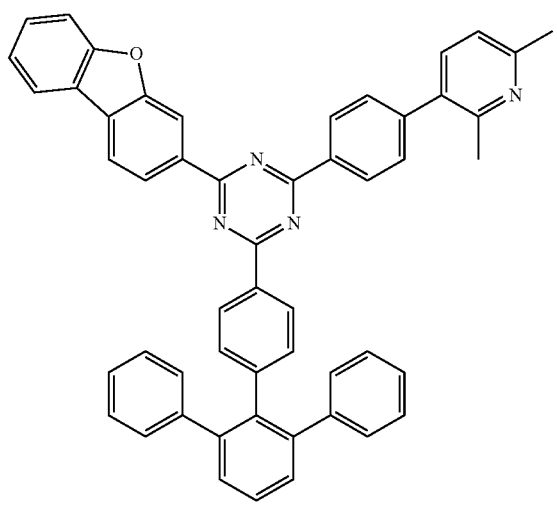
43
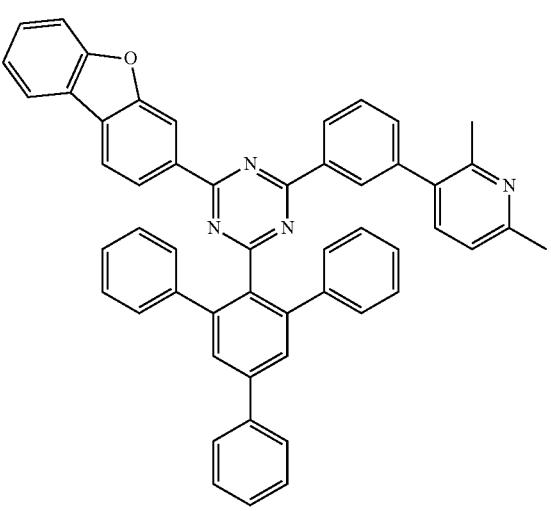
41
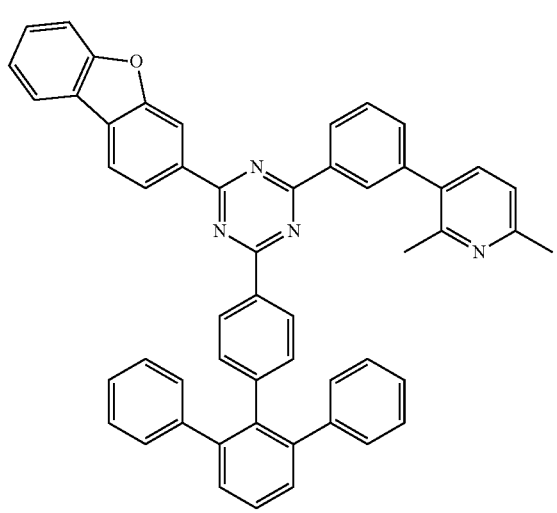
44
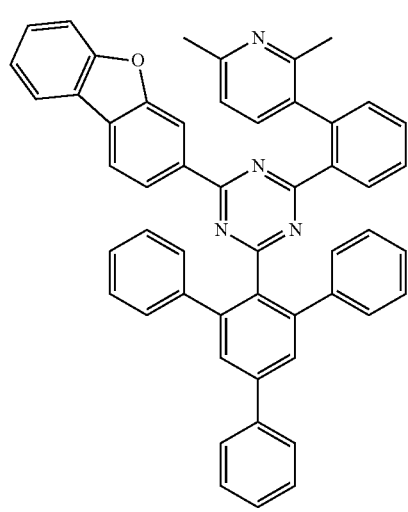
42

46
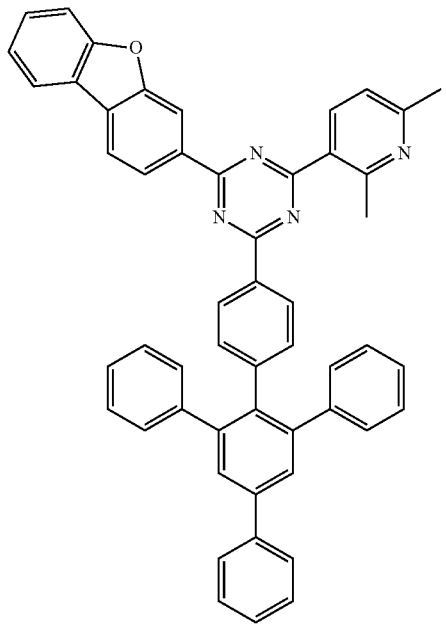
48
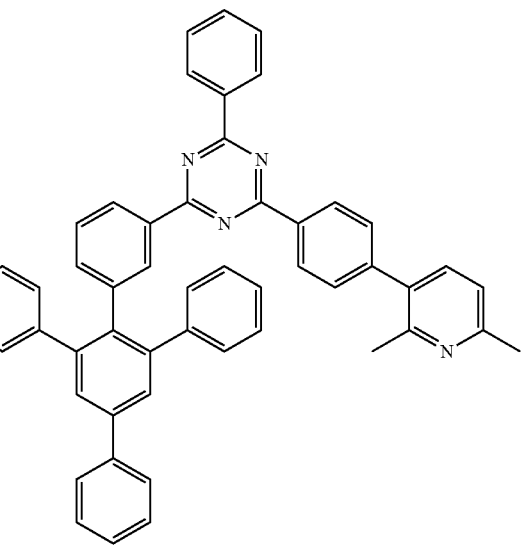
47
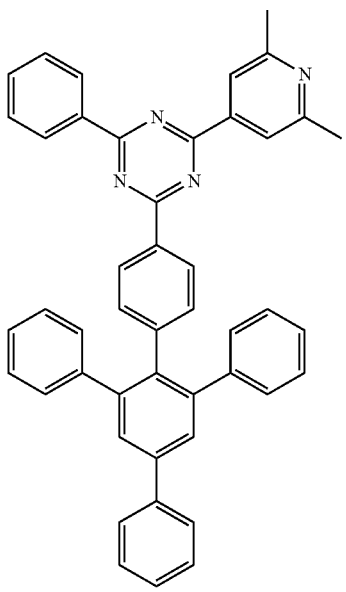
49
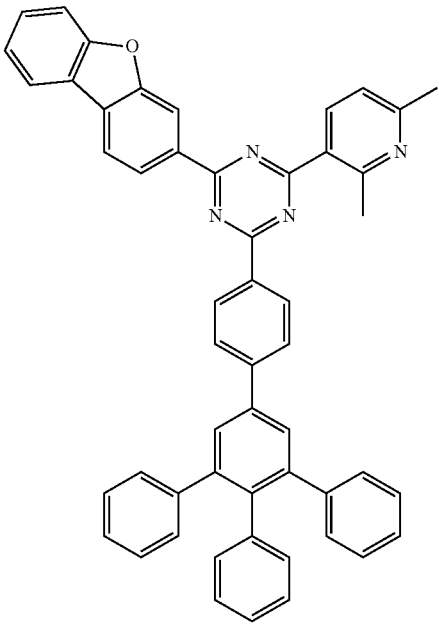

50
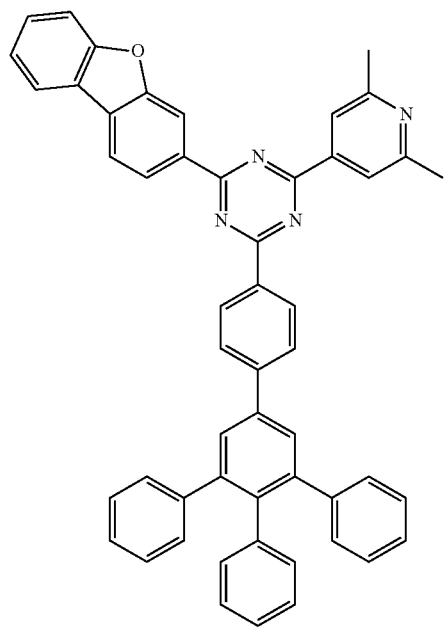
52
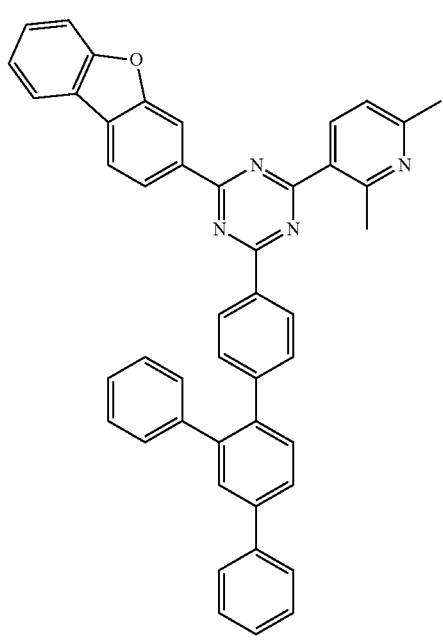
51
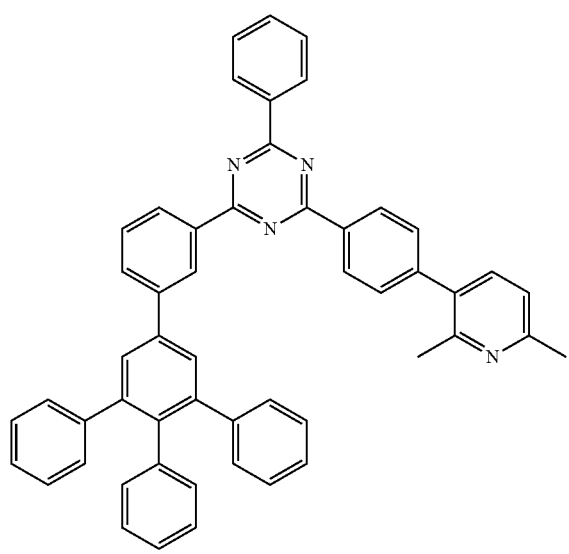
53
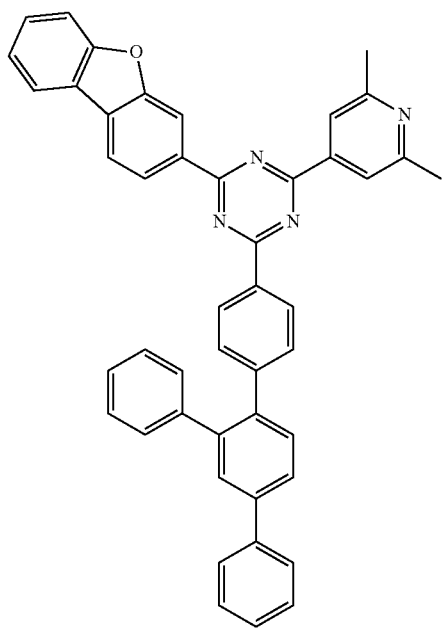

54
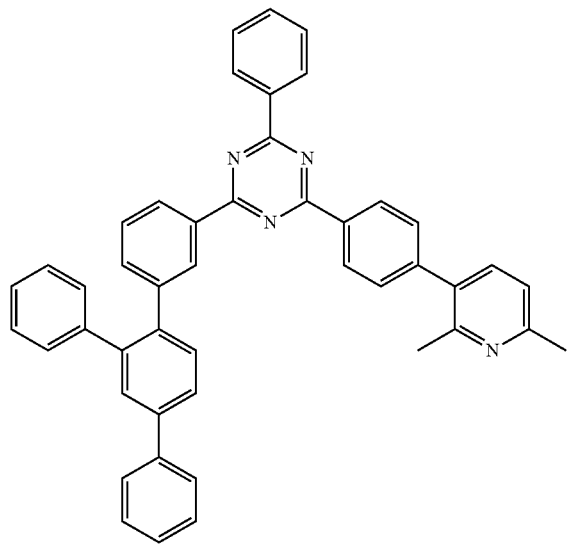
55
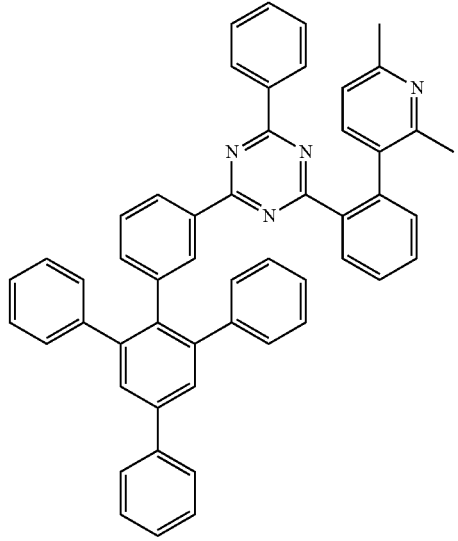
57
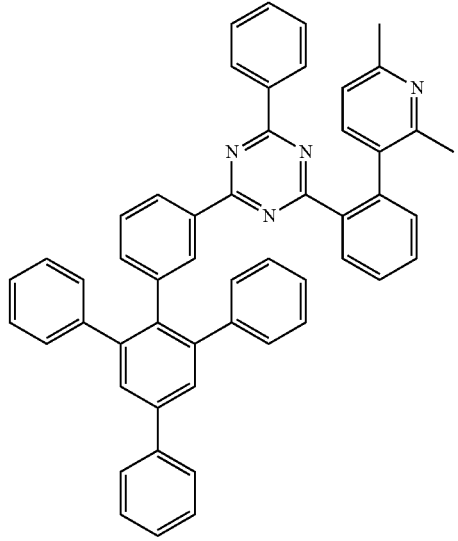
58
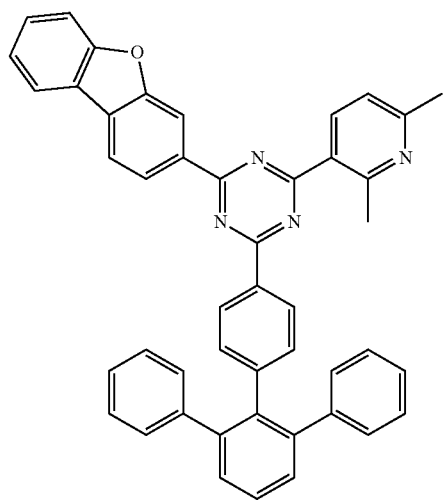
56
59
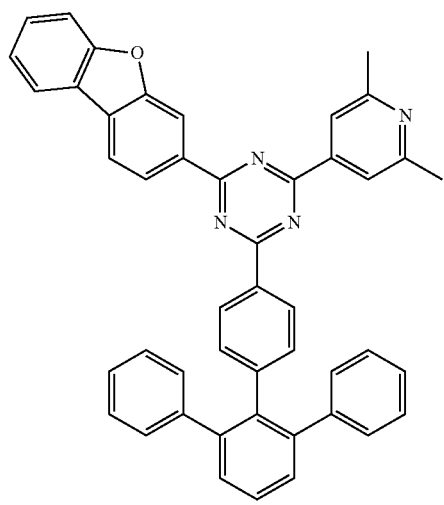

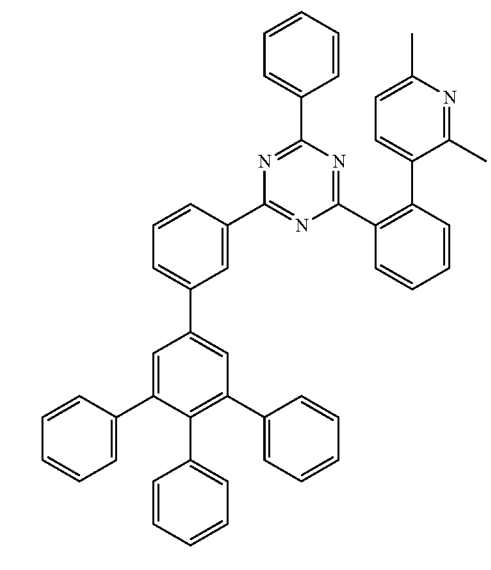
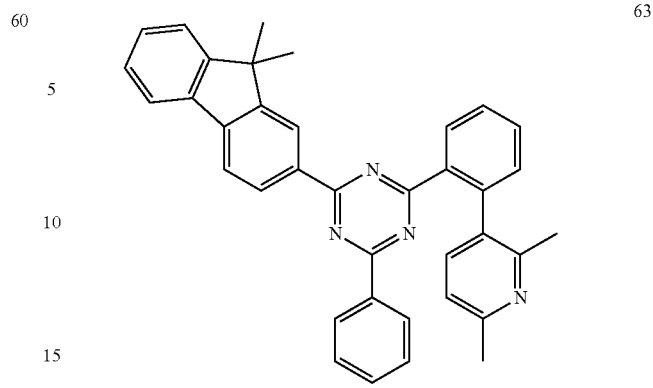
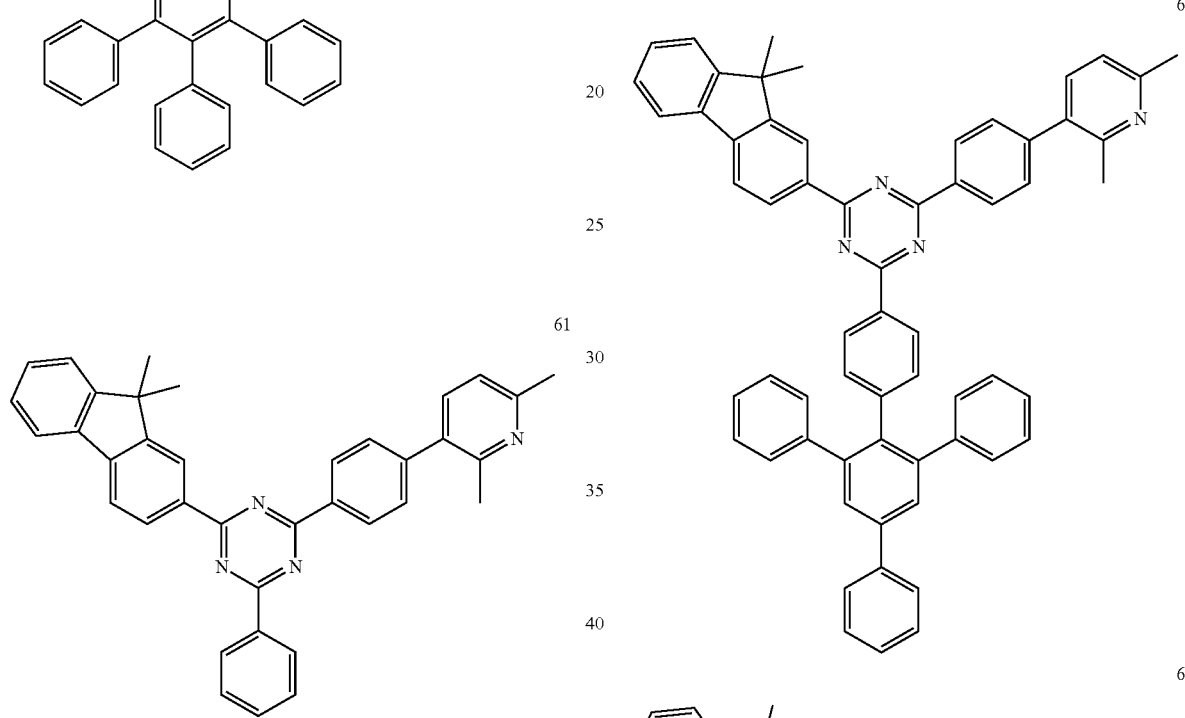
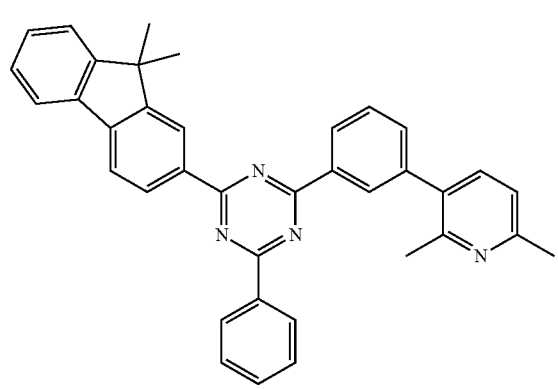
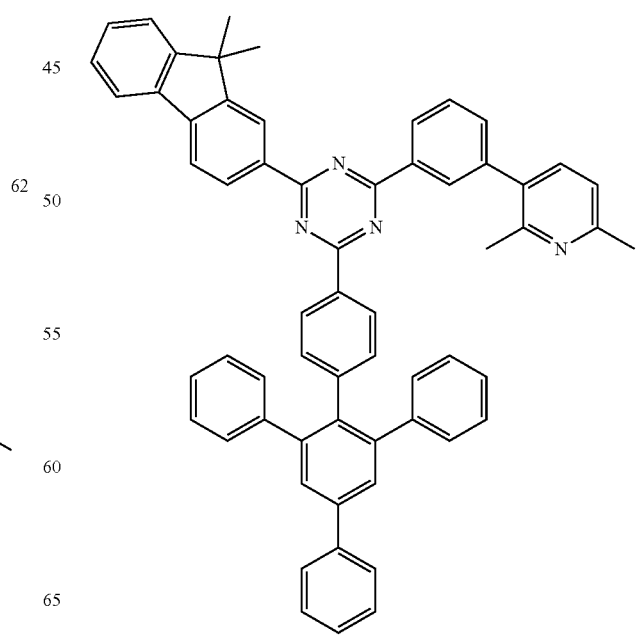

66
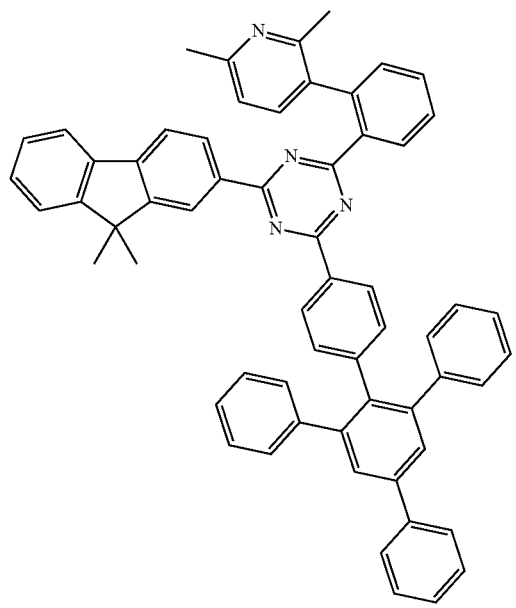
67
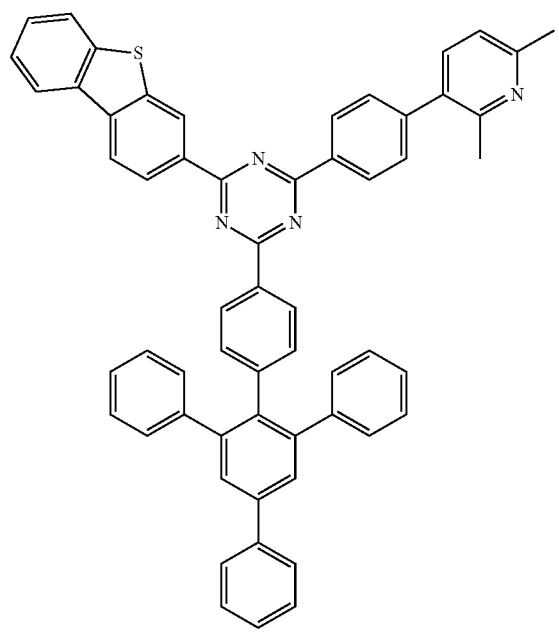
68
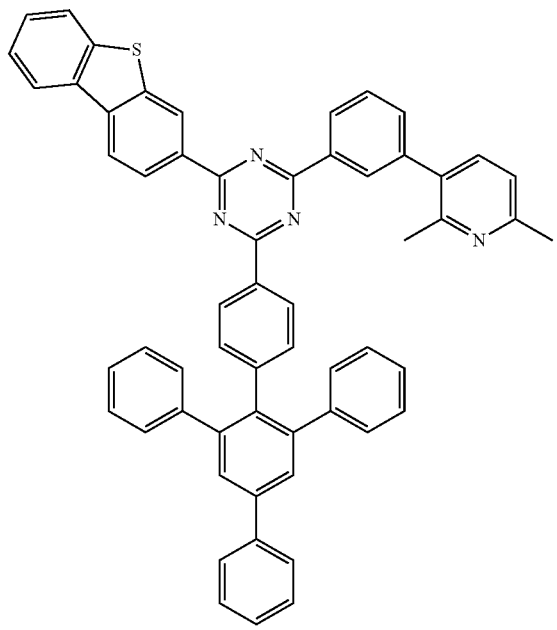
69
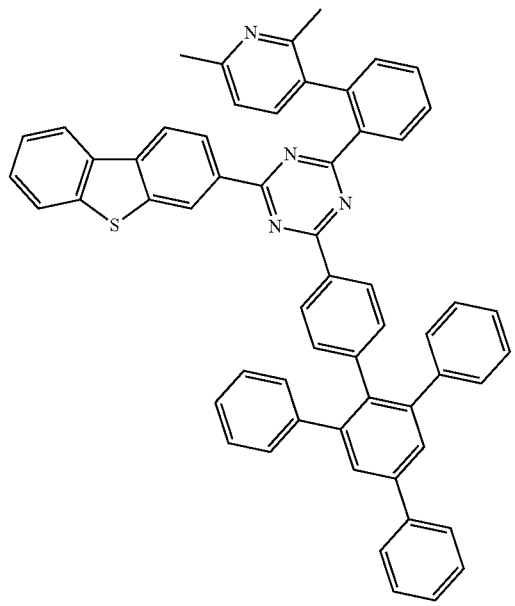

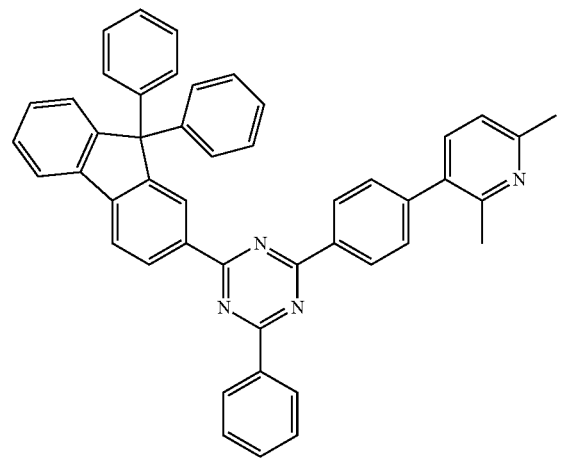
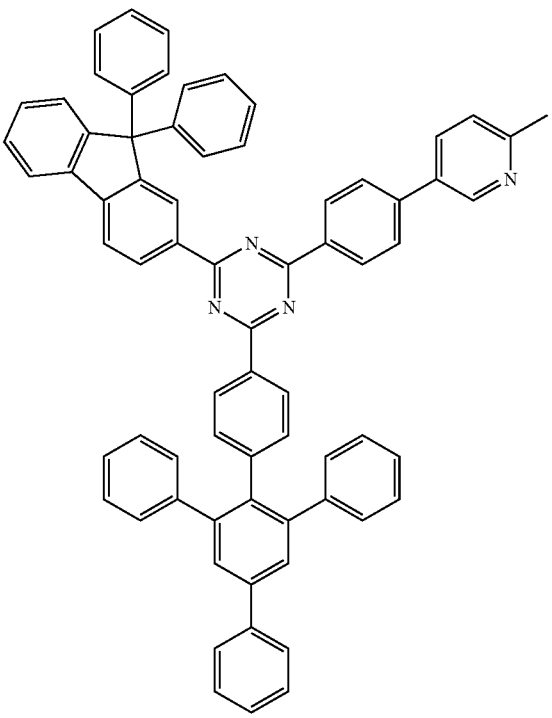
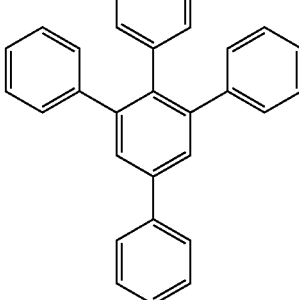
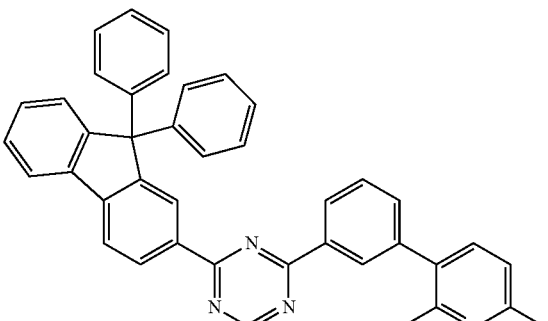
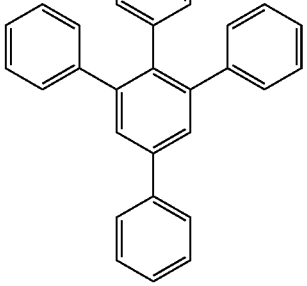

75
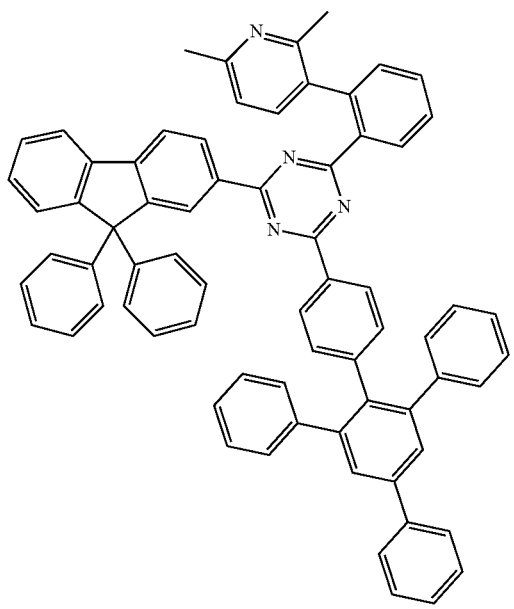
76
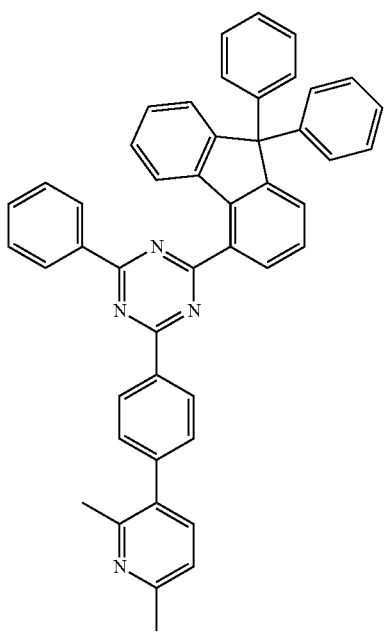
77
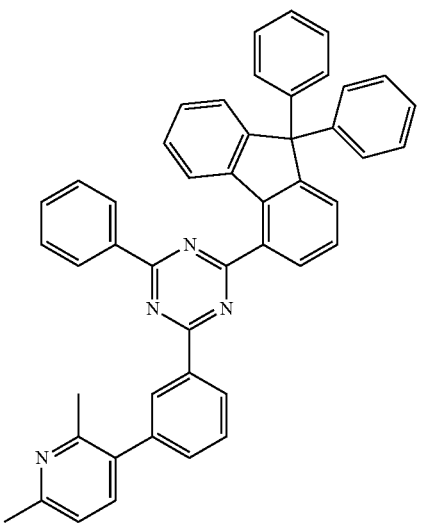
78
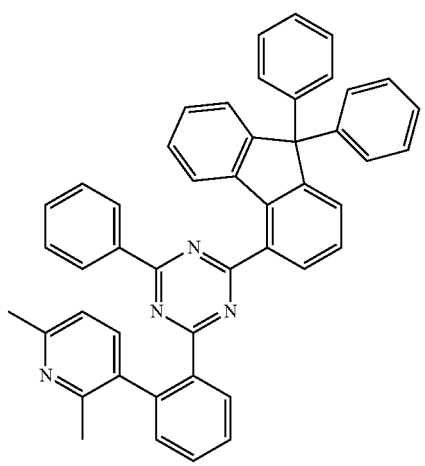
79
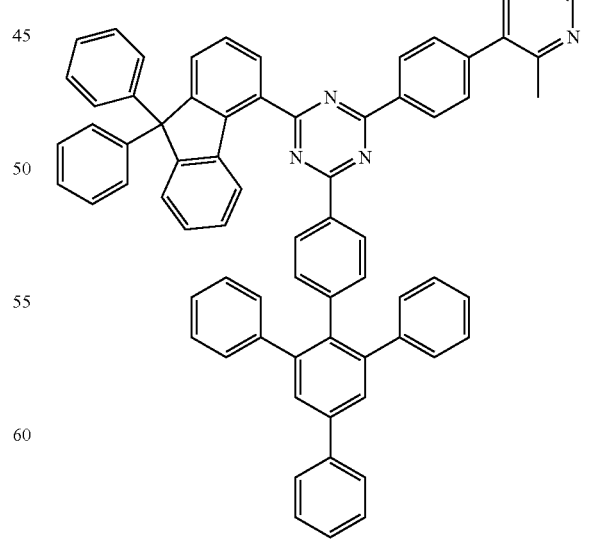

80
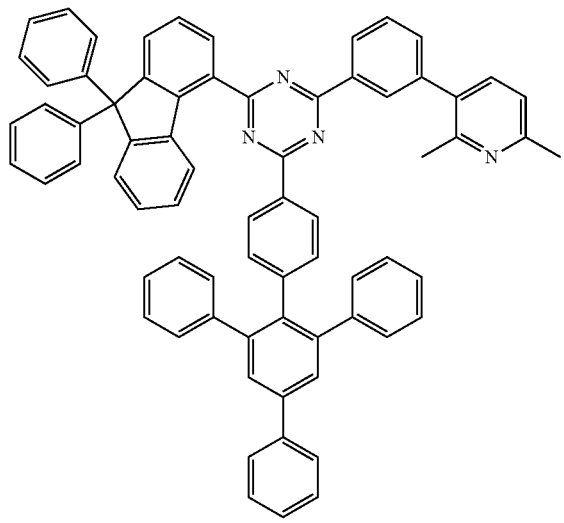
81
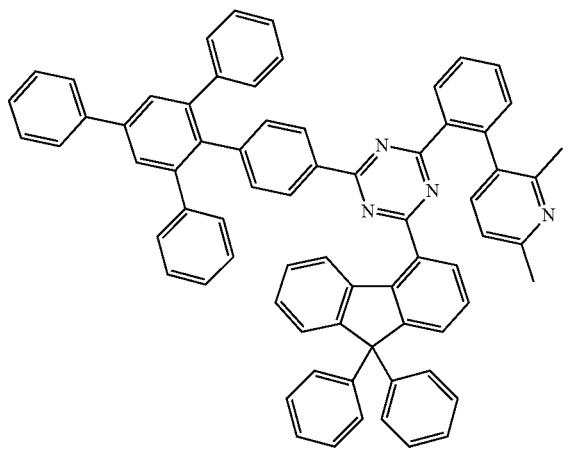
82
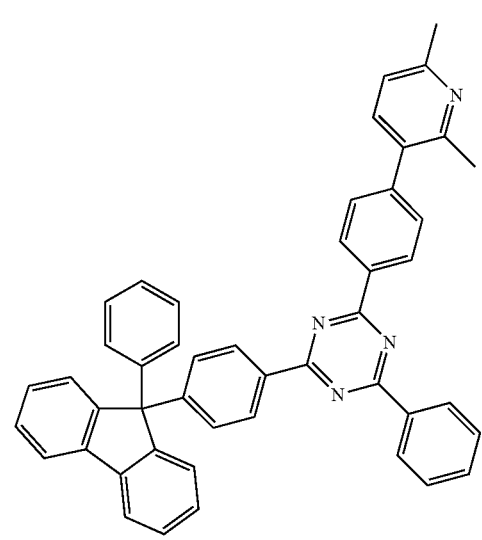
83
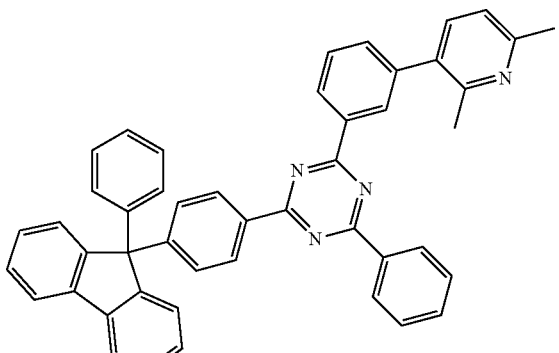
84
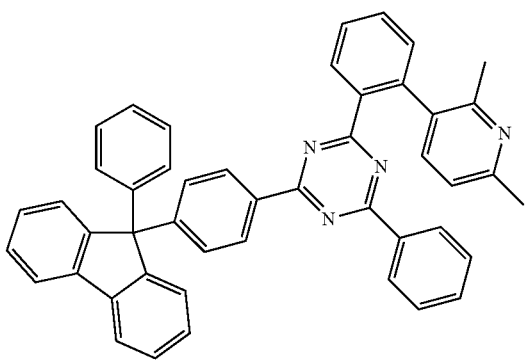
85
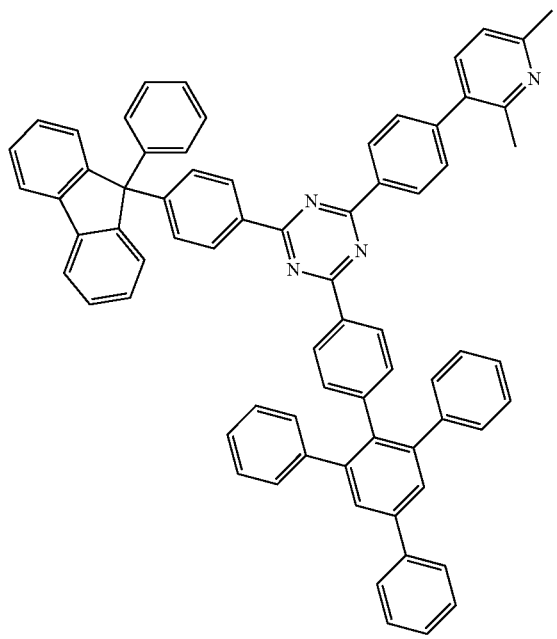

86
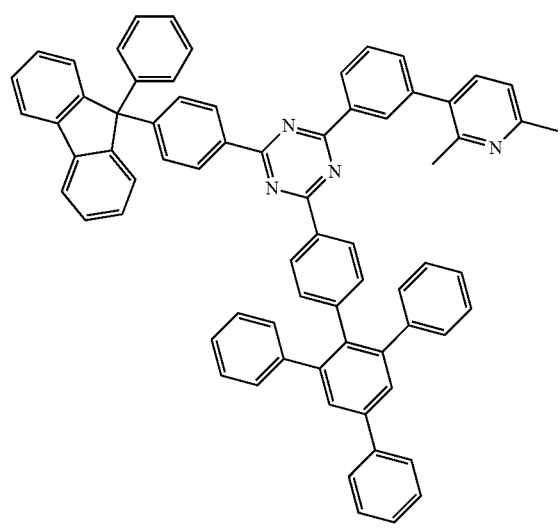
87
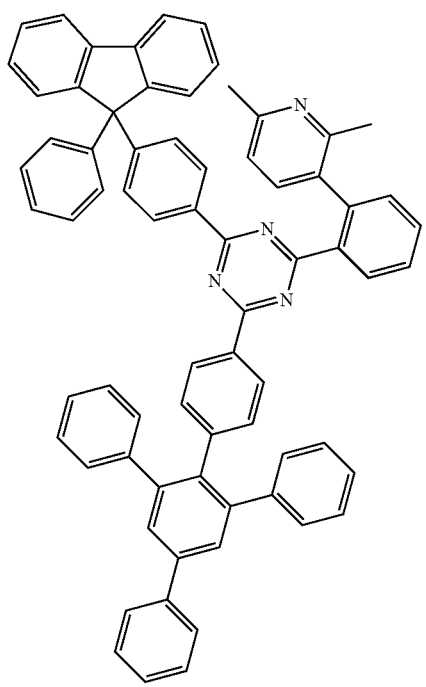
88
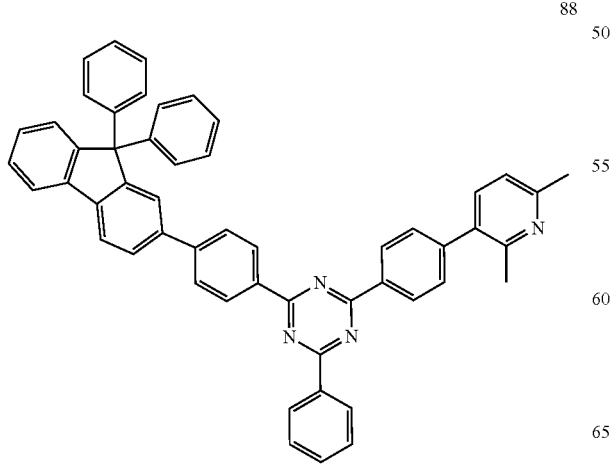
89
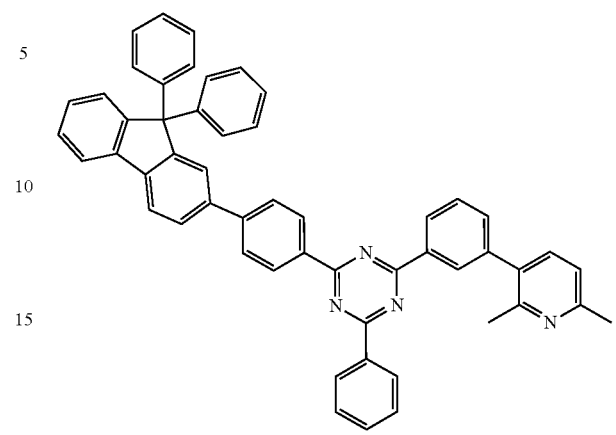
90
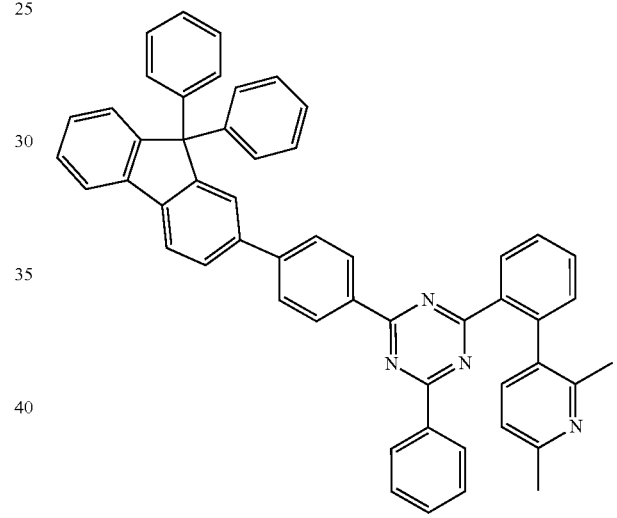
91
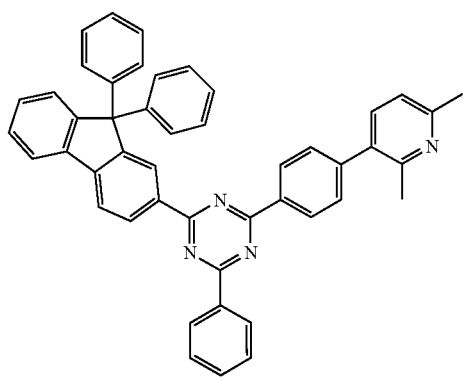

75
-continued
92
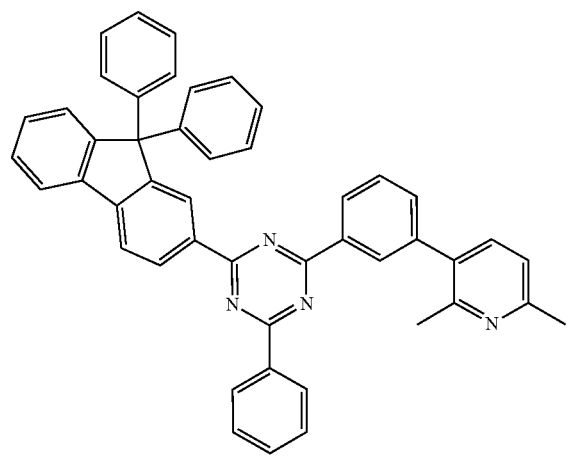
93
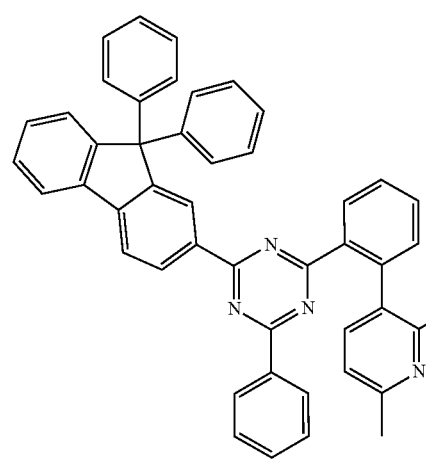
94
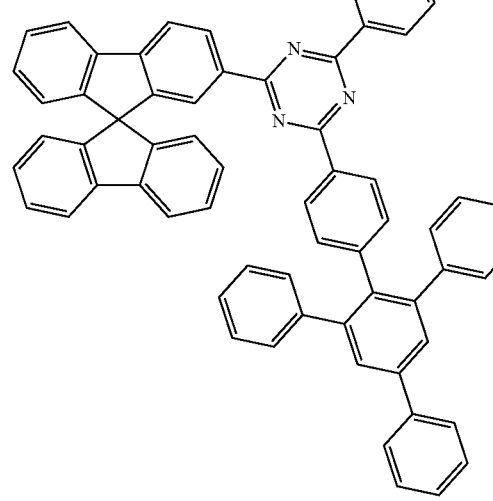
76
-continued
95
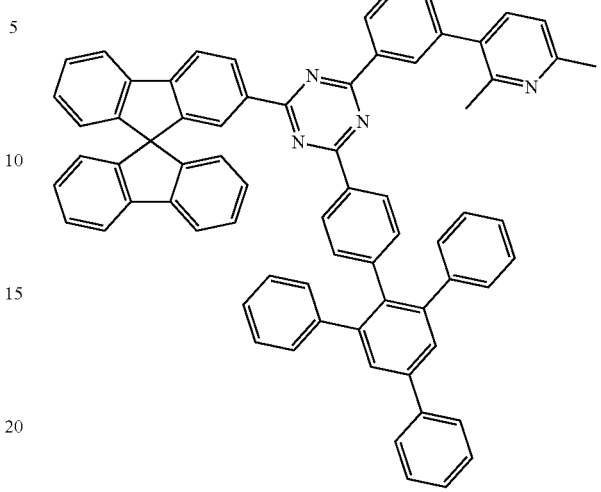
96
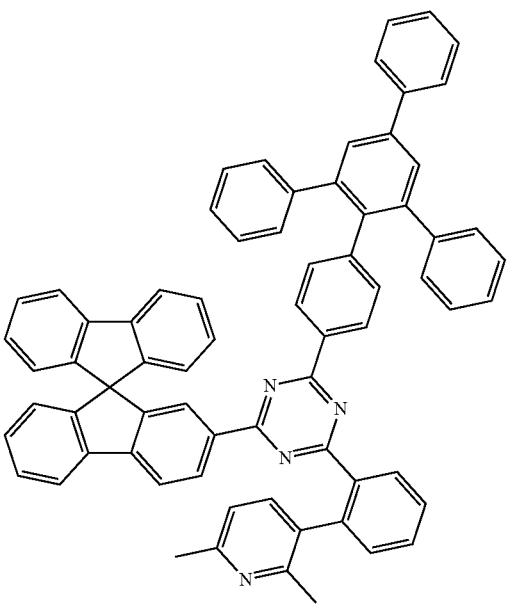
97
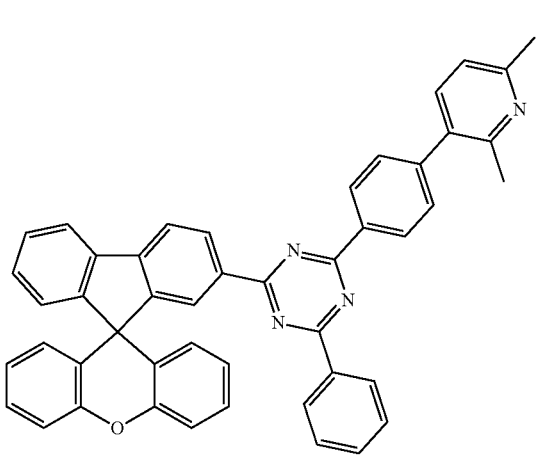

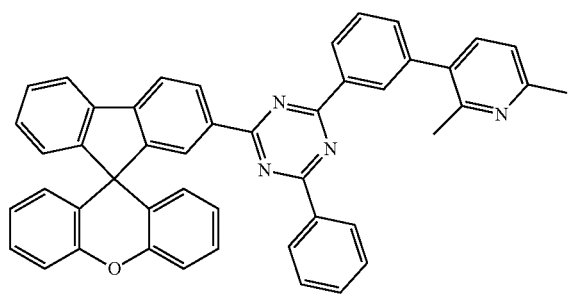
98
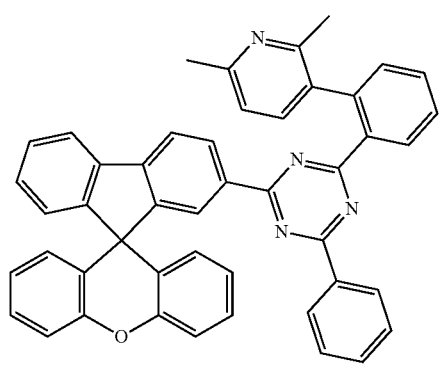
99
100
101
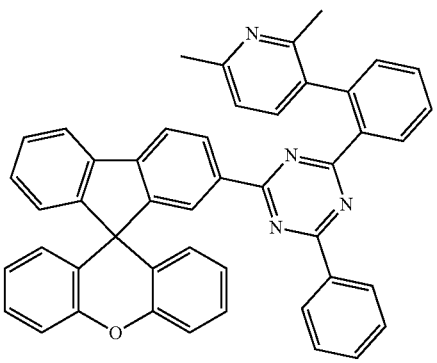
102
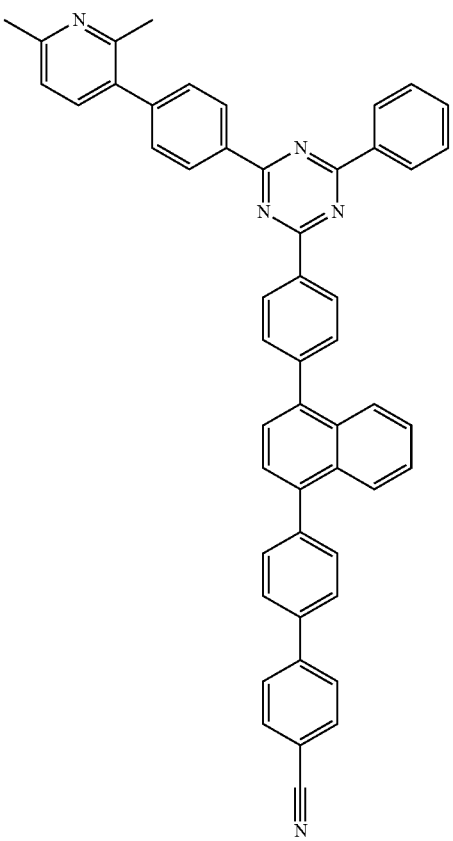
103

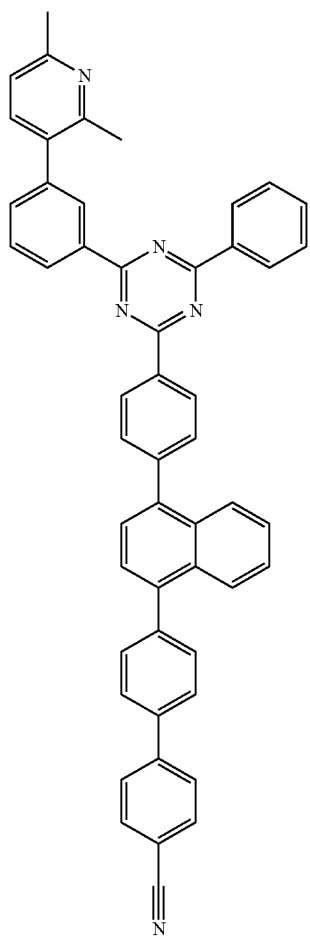
104
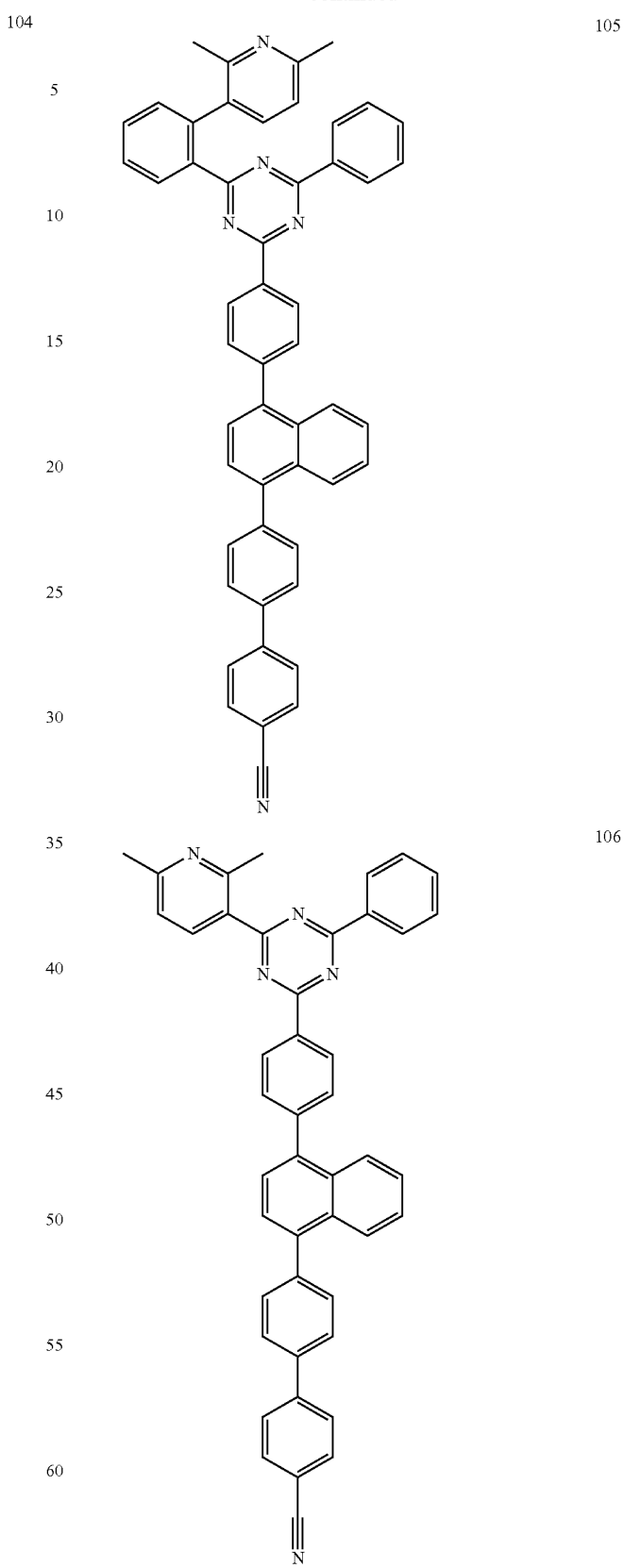
105
106

107
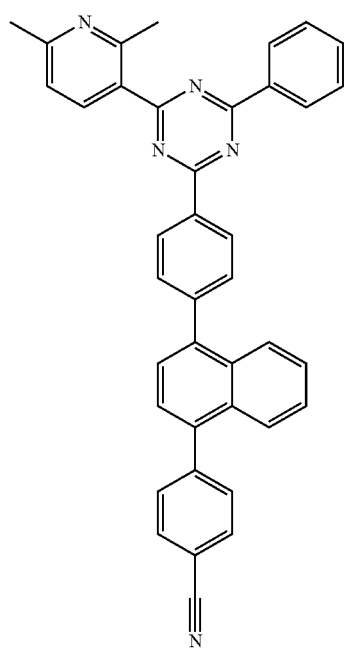
108
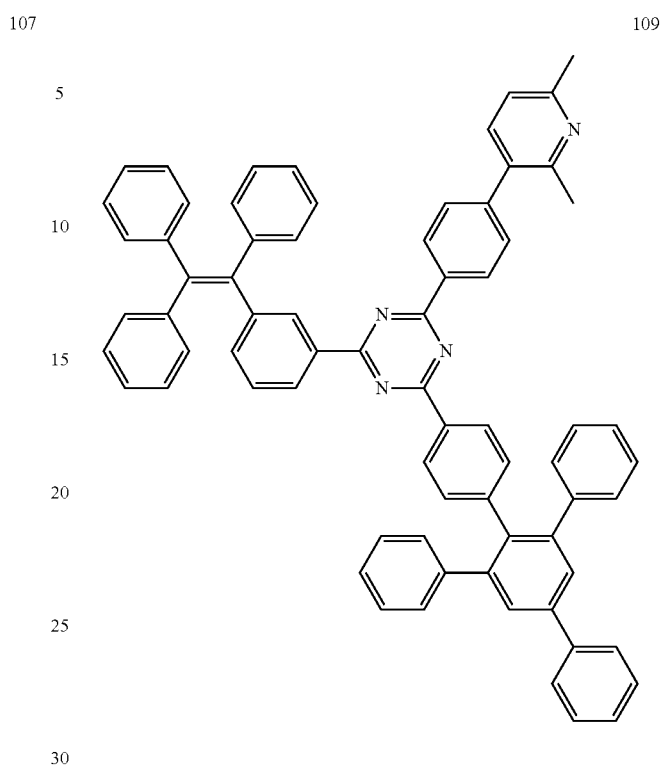
109
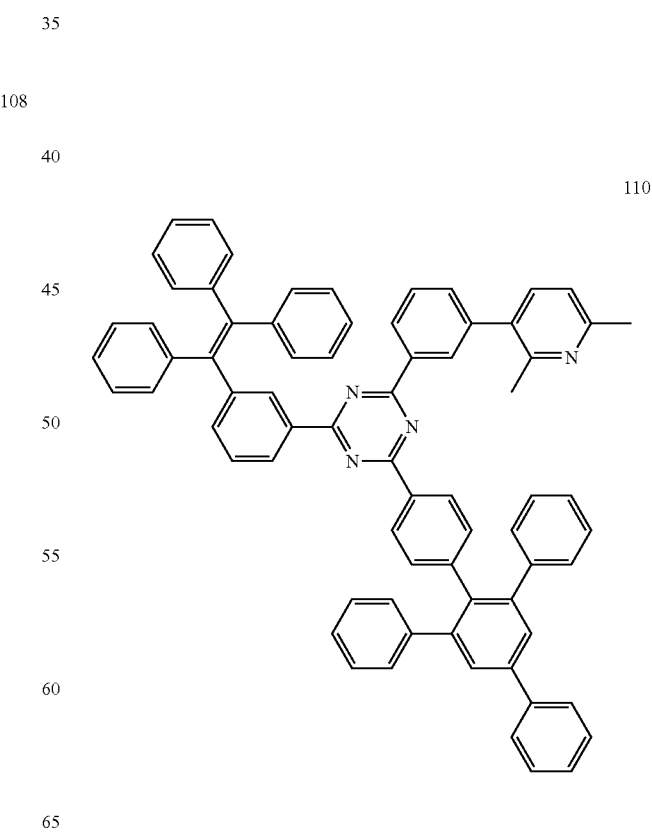
110

111
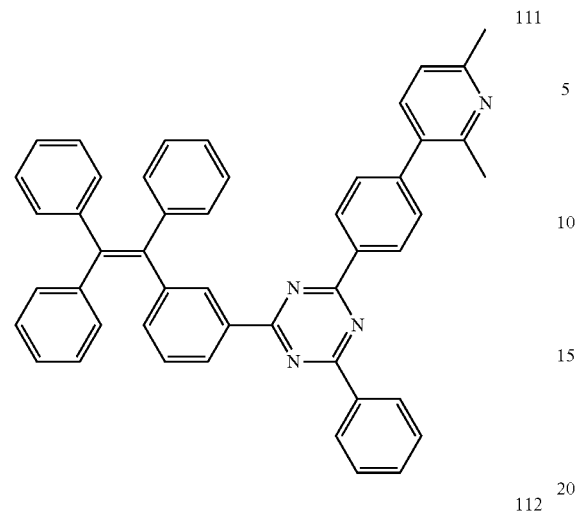
112
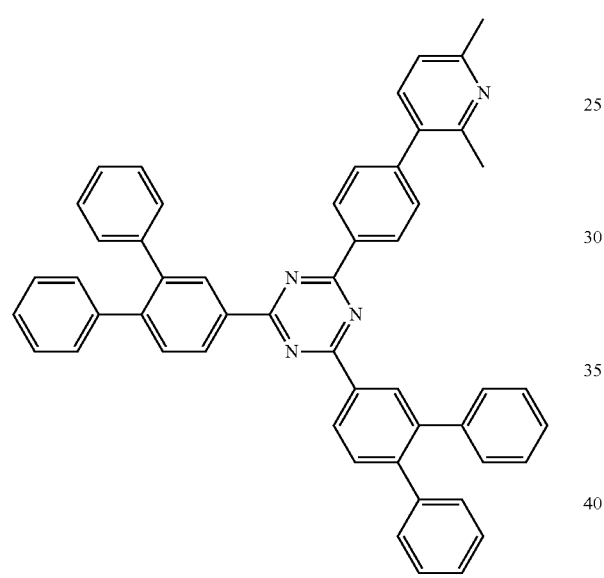
113
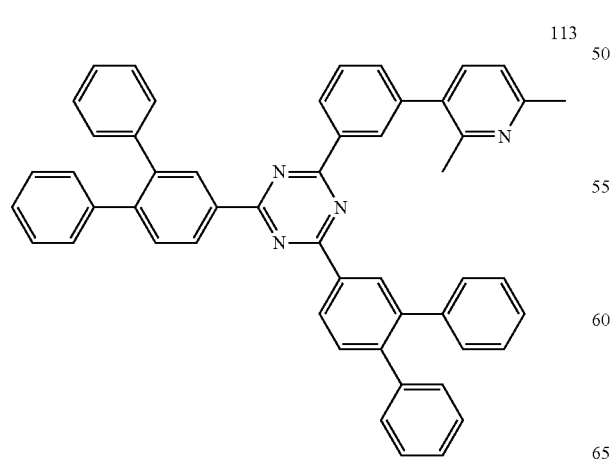
114
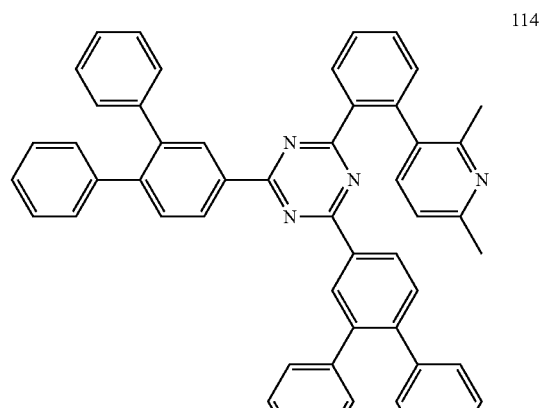
115
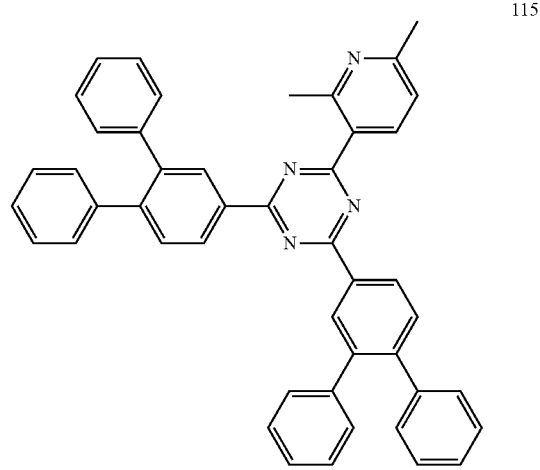
116
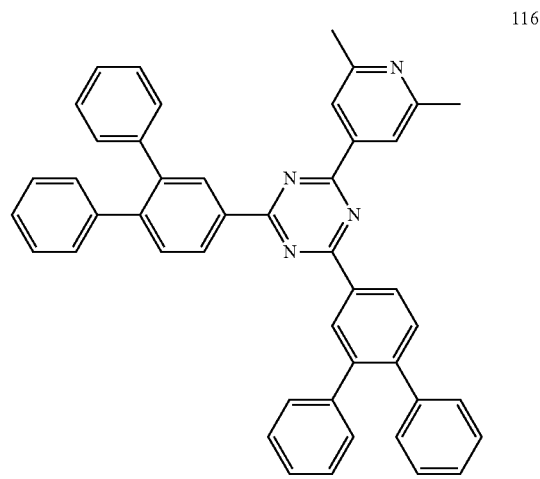

117
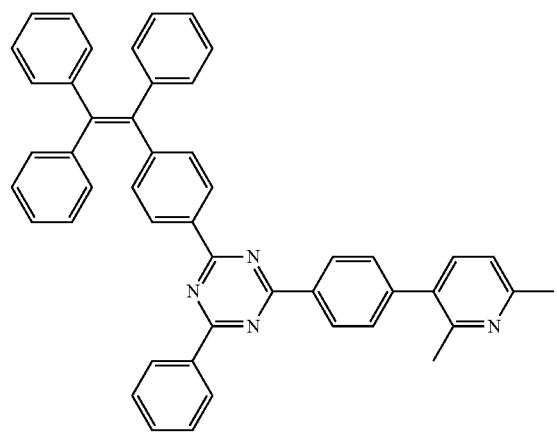
118
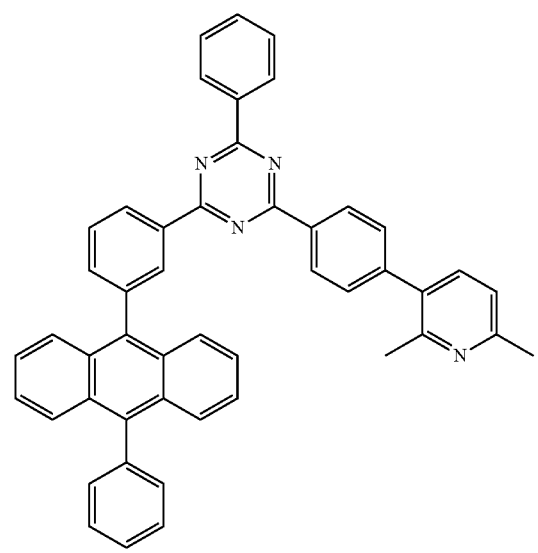
119
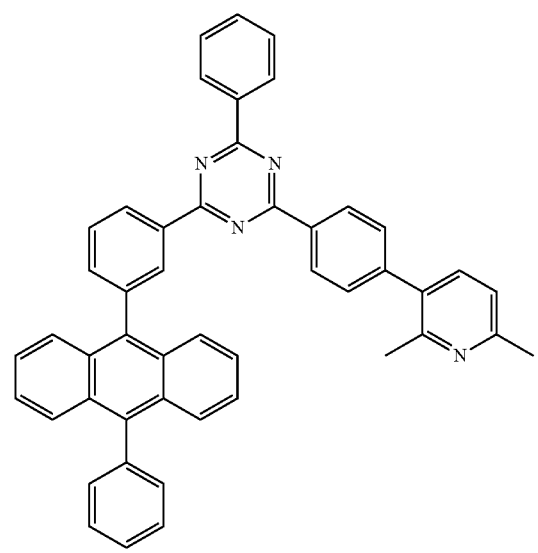
120
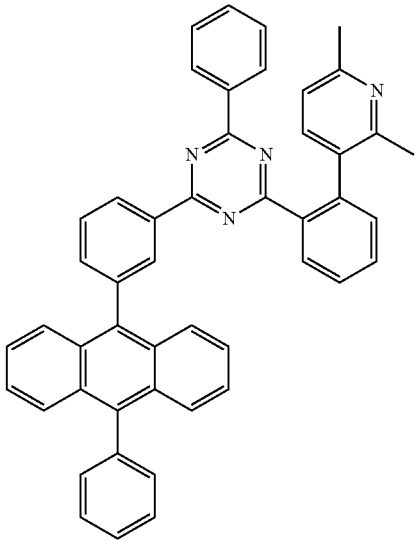
121
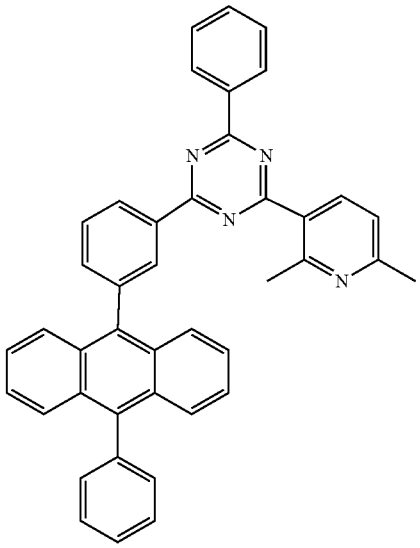
122
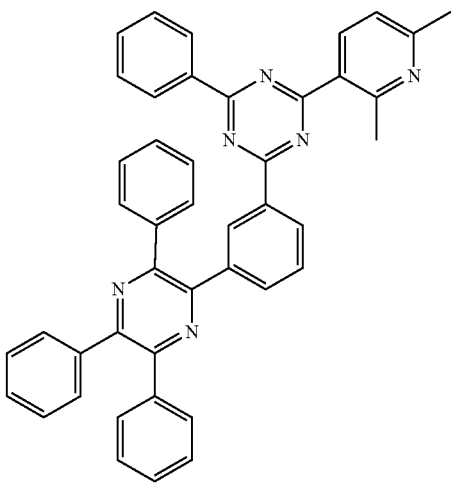

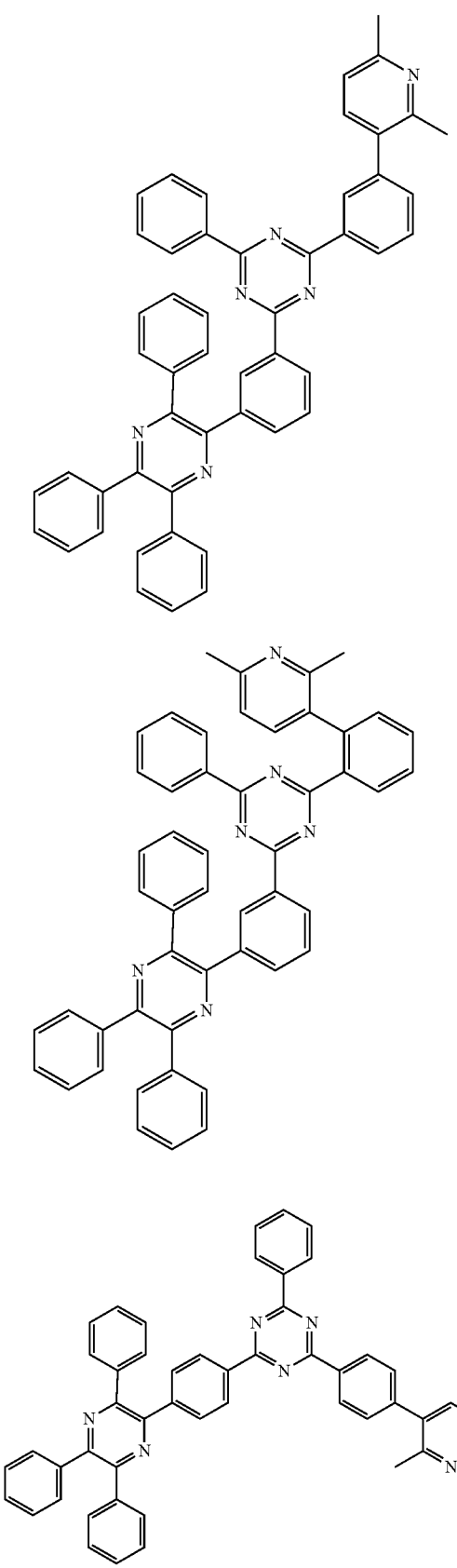

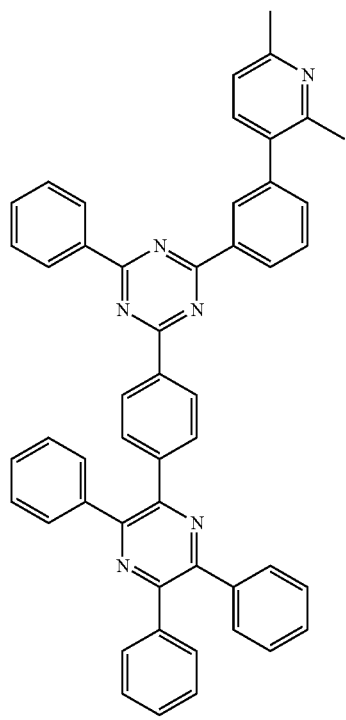
128
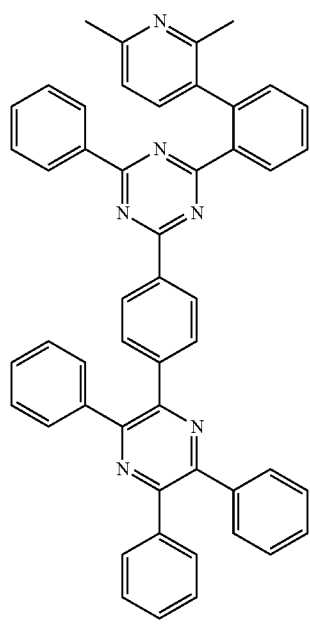
129
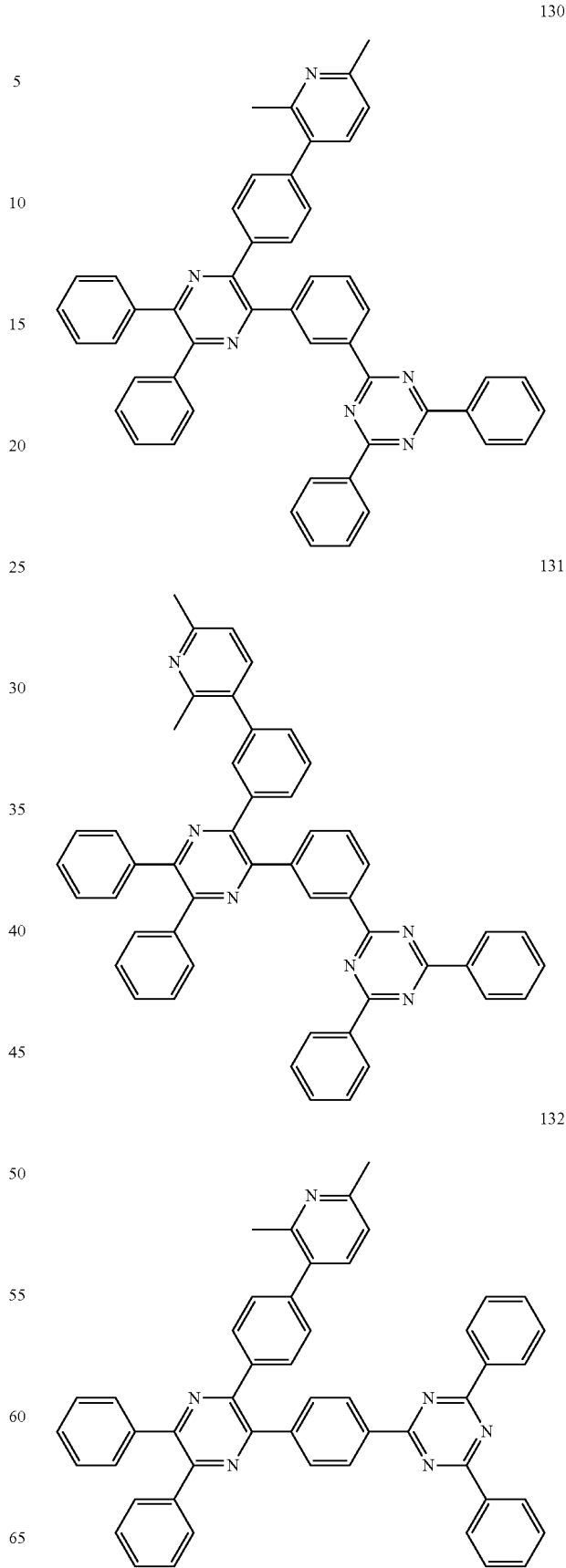
130
131
132

133
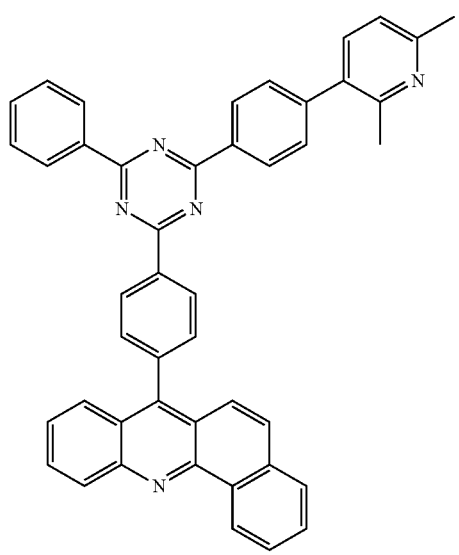
134
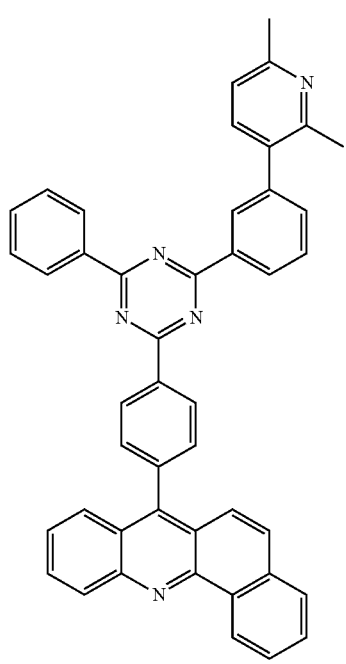
135
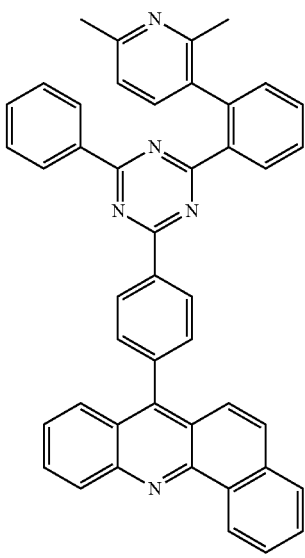
136
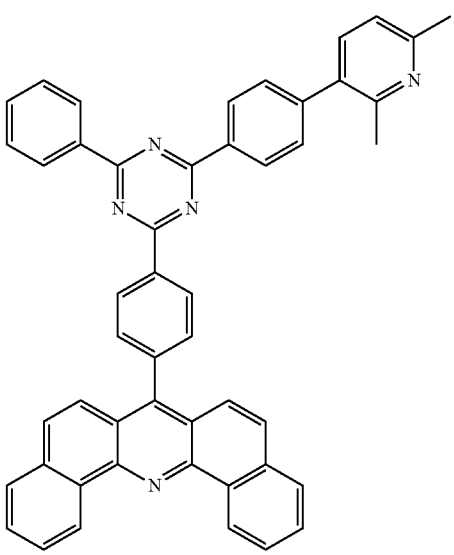

137
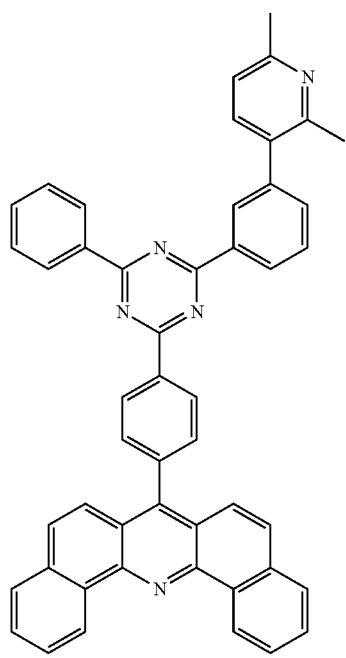
138
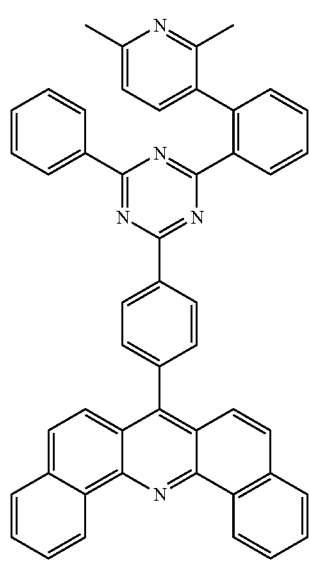
139
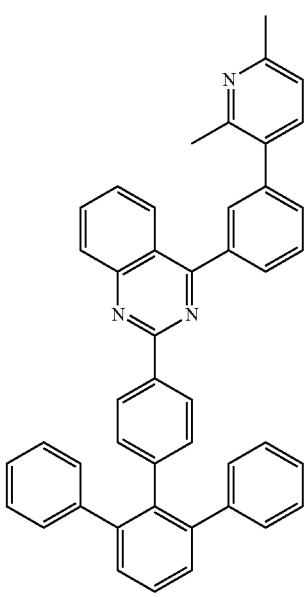 [SMILES: Cc1ccc(-c2cccc(-c3nc(-c4ccc(-c5c(-c6ccccc6)cccc5-c5ccccc5)cc4)nc4ccccc34)c2)c(C)n1]
140
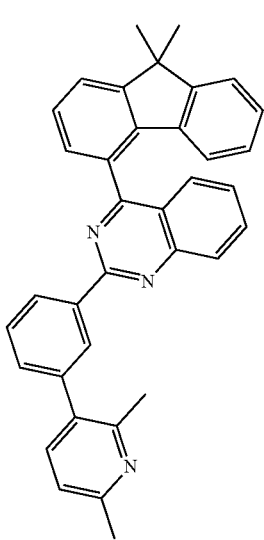

141
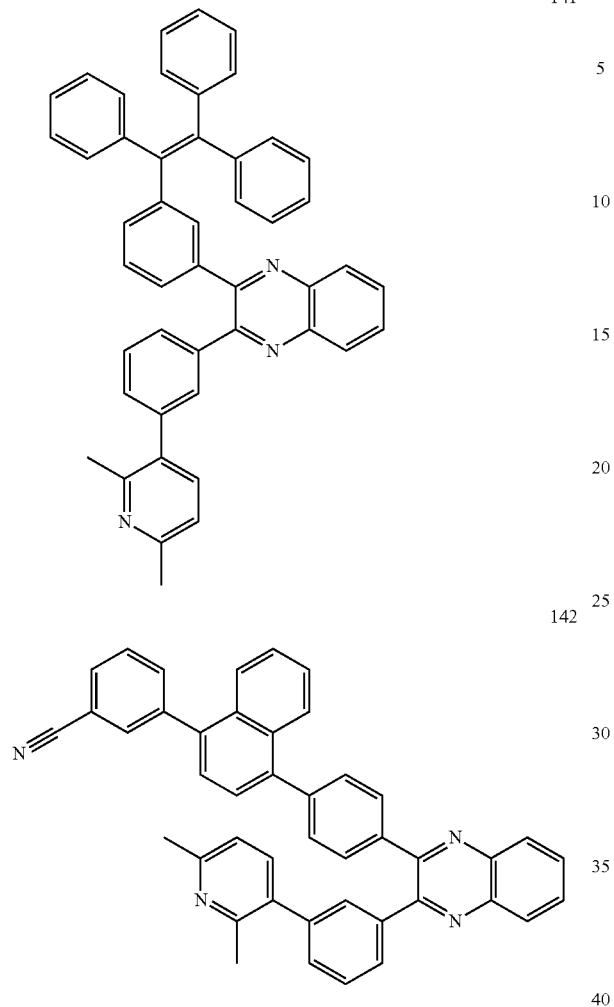
142
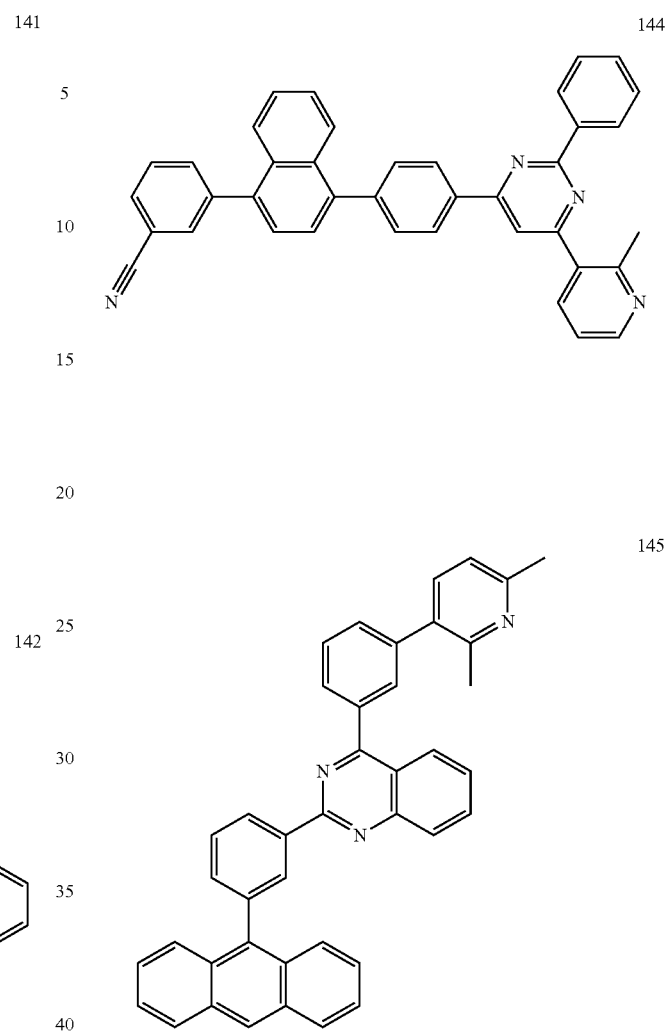
144
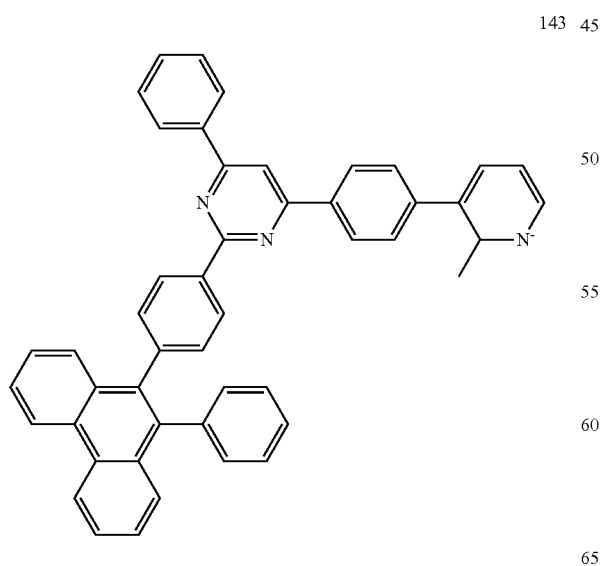
145
143
146
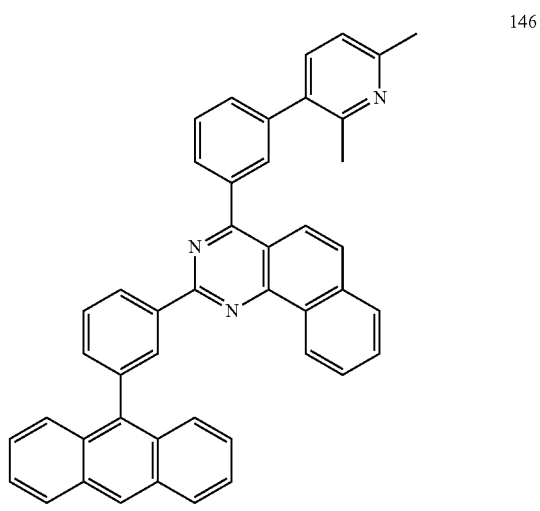

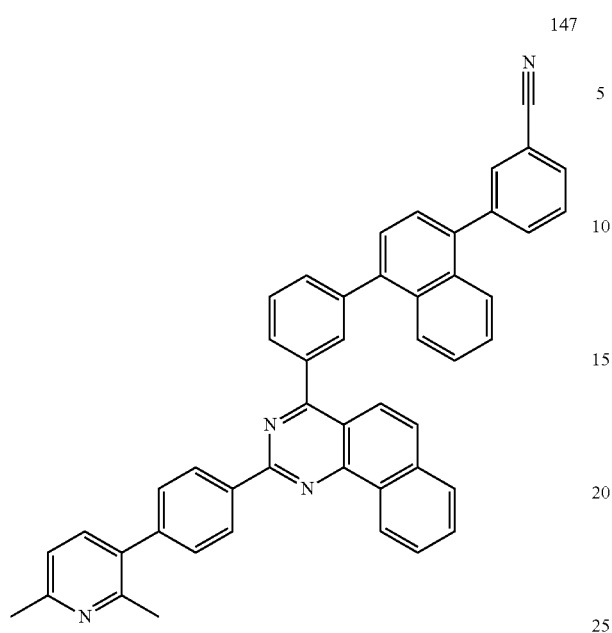
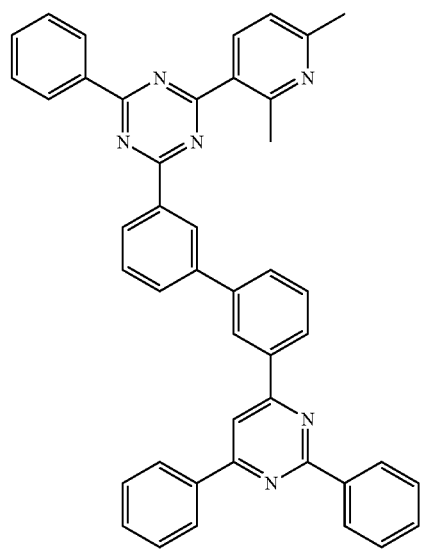
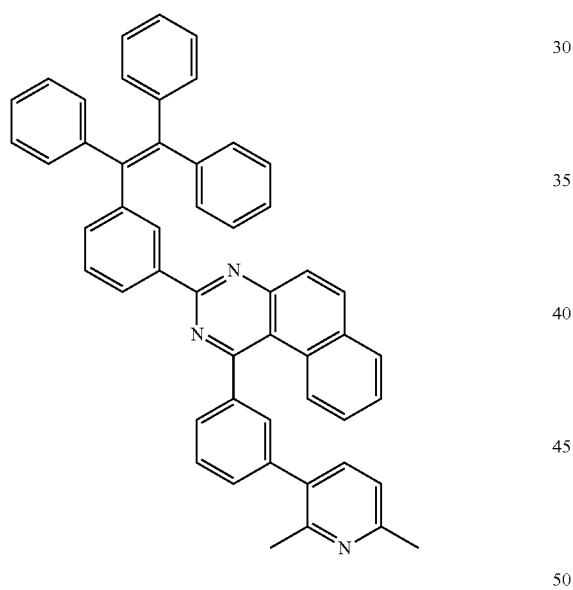
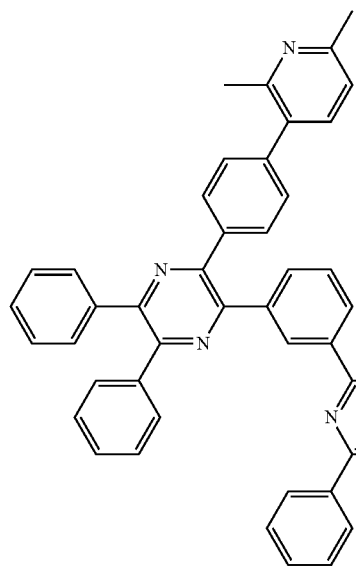
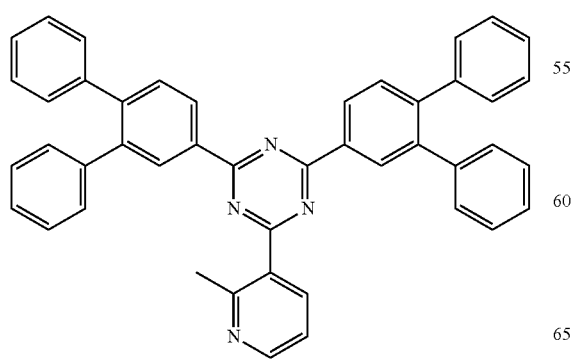

149
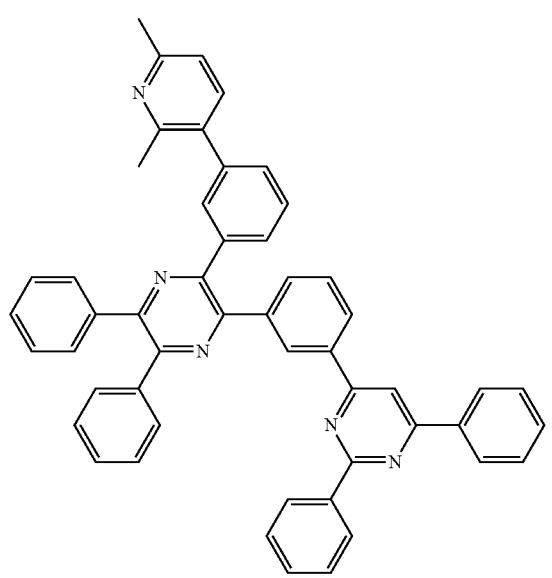
150
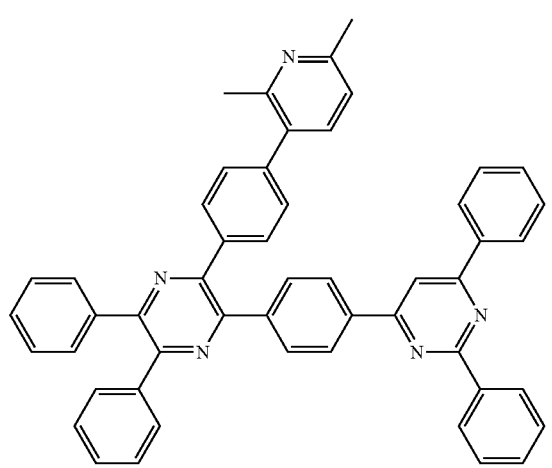
151
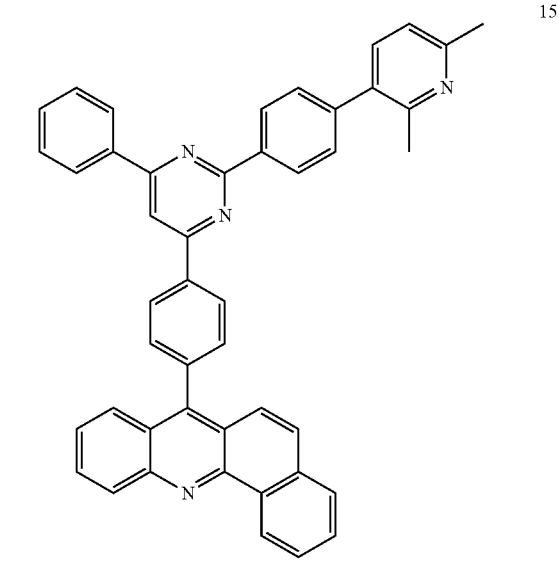
152
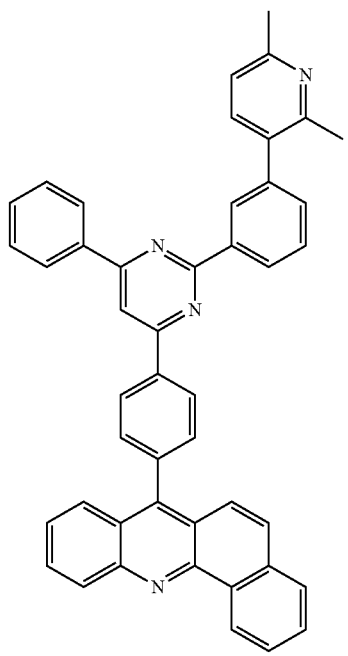
153
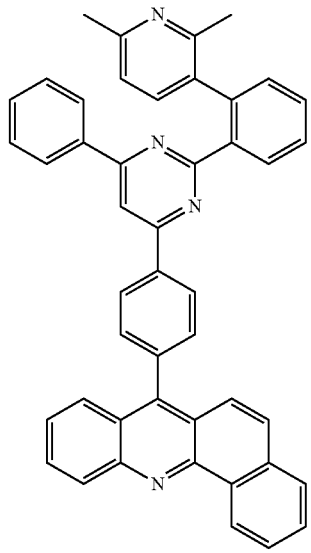

101
-continued
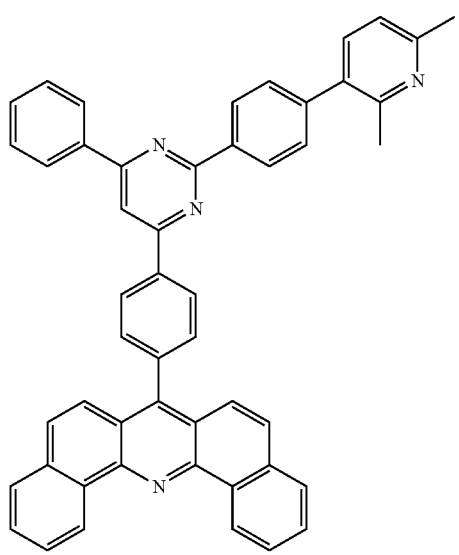
154
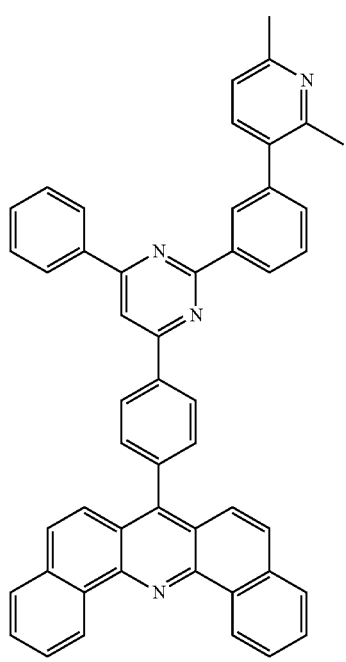
155
102
-continued
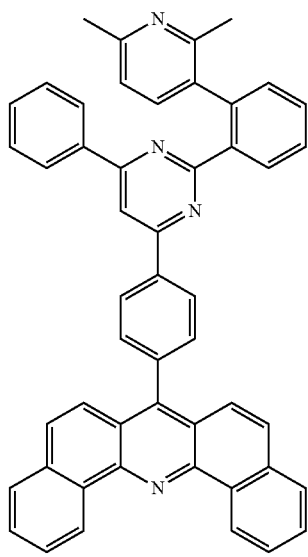
156
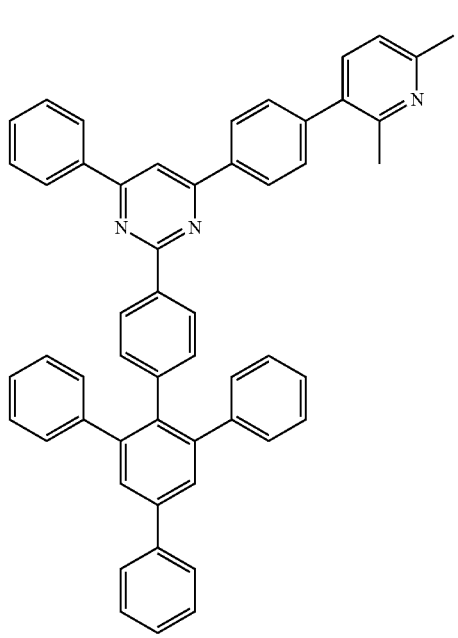
157

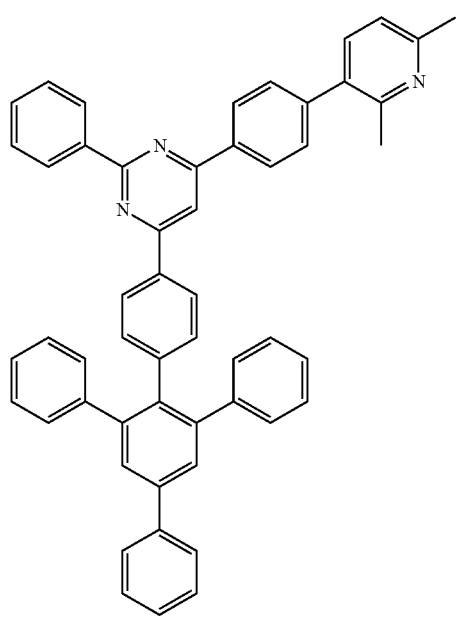
158
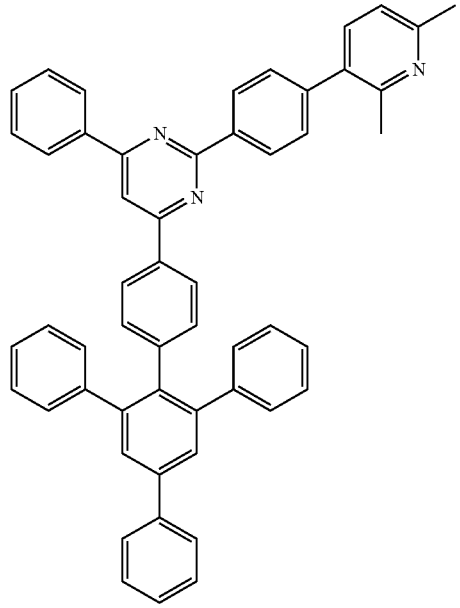
159
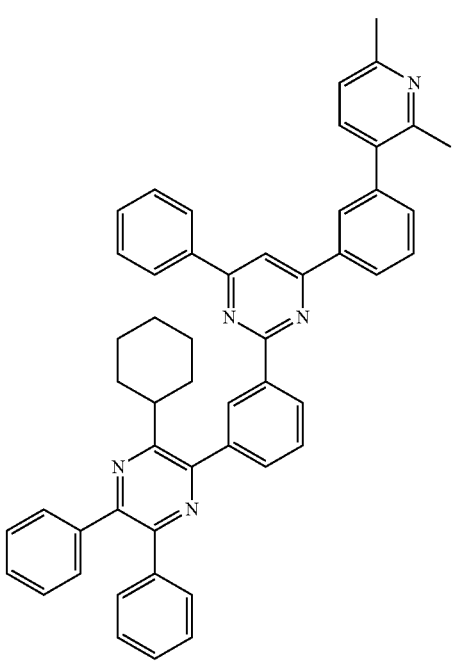
160
161

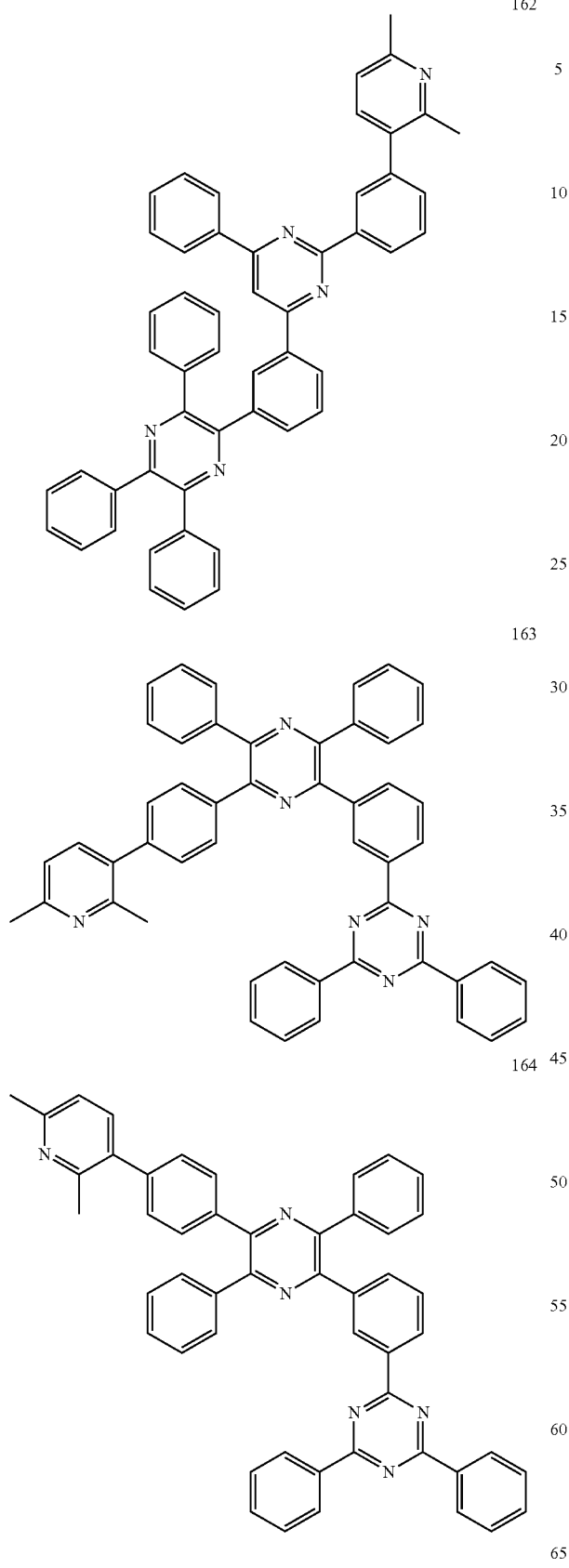
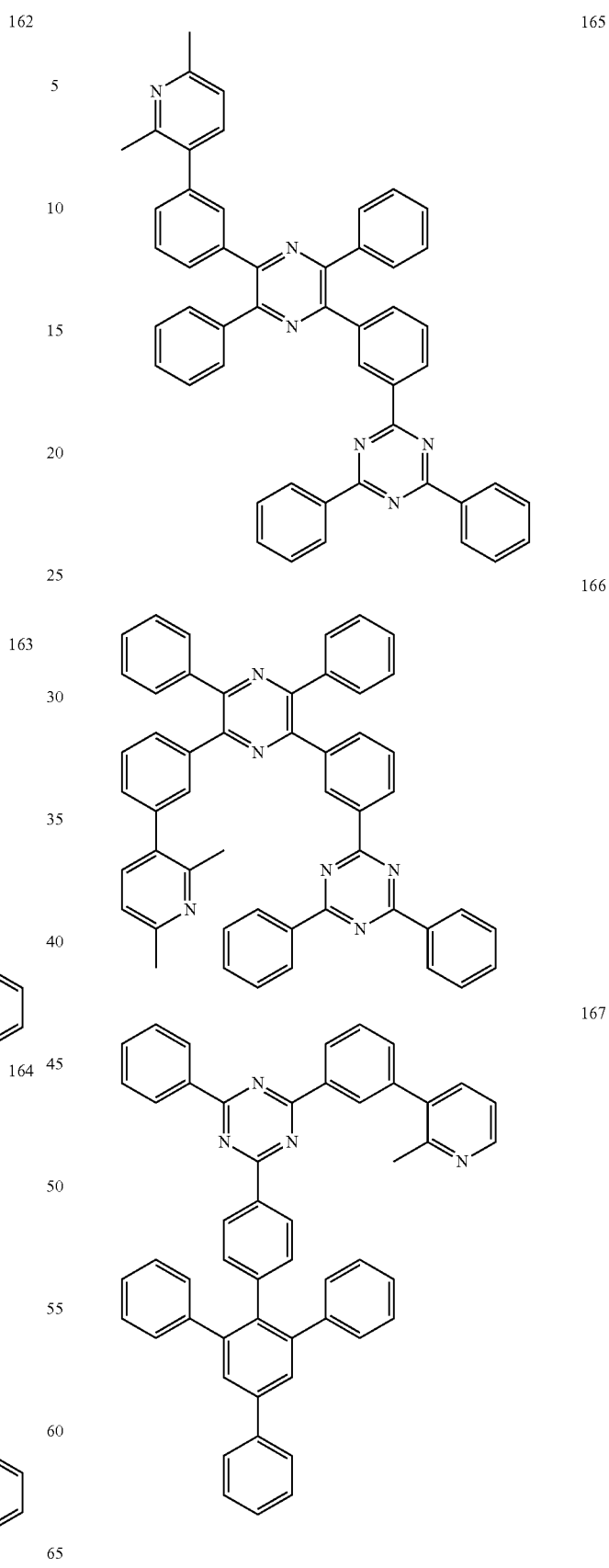

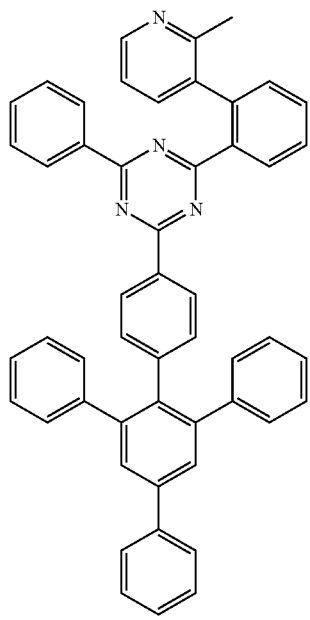
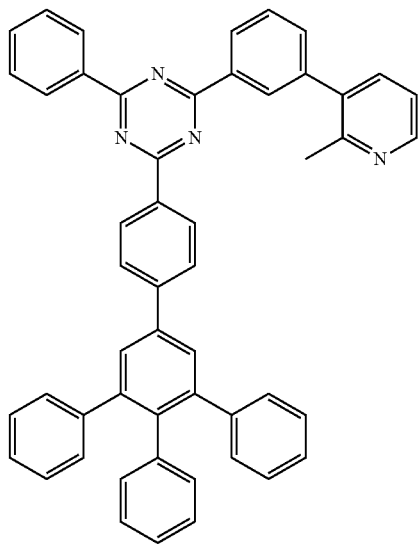

172
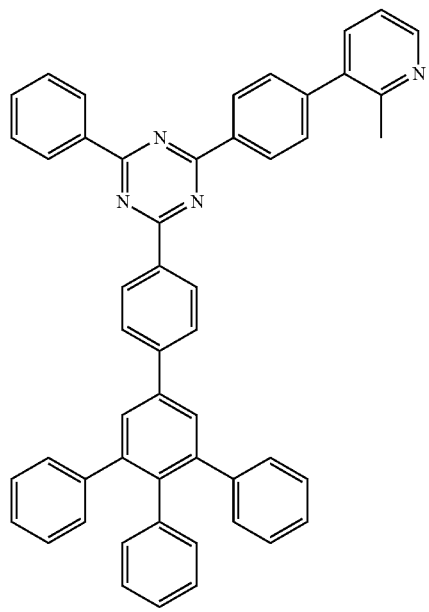
173
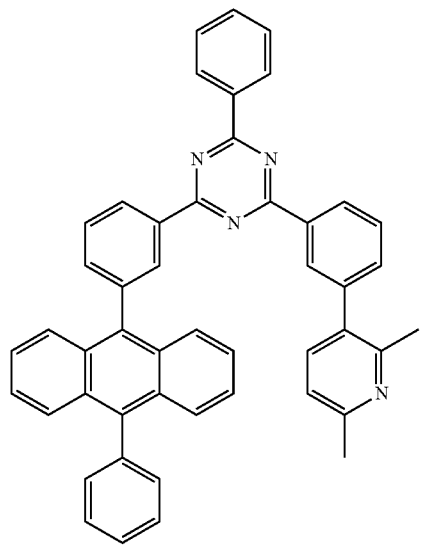
174
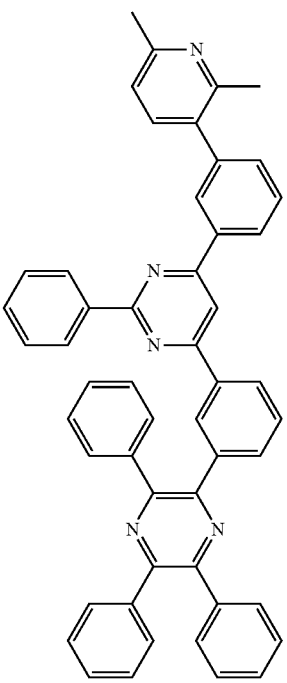
175
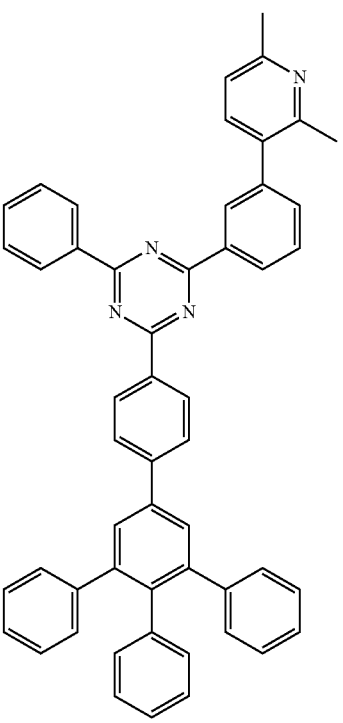

176
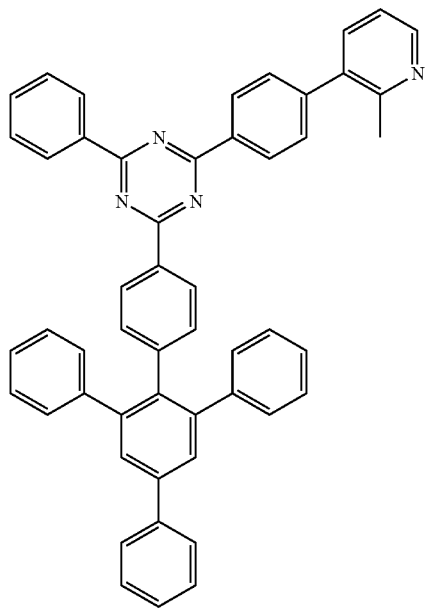
177
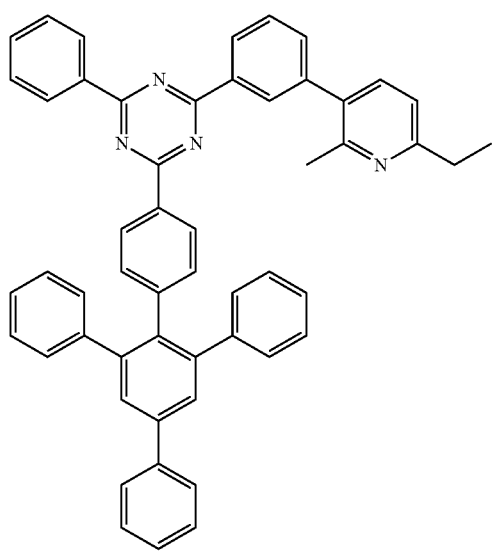
178
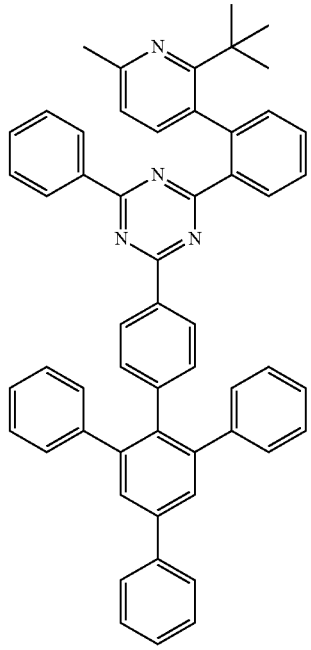
179
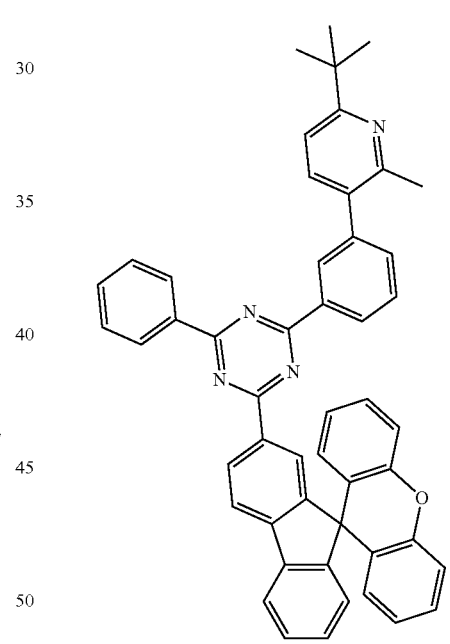
180
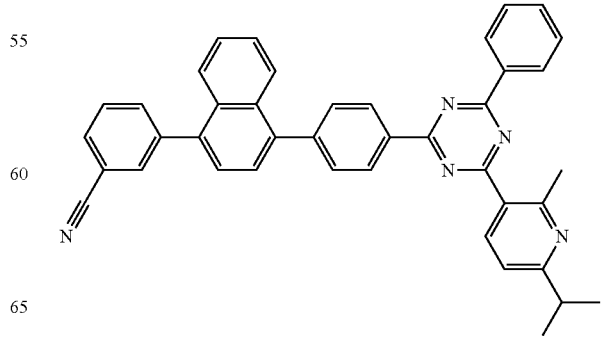

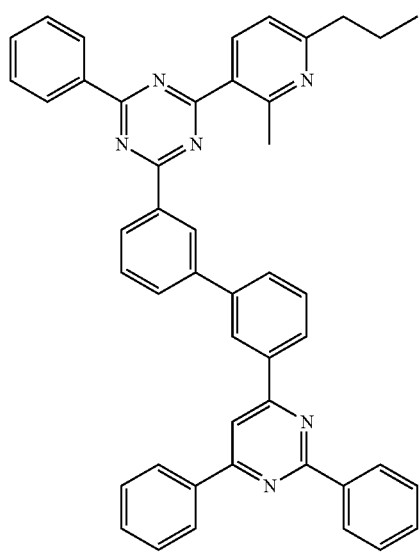
181
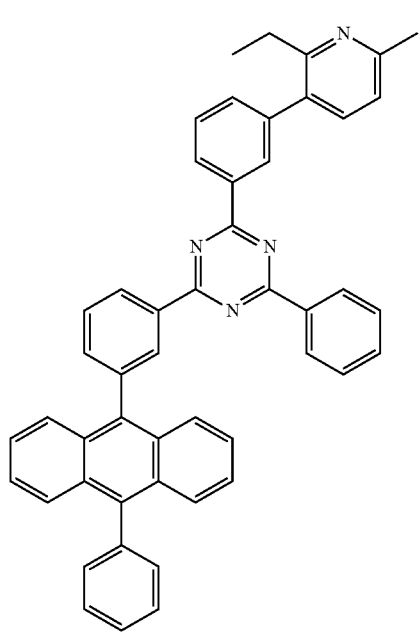
182
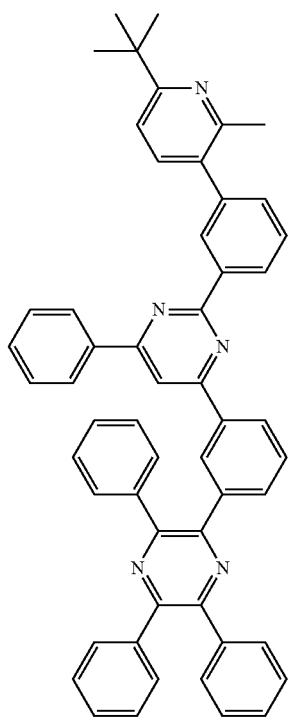
183
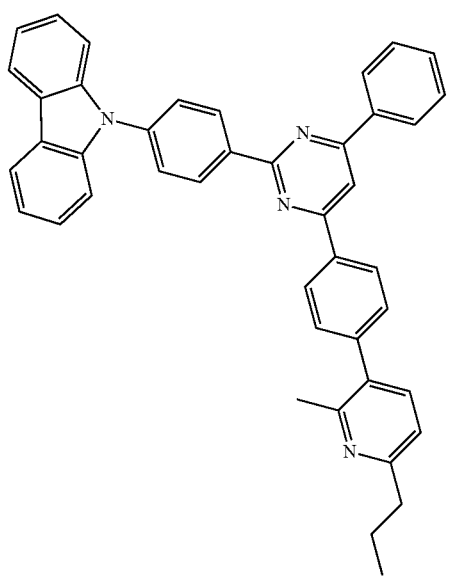
184

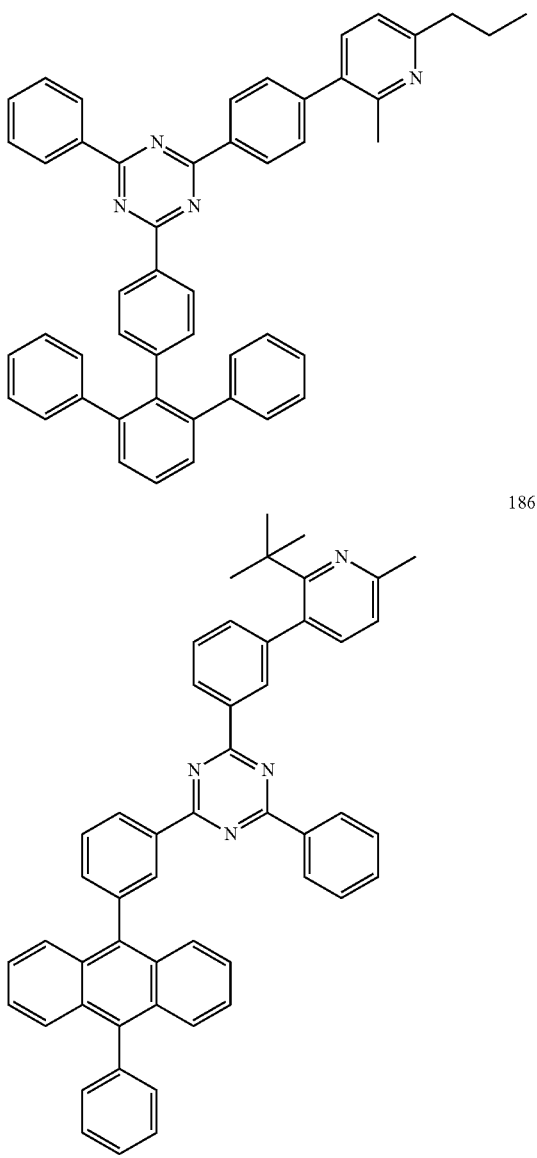

The object is farther achieved by an organic semiconducting layer comprising the compound of Formula (I) as defined herein.

The organic semiconducting layer comprising the compound of Formula (I) as defined herein may further comprise a metal, a metal salt or an organic alkali metal complex, alternatively an alkali metal complex, alternatively LiQ or metal borate.

The organic semiconducting layer may be non-emissive.

The object is further achieved by an organic electronic device comprising the organic semiconducting layer as defined herein.

The organic electronic device may further comprise an anode, a cathode and at least one emission layer, wherein the organic semiconducting layer comprising the compound of Formula (I) is arranged between the at least one emission layer and the cathode.

Alternatively, the organic semiconducting layer comprising the compound of Formula (I) may be arranged between an auxiliary electron transport layer and the cathode. The auxiliary electron transport layer may also be described as hole blocking layer.

Alternatively, the organic semiconducting layer comprising the compound of Formula (I) may be arranged between a first and a second emission layer.

The organic electronic device may be an organic light emitting device.

The object is further achieved by a display device comprising the organic electronic device as defined herein.

Finally, the object is achieved by a lighting device comprising the organic electronic device as defined herein.

Further Layers

In accordance with the invention, the organic electronic device may comprise, besides the layers already mentioned above, further layers. Exemplary embodiments of respective layers are described in the following:

Substrate

The substrate may be any substrate that is commonly used in manufacturing of, electronic devices, such as organic light-emitting diodes. If light is to be emitted through the substrate, the substrate shall be a transparent or semitransparent material, for example a glass substrate or a transparent plastic substrate. If light is to be emitted through the top surface, the substrate may be both a transparent as well as a non-transparent material, for example a glass substrate, a plastic substrate, a metal substrate or a silicon substrate.

Anode Electrode

Either a first electrode or a second electrode comprised in the inventive organic electronic device may be an anode electrode. The anode electrode may be formed by depositing or sputtering a material that is used to form the anode electrode. The material used to form the anode electrode may be a high work-function material, so as to facilitate hole injection. The anode material may also be selected from a low work function material (i.e. aluminum). The anode electrode may be a transparent or reflective electrode. Transparent conductive oxides, such as indium tin oxide (ITO), indium zinc oxide (IZO), tin-dioxide (SnO2), aluminum zinc oxide (AlZO) and zinc oxide (ZnO), may be used to form the anode electrode. The anode electrode may also be formed using metals, typically silver (Ag), gold (Au), or metal alloys.

Hole Injection Layer

A hole injection layer (HIL) may be formed on the anode electrode by vacuum deposition, spin coating, printing, casting, slot-die coating, Langmuir-Blodgett (LB) deposition, or the like. When the HIL is formed using vacuum deposition, the deposition conditions may vary according to the compound that is used to form the HIL, and the desired structure and thermal properties of the HIL. In general, however, conditions for vacuum deposition may include a deposition temperature of 100° C. to 500° C., a pressure of 10-8 to 10-3 Torr (1 Torr equals 133.322 Pa), and a deposition rate of 0.1 to 10 nm/sec.

When the HIL is formed using spin coating or printing, coating conditions may vary according to the compound that is used to form the HIL, and the desired structure and thermal properties of the HIL. For example, the coating conditions may include a coating speed of about 2000 rpm to about 5000 rpm, and a thermal treatment temperature of about 80° C. to about 200° C. Thermal treatment removes a solvent after the coating is performed.

The HIL may be formed of any compound that is commonly used to form a HIL. Examples of compounds that may be used to form the HIL include a phthalocyanine compound, such as copper phthalocyanine (CuPc), 4,4',4"- tris (3-methylphenylphenylamino) triphenylamine (m-MT-DATA), TDATA, 2T-NATA, polyaniline/dodecylbenzene-sulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

The HIL may comprise or consist of p-type dopant and the p-type dopant may be selected from tetrafluoro-tetracyano-quinonedimethane (F4TCNQ), 2,2'-(perfluoronaphthalen-2,6-diylidene) dimalononitrile or 2,2',2"-(cyclopropane-1,2,3-triylidene)tris(2-(p-cyanotetrafluorophenyl)acetonitrile) but not limited hereto. The HIL may be selected from a hole-transporting matrix compound doped with a p-type dopant. Typical examples of known doped hole transport materials are: copper phthalocyanine (CuPc), which HOMO level is approximately −5.2 eV, doped with tetrafluoro-tetracyano-quinonedimethane (F4TCNQ), which LUMO level is about −5.2 eV; zinc phthalocyanine (ZnPc) (HOMO=−5.2 eV) doped with F4TCNQ; α-NPD (N,N'-Bis(naphthalen-1-yl)-N,N'-bis(phenyl)-benzidine) doped with F4TCNQ. α-NPD doped with 2,2'-(perfluoronaphthalen-2,6-diylidene) dima-lononitrile. The p-type dopant concentrations can be selected from 1 to 20 wt.-%, more preferably from 3 wt.-% to 10 wt.-%.

The thickness of the HIL may be in the range from about 1 nm to about too nm, and for example, from about 1 nm to about 25 nm. When the thickness of the HIL is within this range, the HIL may have excellent hole injecting character-istics, without a substantial penalty in driving voltage.

Hole Transport Layer

A hole transport layer (HTL) may be formed on the HIL by vacuum deposition, spin coating, slot-die coating, print-ing, casting, Langmuir-Blodgett (LB) deposition, or the like. When the HTL is formed by vacuum deposition or spin coating, the conditions for deposition and coating may be similar to those for the formation of the HIL. However, the conditions for the vacuum or solution deposition may vary, according to the compound that is used to form the HTL.

The HTL may be formed of any compound that is commonly used to form a HTL. Compounds that can be suitably used are disclosed for example in Yasuhiko Shirota and Hiroshi Kageyama, Chem. Rev. 2007, 107, 953-1010 and incorporated by reference. Examples of the compound that may be used to form the HTL are: carbazole derivatives, such as N-phenylcarbazole or polyvinylcarbazole; benzidine derivatives, such as N,N-bis(3-methylphenyl)-N,N'-diphe-nyl-[1,1-biphenyl]-4,4'-diamine (TPD), or N,N'-di(naphtha-len-1-yl)-N,N'-diphenyl benzidine (alpha-NPD); and triph-enylamine-based compound, such as 4,4',4"-tris(N-carbazolyl)triphenylamine (TCTA). Among these compounds, TCTA can transport holes and inhibit excitons from being diffused into the EML.

The thickness of the HTL may be in the range of about 5 nm to about 250 nm, preferably, about 10 nm to about 200 nm, further about 20 nm to about 190 nm, further about 40 nm to about 180 nm, further about 60 nm to about 170 nm, further about 80 nm to about 160 nm, further about 100 nm to about 160 nm, further about 120 nm to about 140 nm. A preferred thickness of the HTL may be 170 nm to 200 nm.

When the thickness of the HTL is within this range, the HTL may have excellent hole transporting characteristics, without a substantial penalty in driving voltage.

Electron Blocking Layer

The function of an electron blocking layer (EBL) is to prevent electrons from being transferred from an emission layer to the hole transport layer and thereby confine elec-trons to the emission layer. Thereby, efficiency, operating voltage and/or lifetime are improved. Typically, the electron blocking layer comprises a triarylamine compound. The triarylamine compound may have a LUMO level closer to vacuum level than the LUMO level of the hole transport layer. The electron blocking layer may have a HOMO level that is further away from vacuum level compared to the HOMO level of the hole transport layer. The thickness of the electron blocking layer may be selected between 2 and 20 nm.

If the electron blocking layer has a high triplet level, it may also be described as triplet control layer.

The function of the triplet control layer is to reduce quenching of triplets if a phosphorescent green or blue emission layer is used. Thereby, higher efficiency of light emission from a phosphorescent emission layer can be achieved. The triplet control layer is selected from triarylam-ine compounds with a triplet level above the triplet level of the phosphorescent emitter in the adjacent emission layer. Suitable compounds for the triplet control layer, in particular the triarylamine compounds, are described in EP 2 722 908 A1.

Emission Layer (EML)

The EML may be formed on the HTL by vacuum depo-sition, spin coating, slot-die coating, printing, casting, LB deposition, or the like. When the EML is formed using vacuum deposition or spin coating, the conditions for depo-sition and coating may be similar to those for the formation of the HIL. However, the conditions for deposition and coating may vary, according to the compound that is used to form the EML.

It may be provided that the emission layer does not comprise the compound of Formula (I).

The emission layer (EML) may be formed of a combi-nation of a host and an emitter dopant. Example of the host are Alq3, 4,4'-N,N'-dicarbazole-biphenyl (CBP), poly(n-vi-nylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBI), 3-tert-butyl-9,10-di-2-naphthylanthracenee (TBADN), distyrylarylene (DSA) and bis(2-(2-hydroxyphenyl)benzo-thiazolate)zinc (Zn(BTZ)2).

The emitter dopant may be a phosphorescent or fluores-cent emitter. Phosphorescent emitters and emitters which emit light via a thermally activated delayed fluorescence (TADF) mechanism may be preferred due to their higher efficiency. The emitter may be a small molecule or a polymer.

Examples of red emitter dopants are PtOEP, Ir(piq)3, and Btp2Ir(acac), but are not limited thereto. These compounds are phosphorescent emitters, however, fluorescent red emit-ter dopants could also be used.

Examples of phosphorescent green emitter dopants are Ir(ppy)3 (ppy=phenylpyridine), Ir(ppy)2(acac), Ir(mpyp)3.

Examples of phosphorescent blue emitter dopants are F2Irpic, (F2ppy)2Ir(tmd) and Ir(dfppz)3 and ter-fluorene. 4.4-bis(4-diphenyl amiostyryl)biphenyl (DPAVBi), 2,5,8, 11-tetra-tert-butyl perylene (TBPe) are examples of fluores-cent blue emitter dopants.

The amount of the emitter dopant may be in the range from about 0.01 to about 50 parts by weight, based on 100 parts by weight of the host. Alternatively, the emission layer may consist of a light-emitting polymer. The EML may have a thickness of about 10 nm to about 100 nm, for example, from about 20 nm to about 60 nm. When the thickness of the EML is within this range, the EML may have excellent light emission, without a substantial penalty in driving voltage.

Hole Blocking Layer (HBL)

A hole blocking layer (HBL) may be formed on the EML, by using vacuum deposition, spin coating, slot-die coating, printing, casting, LB deposition, or the like, in order to prevent the diffusion of holes into the ETL. When the EML comprises a phosphorescent dopant, the HBL may have also a triplet exciton blocking function. The hole blocking layer may be the inventive organic semiconducting layer comprising or consisting of the inventive compound represented by the general Formula (I) as defined above.

The HBL may also be named auxiliary ETL or a-ETL.

When the HBL is formed using vacuum deposition or spin coating, the conditions for deposition and coating may be similar to those for the formation of the HIL. However, the conditions for deposition and coating may vary, according to the compound that is used to form the HBL. Any compound that is commonly used to form a HBL may be used. Examples of compounds for forming the HBL include xadiazole derivatives, triazole derivatives, and phenanthroline derivatives.

The HBL may have a thickness in the range from about 5 nm to about 100 nm, for example, from about 10 nm to about 30 nm. When the thickness of the HBL is within this range, the HBL may have excellent hole-blocking properties, without a substantial penalty in driving voltage.

Electron Transport Layer (ETL)

The OLED according to the present invention may comprise an electron transport layer (ETL). In accordance with one embodiment of the invention, the electron transport layer may be the inventive organic semiconducting layer comprising the inventive compound represented by the general Formula (I) as defined herein.

According to various embodiments the OLED may comprise an electron transport layer or an electron transport layer stack comprising at least a first electron transport layer (ETL-1) and at least a second electron transport layer (ETL-2).

By suitably adjusting energy levels of particular layers of the ETL, the injection and transport of the electrons may be controlled, and the holes may be efficiently blocked. Thus, the OLED may have long lifetime.

The electron transport layer of the organic electronic device may comprise the compound represented by general Formula (I) as defined above as the organic electron transport matrix (ETM) material. The electron transport layer may comprise, besides or instead of the compound represented by the general Formula (I), further ETM materials known in the art. Likewise, the electron transport layer may comprise as the only electron transport matrix material the compound represented by general Formula (I). In case that the inventive organic electronic device comprises more than one electron transport layers, the compound represented by the general Formula (I) may be comprised in only one of the electron transport layers, in more than one of the electron transport layers or in all of the electron transport layers. In accordance with the invention, the electron transport layer may comprise, besides the ETM material, at least one additive as defined below.

Further, the electron transport layer may comprise one or more n-type dopants. The additive may be an n-type dopant. The additive can be alkali metal, alkali metal compound, alkaline earth metal, alkaline earth metal compound, transition metal, transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. In another embodiment, the n-type dopant can be one selected from a group consisting of Cs, K, Rb, Mg, Na, Ca, Sr, Eu and Yb. In an embodiment the alkali metal compound may be 8-Hydroxyquinolinolato-lithium (LiQ), Lithium tetra(1H-pyrazol-1-yl)borate or Lithium 2-(diphenylphosphorylphenolate. Suitable compounds for the ETM (which may be used in addition to the inventive compound represented by the general Formula (I) as defined above) are not particularly limited. In one embodiment, the electron transport matrix compounds consist of covalently bound atoms. Preferably, the electron transport matrix compound comprises a conjugated system of at least 6, more preferably of at least 10 delocalized electrons. In one embodiment, the conjugated system of delocalized electrons may be comprised in aromatic or heteroaromatic structural moieties, as disclosed e.g. in documents EP 1 970 371 A1 or WO 2013/079217 A1.

Electron Injection Layer (EIL)

An optional EIL, which may facilitates injection of electrons from the cathode, may be formed on the ETL, preferably directly on the electron transport layer. Examples of materials for forming the EIL include lithium 8-hydroxyquinolinolate (LiQ), LiF, NaCl, CsF, Li2O, BaO, Ca, Ba, Yb, Mg which are known in the art. Deposition and coating conditions for forming the EIL are similar to those for formation of the HIL, although the deposition and coating conditions may vary, according to the material that is used to form the EIL. The EIL may be the organic semiconducting layer comprising the compound of Formula (I).

The thickness of the EIL may be in the range from about 0.1 nm to about 10 nm, for example, in the range from about 0.5 nm to about 9 nm. When the thickness of the EIL is within this range, the EIL may have satisfactory electron-injecting properties, without a substantial penalty in driving voltage.

Cathode Electrode

The cathode electrode is formed on the EIL if present. The cathode electrode may be formed of a metal, an alloy, an electrically conductive compound, or a mixture thereof. The cathode electrode may have a low work function. For example, the cathode electrode may be formed of lithium (Li), magnesium (Mg), aluminum (Al), aluminum (Al)-lithium (Li), calcium (Ca), barium (Ba), ytterbium (Yb), magnesium (Mg)-indium (In), magnesium (Mg)-silver (Ag), or the like. Alternatively, the cathode electrode may be formed of a transparent conductive oxide, such as ITO or IZO.

The thickness of the cathode electrode may be in the range from about 5 nm to about 1000 nm, for example, in the range from about 10 nm to about 100 nm. When the thickness of the cathode electrode is in the range from about 5 nm to about 50 nm, the cathode electrode may be transparent or semitransparent even if formed from a metal or metal alloy.

It is to be understood that the cathode electrode is not part of an electron injection layer or the electron transport layer.

Charge Generation Layer/Hole Generating Layer

The charge generation layer (CGL) may comprise a p-type and an n-type layer. An interlayer may be arranged between the p-type layer and the n-type layer.

Typically, the charge generation layer is a pn junction joining an n-type charge generation layer (electron generating layer) and a hole generating layer. The n-side of the pn junction generates electrons and injects them into the layer which is adjacent in the direction to the anode, Analogously, the p-side of the p-n junction generates holes and injects them into the layer which is adjacent in the direction to the cathode.

Charge generating layers are used in tandem devices, for example, in tandem OLEDs comprising, between two electrodes, two or more emission layers. In a tandem OLED comprising two emission layers, the n-type charge generation layer provides electrons for the first light emission layer arranged near the anode, while the hole generating layer provides holes to the second light emission layer arranged between the first emission layer and the cathode.

Suitable matrix materials for the hole generating layer may be materials conventionally used as hole injection and/or hole transport matrix materials. Also, p-type dopant used for the hole generating layer can employ conventional materials. For example, the p-type dopant can be one selected from a group consisting of tetrafluore-7,7,8,8-tetracyanoquinodimethane (F4-TCNQ), derivatives of tetracyanoquinodimethane, radialene derivatives, iodine, $FeCl_3$, $FeF_3$, and $SbCl_5$. Also, the host can be one selected from a group consisting of N,N'-di(naphthalen-1-yl)-N,N-diphenylbenzidine (NPB), N,N'-diphenyl-N,N'-bis(3-methylphenyl)-1,1-biphenyl-4,4'-diamine (TPD) and N,N',N'-tetranaphthylbenzidine (TNB). The p-type charge generation layer may consist of CNHAT.

The n-type charge generating layer may be the layer comprising the compound of Formula (I). The n-type charge generation layer can be layer of a neat n-type dopant, for example of an electropositive metal, or can consist of an organic matrix material doped with the n-type dopant. In one embodiment, the n-type dopant can be alkali metal, alkali metal compound, alkaline earth metal, alkaline earth metal compound, a transition metal, a transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. More specifically, the n-type dopant can be one selected from a group consisting of Cs, K, Rb, Mg, Na, Ca, Sr, Eu and Yb. Suitable matrix materials for the electron generating layer may be the materials conventionally used as matrix materials for electron injection or electron transport layers. The matrix material can be for example one selected from a group consisting of triazine compounds, hydroxyquinoline derivatives like tris(8-hydroxyquinoline)aluminum, benzazole derivatives, and silole derivatives.

The hole generating layer is arranged in direct contact to the n-type charge generation layer.

Organic Light-Emitting Diode (OLED)

The organic electronic device according to the invention may be an organic light-emitting device.

According to one aspect of the present invention, there is provided an organic light-emitting diode (OLED) comprising: a substrate; an anode electrode formed on the substrate; a hole injection layer, a hole transport layer, an emission layer, an organic semiconducting layer comprising a compound of Formula (I) and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an organic semiconducting layer comprising a compound of Formula (I) and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an organic semiconducting layer comprising a compound of Formula (I), an electron injection layer, and a cathode electrode.

According to various embodiments of the present invention, there may be provided OLEDs layers arranged between the above mentioned layers, on the substrate or on the top electrode.

According to one aspect, the OLED can comprise a layer structure of a substrate that is adjacent arranged to an anode electrode, the anode electrode is adjacent arranged to a first hole injection layer, the first hole injection layer is adjacent arranged to a first hole transport layer, the first hole transport layer is adjacent arranged to a first electron blocking layer, the first electron blocking layer is adjacent arranged to a first emission layer, the first emission layer is adjacent arranged to a first electron transport layer, the first electron transport layer is adjacent arranged to an n-type charge generation layer, the n-type charge generation layer is adjacent arranged to a hole generating layer, the hole generating layer is adjacent arranged to a second hole transport layer, the second hole transport layer is adjacent arranged to a second electron blocking layer, the second electron blocking layer is adjacent arranged to a second emission layer, between the second emission layer and the cathode electrode an optional electron transport layer and/or an optional injection layer are arranged.

The organic semiconducting layer according to the invention may be the electron transport layer, first electron transport layer, n-type charge generation layer and/or second electron transport layer.

For example, the OLED according to FIG. 2 may be formed by a process, wherein on a substrate (110), an anode (120), a hole injection layer (130), a hole transport layer (140), an electron blocking layer (145), an emission layer (150), a hole blocking layer (155), an electron transport layer (160), an electron injection layer (180) and the cathode electrode (190) are subsequently formed in that order.

Organic Electronic Device

An organic electronic device according to the invention comprises an organic semiconducting layer comprising a compound according to Formula (I).

An organic electronic device according to one embodiment may include a substrate, an anode layer, an organic semiconducting layer comprising a compound of Formula (I) and a cathode layer.

An organic electronic device according to one embodiment comprises at least one organic semiconducting layer comprising at least one compound of Formula (I), at least one anode layer, at least one cathode layer and at least one emission layer, wherein the organic semiconducting layer is preferably arranged between the emission layer and the cathode layer.

An organic light-emitting diode (OLED) according to the invention may include an anode, a hole transport layer (HTL), an emission layer (EML), an electron transport layer (ETL) comprising at least one compound of Formula (I), and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device.

According to another aspect of the present invention, there is provided a method of manufacturing an organic electronic device, the method using:

at least one deposition source, preferably two deposition sources and more preferred at least three deposition sources.

The methods for deposition that can be suitable comprise:
deposition via vacuum thermal evaporation;
deposition via solution processing, preferably the processing is selected from spin-coating, printing, casting; and/or
slot-die coating.

According to various embodiments of the present invention, there is provided a method using:
a first deposition source to release the compound of Formula (I) according to the invention, and
a second deposition source to release the metal, a metal salt or an alkali or alkaline earth metal complex; alternatively an organic alkali or alkaline earth metal complex; alternatively 8-hydroxyquinolinolato lithium or alkali borate;
the method comprising the steps of forming the organic semiconducting layer; whereby for an organic light-emitting diode (OLED):
the organic semiconducting layer is formed by releasing the compound of Formula (I) according to the invention from the first deposition source and a metal, a metal salt or an alkali or alkaline earth metal complex; alternatively an organic alkali or alkaline earth metal complex; alternatively 8-hydroxyquinolinolato lithium or alkali borate, from the second deposition source.

According to various embodiments of the present invention, the method may further include forming on the anode electrode, an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
on a substrate a first anode electrode is formed,
on the first anode electrode an emission layer is formed,
on the emission layer an electron transport layer stack is formed, optionally a hole blocking layer is formed on the emission layer and an organic semiconducting layer is formed,
and finally a cathode electrode is formed,
optional a hole injection layer, a hole transport layer, and a hole blocking layer, formed in that order between the first anode electrode and the emission layer,
optional an electron injection layer is formed between the organic semiconducting layer and the cathode electrode.

According to various embodiments of the present invention, the method may further comprise forming an electron injection layer on the organic semiconducting layer. However, according to various embodiments of the OLED of the present invention, the OLED may not comprise an electron injection layer.

According to various embodiments, the OLED may have the following layer structure, wherein the layers having the following order:
anode, hole injection layer, first hole transport layer, second hole transport layer, emission layer, optional hole blocking layer, organic semiconducting layer comprising a compound of Formula (I) according to the invention, optional electron injection layer, and cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

In one embodiment, the organic electronic device according to the invention comprising an organic semiconducting layer comprising a compound according to Formula (I) may further comprise a layer comprising a radialene compound and/or a quinodimethane compound.

In one embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have Formula (XX) and/or the quinodimethane compound may have Formula (XXIa) or (XXIb):

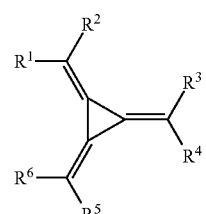

(XX)

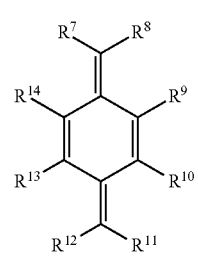

(XXIa)

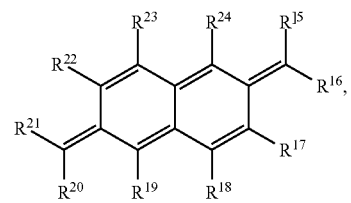

(XXIb)

wherein $R^1$, $R^2$, $R^3$, $R^4$, $R^5$, $R^6$, $R^7$, $R^8$, $R^{11}$, $R^{12}$, $R^{15}$, $R^{16}$, $R^{20}$, $R^{21}$ are independently selected from above mentioned electron withdrawing groups and $R^9$, $R^{10}$, $R^{13}$, $R^{14}$, $R^{17}$, $R^{18}$, $R^{19}$, $R^{22}$, $R^{23}$ and $R^{24}$ are independently selected from H, halogen and above mentioned electron withdrawing groups.

Hereinafter, the embodiments are illustrated in more detail with reference to examples. However, the present disclosure is not limited to the following examples. Reference will now be made in detail to the exemplary aspects.

DETAILS AND DEFINITIONS OF THE INVENTION

In the present specification, when a definition is not otherwise provided, an "alkyl group" may refer to an aliphatic hydrocarbon group. The alkyl group may refer to "a saturated alkyl group" without any double bond or triple bond. The term "alkyl" as used herein shall encompass linear as well as branched and cyclic alkyl. For example, $C_3$-alkyl may be selected from n-propyl and iso-propyl. Likewise, $C_4$-alkyl encompasses n-butyl, sec-butyl and t-butyl. Likewise, $C_6$-alkyl encompasses n-hexyl and cyclohexyl.

As used herein if not explicitly mentioned else, the asterisk symbol "*" represents a binding position at which the moiety labelled accordingly is bond to another moiety.

The subscribed number n in $C_n$ relates to the total number of carbon atoms in the respective alkyl, arylene, heteroarylene or aryl group.

The term "aryl" or "arylene" as used herein shall encompass phenyl ($C_6$-aryl), fused aromatics, such as naphthalene, anthracene, phenanthrene, tetracene etc. Further encompassed are biphenyl and oligo- or polyphenyls, such as terphenyl, phenyl-substituted biphenyl, phenyl-substituted terphenyl (such as tetraphenyl benzole groups) etc. "Arylene" respectively "heteroarylene", refers to groups to which two further moieties are attached. In the present specification, the term "aryl group" or "arylene group" may refer to a group comprising at least one hydrocarbon aromatic moiety, and all the elements of the hydrocarbon aromatic moiety may have p-orbitals which form conjugation, for example a phenyl group, a napthyl group, an anthracenyl group, a phenanthrenyl group, a pyrinyl group, a fluorenyl group and the like. Further encompoassed are spiro compounds in which two aromatic moieties are connected with each other via a spiro-atom, such as 9,9'-spirobi[9H-fluorene]yl. The aryl or arylene group may include a monocyclic or fused ring polycyclic (i.e., links sharing adjacent pairs of carbon atoms) functional group.

The term "heteroaryl" as used herein refers to aryl groups in which at least one carbon atom is substituted with a heteroatom. The term "heteroaryl" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S. A heteroarylene ring may comprise at least 1 to 3 heteroatoms. Preferably, a heteroarylene ring may comprise at least 1 to 3 heteroatoms individually selected from N, S and/or O. Just as in case of "aryl"/"arylene", the term "heteroaryl" comprises, for example, spiro compounds in which two aromatic moieties are connected with each other, such as spiro[fluorene-9,9'-xanthene]. Further exemplary heteroaryl groups are diazine, triazine, dibenzofurane, dibenzothiofurane, acridine, benzoacridine, dibenzoacridine etc.

In case that the aryl, arylene, heteroaryl or heteroarylene group is substituted, it may be preferred that the substituent is $CH_3$ or phenyl.

The term "alkenyl" as used herein refers to a group —$CR^1$=$CR^2R^3$ comprising a carbon-carbon double bond.

The term "perhalogenated" as used herein refers to a hydrocarbyl group wherein all of the hydrogen atoms of the hydrocarbyl group are replaced by halogen (F, Cl, Br, I) atoms.

The term "alkoxy" as used herein refers to a structural fragment of the Formula —OR with R being hydrocarbyl, preferably alkyl or cycloalkyl.

The term "thioalkyl" as used herein refers to a structural fragment of the Formula —SR with R being hydrocarbyl, preferably alkyl or cycloalkyl.

The subscripted number n in $C_n$-heteroaryl merely refers to the number of carbon atoms excluding the number of heteroatoms. In this context, it is clear that a $C_3$ heteroarylene group is an aromatic compound comprising three carbon atoms, such as pyrazol, imidazole, oxazole, thiazole and the like.

The term "heteroaryl" as used herewith shall encompass pyridine, quinoline, benzoquinoline, quinazoline, benzoquinazoline, pyrimidine, pyrazine, triazine, benzimidazole, benzothiazole, benzo[4,5]thieno[3,2-d]pyrimidine, carbazole, xanthene, phenoxazine, benzoacridine, dibenzoacridine and the like.

In the present specification, the single bond refers to a direct bond.

The term "fluorinated" as used herein refers to a hydrocarbon group in which at least one of the hydrogen atoms comprised in the hydrocarbon group is substituted by a fluorine atom. Fluorinated groups in which all of the hydrogen atoms thereof are substituted by fluorine atoms are referred to as perfluorinated groups and are particularly addressed by the term "fluorinated".

In terms of the invention, a group is "substituted with" another group if one of the hydrogen atoms comprised in this group is replaced by another group, wherein the other group is the substituent.

In terms of the invention, the expression "between" with respect to one layer being between two other layers does not exclude the presence of further layers which may be arranged between the one layer and one of the two other layers. In terms of the invention, the expression "in direct contact" with respect to two layers being in direct contact with each other means that no further layer is arranged between those two layers. One layer deposited on the top of another layer is deemed to be in direct contact with this layer.

With respect to the inventive organic semiconductive layer as well as with respect to the inventive compound, the compounds mentioned in the experimental part are most preferred.

The inventive organic electronic device may be an organic electroluminescent device (OLED) an organic photovoltaic device (OPV), a lighting device, or an organic field-effect transistor (OFET). A lighting device may be any of the devices used for illumination, irradiation, signaling, or projection. They are correspondingly classified as illuminating, irradiating, signaling, and projecting devices. A lighting device usually consists of a source of optical radiation, a device that transmits the radiant flux into space in the desired direction, and a housing that joins the parts into a single device and protects the radiation source and light-transmitting system against damage and the effects of the surroundings.

According to another aspect, the organic electroluminescent device according to the present invention may comprise more than one emission layer, preferably two or three emission layers. An OLED comprising more than one emission layer is also described as a tandem OLED or stacked OLED.

The organic electroluminescent device (OLED) may be a bottom- or top-emission device.

Another aspect is directed to a device comprising at least one organic electroluminescent device (OLED).

A device comprising organic light-emitting diodes is for example a display or a lighting panel.

In the present invention, the following defined terms, these definitions shall be applied, unless a different definition is given in the claims or elsewhere in this specification.

In the context of the present specification the term "different" or "differs" in connection with the matrix material means that the matrix material differs in their structural Formula.

The terms "OLED" and "organic light-emitting diode" are simultaneously used and have the same meaning. The term "organic electroluminescent device" as used herein may comprise both organic light emitting diodes as well as organic light emitting transistors (OLETs).

As used herein, "weight percent", "wt.-%", "percent by weight", "% by weight", and variations thereof refer to a composition, component, substance or agent as the weight of that component, substance or agent of the respective electron transport layer divided by the total weight of the respective electron transport layer thereof and multiplied by 10. It is under-stood that the total weight percent amount of all components, substances and agents of the respective electron transport layer and electron injection layer are selected such that it does not exceed 100 wt.-%.

As used herein, "volume percent", "vol.-%", "percent by volume", "% by volume", and variations thereof refer to a composition, component, substance or agent as the volume of that component, substance or agent of the respective electron transport layer divided by the total volume of the respective electron transport layer thereof and multiplied by 100. It is understood that the total volume percent amount of all components, substances and agents of the cathode layer are selected such that it does not exceed 100 vol.-%.

All numeric values are herein assumed to be modified by the term "about", whether or not explicitly indicated. As used herein, the term "about" refers to variation in the numerical quantity that can occur. Whether or not modified by the term "about" the claims include equivalents to the quantities.

It should be noted that, as used in this specification and the appended claims, the singular forms "a", "an", and "the" include plural referents unless the content clearly dictates otherwise.

The term "free of", "does not contain", "does not comprise" does not exclude impurities. Impurities have no technical effect with respect to the object achieved by the present invention.

In the context of the present specification the term "essentially non-emissive" or "non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconducting layer comprising the compound of Formula (I) is essentially non-emissive or non-emitting.

The operating voltage, also named U, is measured in Volt (V) at 10 milliAmpere per square centimeter (mA/cm2).

The candela per Ampere efficiency, also named cd/A efficiency is measured in candela per ampere at 10 milli-Ampere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "life-span" and "lifetime" are simultaneously used and have the same meaning.

The anode electrode and cathode electrode may be described as anode electrode/cathode electrode or anode electrode/cathode electrode or anode electrode layer/cathode electrode layer.

Room temperature, also named ambient temperature, is 23° C.

BRIEF DESCRIPTION OF THE DRAWINGS

These and/or other aspects and advantages of the present invention will become apparent and more readily appreciated from the following description of the exemplary embodiments, taken in conjunction with the accompanying drawings, of which.

DETAILED DESCRIPTION

Figure 1:
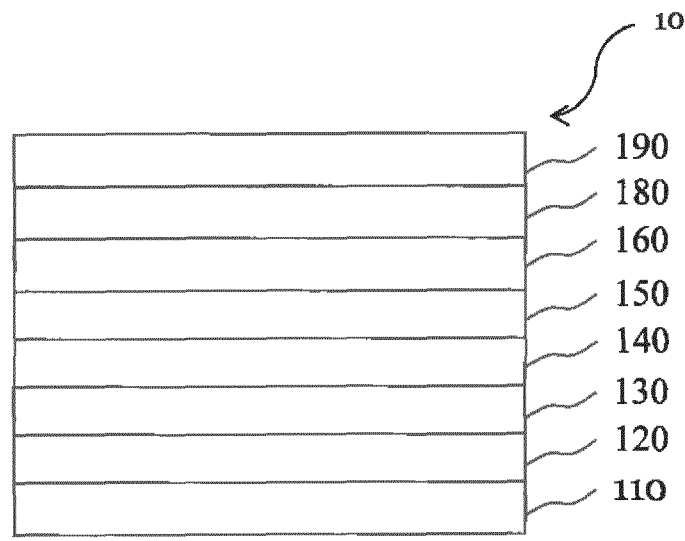
FIG. 1 is a schematic sectional view of an organic light-emitting diode (OLED), according to an exemplary embodiment of the present invention.

Reference will now be made in detail to the exemplary embodiments of the present invention, examples of which are illustrated in the accompanying drawings, wherein like reference numerals refer to the like elements throughout. The exemplary embodiments are described below, in order to explain the aspects of the present invention, by referring to the figures.

Herein, when a first element is referred to as being formed or disposed "on" or "onto" a second element, the first element can be disposed directly on the second element, or one or more other elements may be disposed there between. When a first element is referred to as being formed or disposed "directly on" or "directly onto" a second element, no other elements are disposed there between.

FIG. 1 is a schematic sectional view of an organic light-emitting diode (OLED) 100, according to an exemplary embodiment of the present invention. The OLED 100 includes a substrate 110, an anode 120, a hole injection layer (HIL) 130, a hole transport layer (HTL) 140, an emission layer (EML) 150, an electron transport layer (ETL) 160. The electron transport layer (ETL) 160 is formed on the EML 150. Onto the electron transport layer (ETL) 160, an electron injection layer (EIL) 180 is disposed. The cathode 190 is disposed directly onto the electron injection layer (EIL) 180.

Instead of a single electron transport layer 160, optionally an electron transport layer stack (ETL) can be used.

Figure 2:
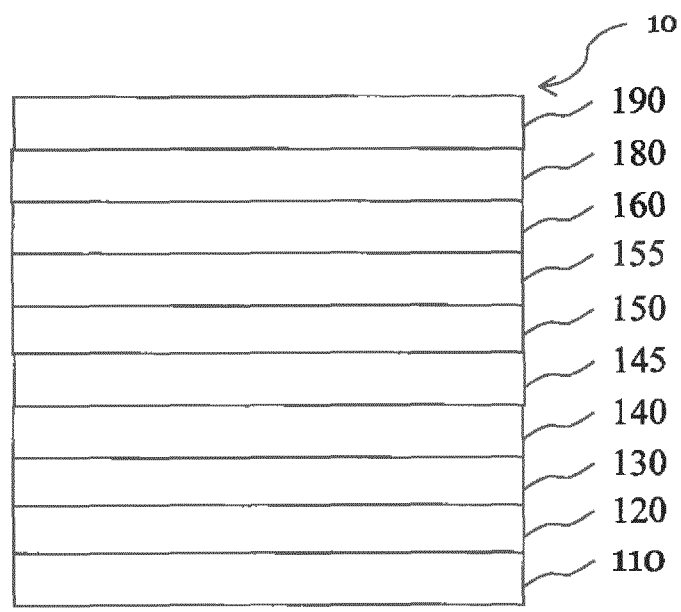
FIG. 2 is a schematic sectional view of an OLED, according to an exemplary embodiment of the present invention.

FIG. 2 is a schematic sectional view of an OLED 100, according to another exemplary embodiment of the present invention. FIG. 2 differs from FIG. 1 in that the OLED 100 of FIG. 2 comprises an electron blocking layer (EBL) 145 and a hole blocking layer (HBL) 155.

Referring to FIG. 2, the OLED 100 includes a substrate 110, an anode 120, a hole injection layer (HIL) 130, a hole transport layer (HTL) 140, an electron blocking layer (EBL) 145, an emission layer (EML) 150, a hole blocking layer (HBL) 155, an electron transport layer (ETL) 160, an electron injection layer (EIL) 180 and a cathode electrode 190.

Preferably, the organic semiconducting layer comprising a compound of Formula (I) may be an ETL.

Figure 3:
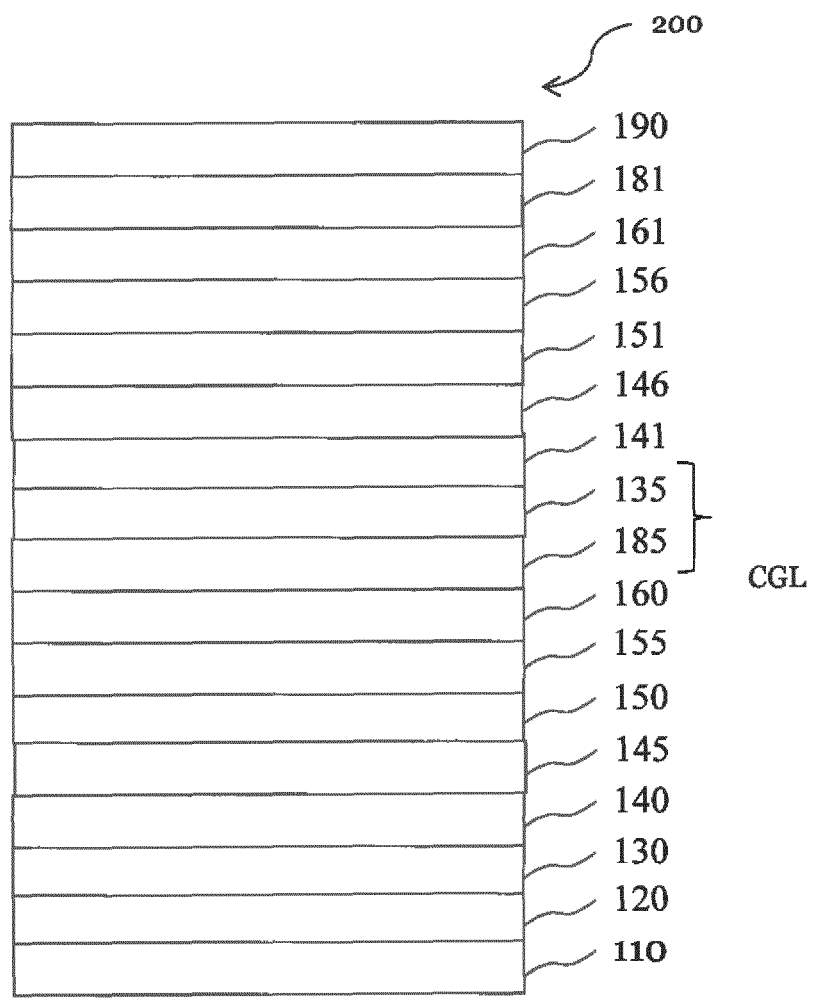
FIG. 3 is a schematic sectional view of a tandem OLED comprising a charge generation layer, according to an exemplary embodiment of the present invention.

FIG. 3 is a schematic sectional view of a tandem OLED 200, according to another exemplary embodiment of the present invention. FIG. 3 differs from FIG. 2 in that the OLED 100 of FIG. 3 further comprises a charge generation layer (CGL) and a second emission layer (151).

Referring to FIG. 3, the OLED 200 includes a substrate 110, an anode 120, a first hole injection layer (HIL) 130, a first hole transport layer (HTL) 140, a first electron blocking layer (EBL) 145, a first emission layer (EML) 150, a first hole blocking layer (HBL) 155, a first electron transport layer (ETL) 16o, an n-type charge generation layer (n-type CGL) 185, a hole generating layer (p-type charge generation layer; p-type GCL) 135, a second hole transport layer (HTL) 141, a second electron blocking layer (EBL) 146, a second emission layer (EML) 151, a second hole blocking layer (EBL) 156, a second electron transport layer (ETL) 161, a second electron injection layer (EIL) 181 and a cathode 190.

Preferably, the organic semiconducting layer comprising a compound of Formula (I) may be the first ETL, n-type CGL and/or second ETL.

While not shown in FIG. 1, FIG. 2 and FIG. 3, a sealing layer may further be formed on the cathode electrodes 190, in order to seal the OLEDs 100 and 200. In addition, various other modifications may be applied thereto.

Hereinafter, one or more exemplary embodiments of the present invention will be described in detail with, reference to the following examples. However, these examples are not intended to limit the purpose and scope of the one or more exemplary embodiments of the present invention.

EXPERIMENTAL DATA

Preparation of Compounds of Formula (I)

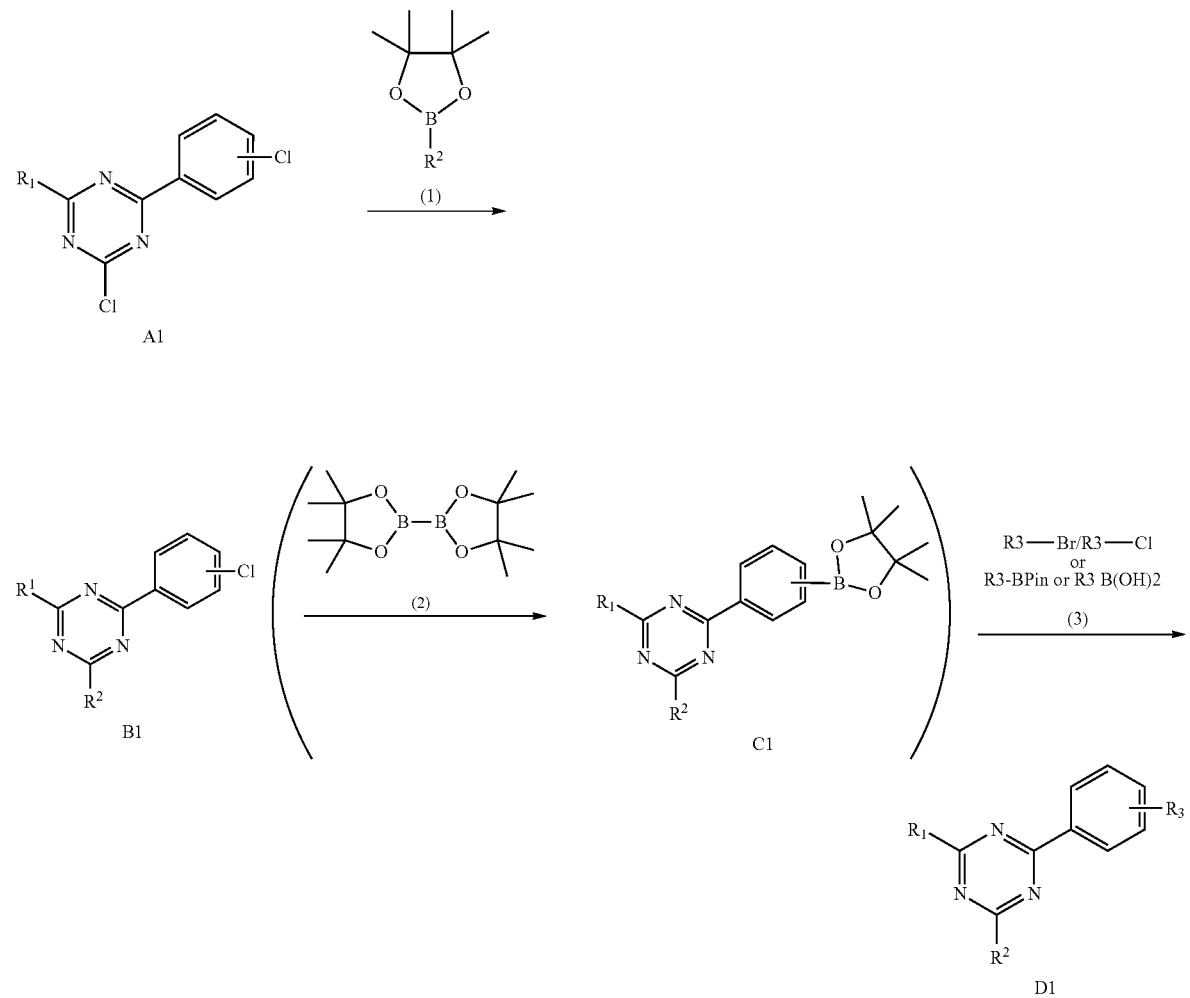

Compounds of formula (I) may be synthesized as shown below.

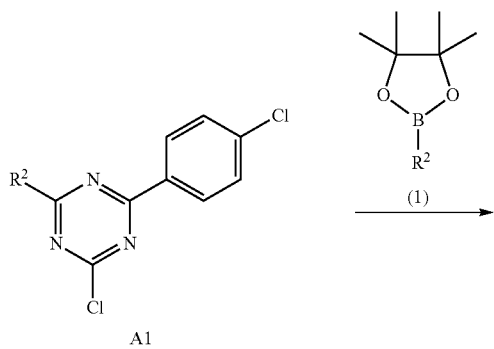

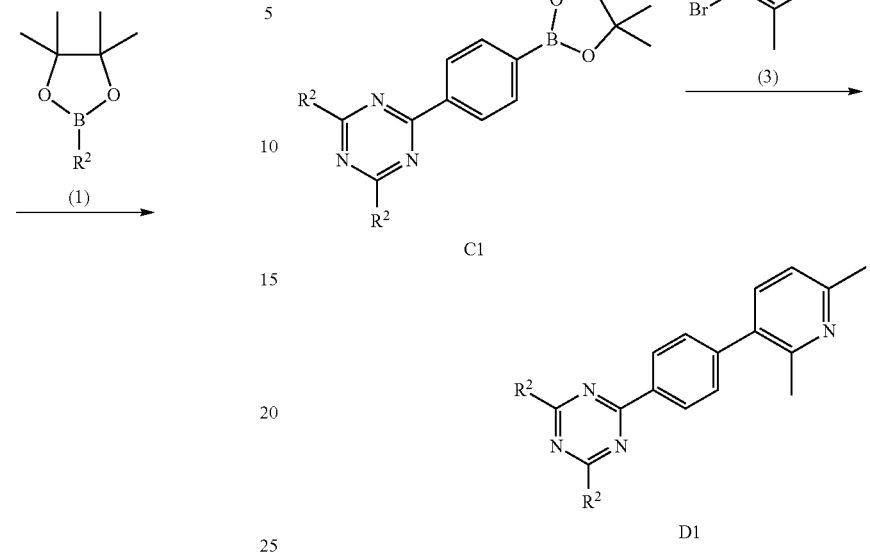

1st Step:

A flask was flushed with nitrogen and charged with compound (1) (98-3 mmol), compound A1 (108.2 mmol), K₂CO₃ (196.7 mmol), Tetrakis(triphenylphosphin)palladium(0) (2.0 mmol). A deaerated mixture of THF and water (4:1, 500 mL) was added and the reaction mixture was heated to 66° C. under a nitrogen atmosphere overnight. After cooling down to room temperature, the resulting precipitate was isolated by suction filtration and washed with water (600 mL). The crude product was then dissolved in dichloromethane and filtered through a pad of silica gel. After rinsing with additional dichloromethane (2.5 L mL), the filtrate was concentrated under reduced pressure. The resulting precipitate was isolated by suction filtration and triturated in THF (800 mL) to yield compound B1 after drying.

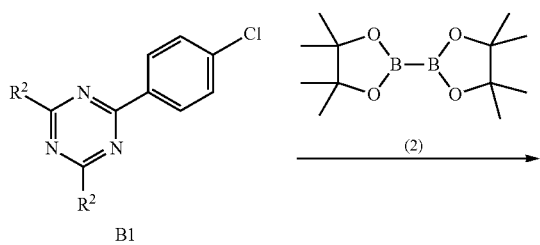

2nd Step:

To synthesis C1 A flask was flushed with nitrogen and charged with compound B1 (39.2 mmol), 4,4,4',4',5,5,5',5'-octamethyl-2,2'-bi(1,3,2-dioxaborolane) (51.0 mmol), KOAc (117.6 mmol), 2-Dicyclohexylphosphino-2',4',6'-triisopropylbiphenyl (2.0 mmol) and tris(dibenzylidenacetone)dipalladium(0) (mmol), Anhydrous dioxane (200 mL) was added and the reaction mixture was heated to 100° C. under a nitrogen atmosphere overnight. After cooling down to room temperature, the resulting precipitate was isolated by suction filtration and washed with water (600 mL) and methanol (200 mL). The crude product was then dissolved in dichloromethane and filtered through a pad of Florisil. After rinsing with additional dichloromethane (2.5 L mL), the filtrate was concentrated under reduced pressure. The resulting precipitate was isolated by suction filtration and washed with n-hexane (100 mL) to yield 24.6 g of C1 after drying.

3rd Step:

A flask was flushed with nitrogen and charged with C1 (16.3 mmol), 3-bromo-2,6-dimethylpyridine (3) (19.6 mmol), K₃PO₄ (40.8 mmol) and chloro(crotyl)(2-dicyclohexylphosphino-2',6'-dimethoxybiphenyl)palladium(II) (198 mg, 0.33 mmol). A mixture of deaerated dioxane and water (4:1, 100 mL) was added and the reaction mixture was heated to 50° C. under a nitrogen atmosphere overnight. After cooling down to room temperature, the resulting precipitate was isolated by suction filtration and washed with water (1.0 L) and Methanol (100 mL). The crude product was dissolved in dichloromethane and washed with an aqueous solution of NADTC (3%, 150 mL), and then with water (2×200 mL). The organic phase was dried over Na₂SO₄ and filtered through a pad of silica gel. After rinsing with additional dichloromethane (2.0 L), and dichloromethane/methanol (98/2, 1.5 L), the filtrate was concentrated under reduced pressure. The resulting precipitate was isolated by suction filtration to yield D1 after drying. Final purification was achieved by sublimation.

Synthesis of 2,4-diphenyl-6-(4"-(3,5,6-triphenylpyrazin-2-yl)-[1,1':3',1"-terphenyl]-3-yl)-1,3,5-triazine (Compound 1)

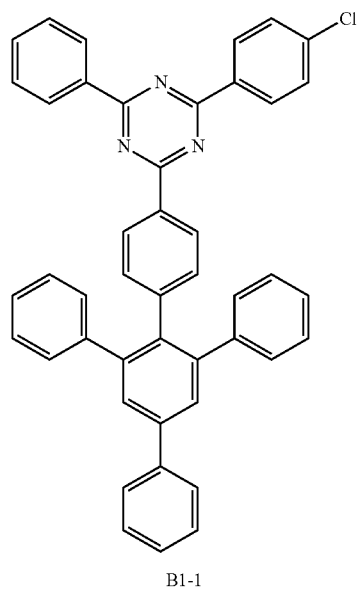

B1-1

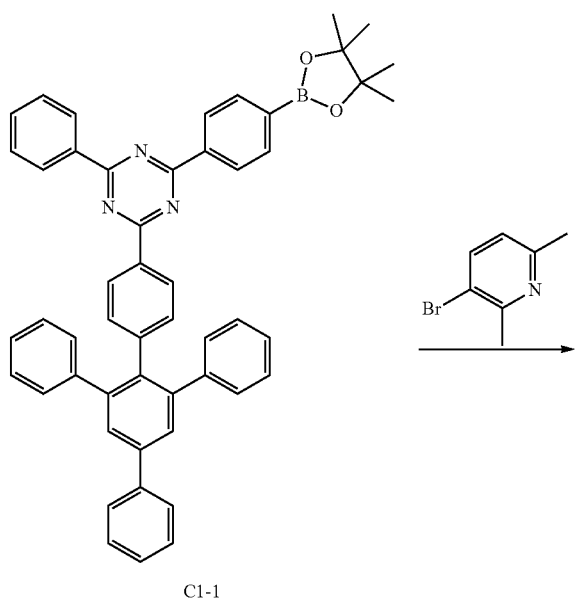

C1-1

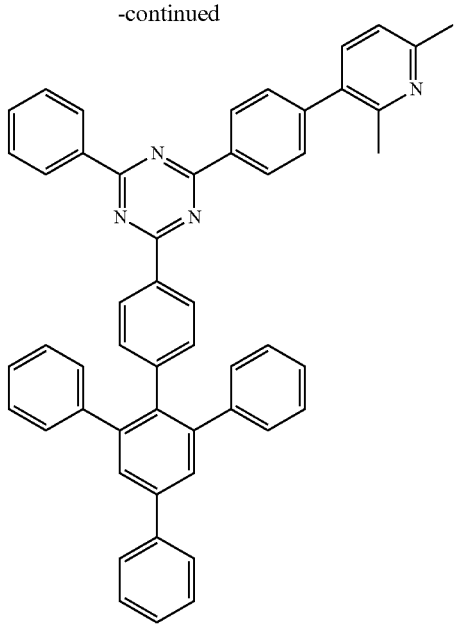

compound 1

1st Step:
To synthesis 2-(4-chlorophenyl)-4-(2',6'-diphenyl-[1,1':4',1"-terphenyl]-4-yl)-6-phenyl-1,3,5-triazine (B1-1) a flask was flushed with nitrogen and charged with 2-(2',6'-diphenyl-[1,1':4',1"-terphenyl]-4-yl)-4,4,5,5-tetramethyl-1,3,2-dioxaborolane (50.0 g, 98.3 mmol), 2-chloro-4-(4-chlorophenyl)-6-phenyl-1,3,5-triazine (32.7 g, 108.2 mmol), $K_2CO_3$ (27.2 g, 196.7 mmol), Tetrakis(triphenylphosphin)palladium (0) (2.3 g, 2.0 mmol). A deaerated mixture of THF and water (4:1, 500 mL) was added and the reaction mixture was heated to 66° C. under a nitrogen atmosphere overnight. After cooling down to room temperature, the resulting precipitate was isolated by suction filtration and washed with water (600 mL). The crude product was then dissolved in dichloromethane and filtered through a pad of silicagel. After rinsing with additional dichloromethane (2.5 L mL), the filtrate was concentrated under reduced pressure. The resulting precipitate was isolated by suction filtration and triturated in THF (800 mL) to yield 25.7 g of (B1-1) after drying.

2nd Step:
To synthesis 2-(2',6'-diphenyl-[1,1':4',1"-terphenyl]-4-yl)-4-phenyl-6-(4-(4,4,5,5-tetramethyl-1,3,2-dioxaborolan-2-yl)phenyl)-1,3,5-triazine (C1-1) a flask was flushed with nitrogen and charged with 2-(4-chlorophenyl)-4-(2',6'-diphenyl-[1,1':4',1"-terphenyl]-4-yl)-6-phenyl-1,3,5-triazine (24.4 g, 39.2 mmol), 4,4,4',4',5,5,5',5'-octamethyl-2,2'-bi(1,3,2-dioxaborolane) (12.9 g, 51.0 mmol), KOAc (11.5 g, 117.6 mmol), 2-Dicyclohexylphosphino-2',4',6'-triisopropylbiphenyl (34 mg, 2.0 mmol) and tris(dibenzylidenacetone)dipalladium(0) (897 mg, 1 mmol). Anhydrous dioxane (200 mL) was added and the reaction mixture was heated to 100° C. under a nitrogen atmosphere overnight. After cooling down to room temperature, the resulting precipitate was isolated by suction filtration and washed with water (600 mL) and methanol (200 mL). The crude product was then dissolved in dichloromethane and filtered through a pad of Florisil. After rinsing with additional dichloromethane (2.5 L mL), the filtrate was concentrated under reduced pressure. The resulting precipitate was isolated by suction filtration and washed with n-hexane (100 mL) to yield 24.6 g (86%) of (C1-1).

3rd Step:

Next a flask was flushed with nitrogen and charged with 2-(2',6'-diphenyl-[1,1':4',1''-terphenyl]-4-yl)-4-phenyl-6-(4-(4,4,5,5-tetramethyl-1,3,2-dioxaborolan-2-yl)phenyl)-1,3,5-triazine (12.2 g, 16.3 mmol), 3-bromo-2,6-dimethylpyridine (2.6 mL, 19.6 mmol), K$_3$PO$_4$ (0.7 g, 40.8 mmol) and chloro(crotyl)(2-dicyclohexylphosphino-2',6'-dimethoxybiphenyl)palladium(II) (198 mg, 0-33 mmol). A mixture of deaerated dioxane and water (4:1, 100 mL) was added and the reaction mixture was heated to 50° C. under a nitrogen atmosphere overnight. After cooling down to room temperature, the resulting precipitate was isolated by suction filtration and washed with water (1.0 L) and Methanol (100 mL). The crude product was dissolved in dichloromethane and washed with an aqueous solution of NADTC (3%, 150 mL), and then with water (2×200 mL). The organic phase was dried over Na$_2$SO$_4$ and filtered through a pad of silicagel. After rinsing with additional dichloromethane (2.0 L), and dichloromethane/methanol (98/2, 1.5 L), the filtrate was concentrated under reduced pressure. The resulting precipitate was isolated by suction filtration to yield 6.4 g compound 1 after drying. Final purification was achieved by sublimation. HPLC/ESI-MS: 100%, m/z=719.2 ([M+H]$^+$).

A1: 2-(2',6'-diphenyl-[1,1':4',1''-terphenyl]-4-yl)-4,4,5,5-tetrarethyl-1,3,2-dioxaborolane was synthesized from 1093881-99-2, using standard borilation conditions described in WO2017135510A1.

Synthesis of 2-(3-(2,6-dimethylpyridin-3-yl)phenyl)-4-(2',6'-diphenyl-[1,1':4',1''-terphenyl]-4-yl)-6-phenyl-1,3,5-triazine (Compound 2)

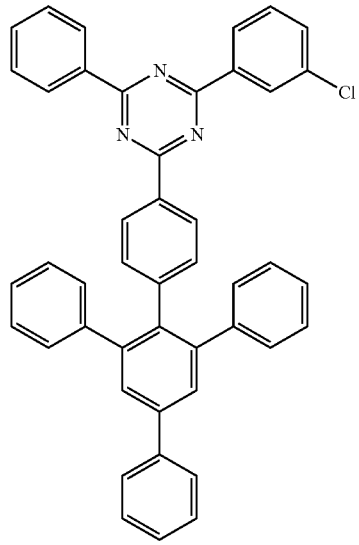

B1-2

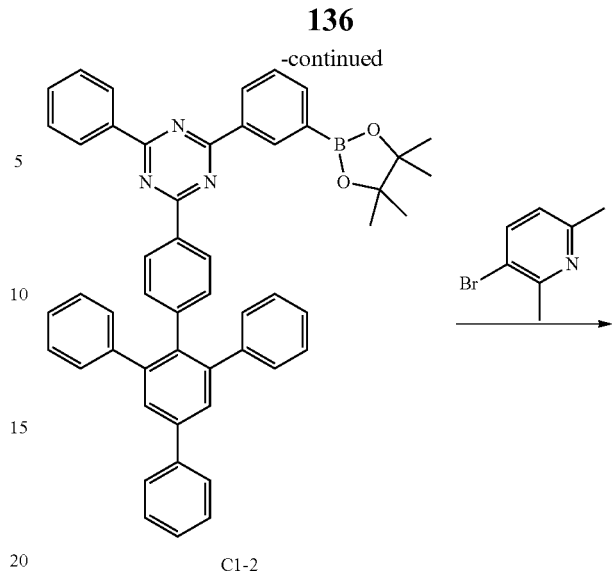

C1-2

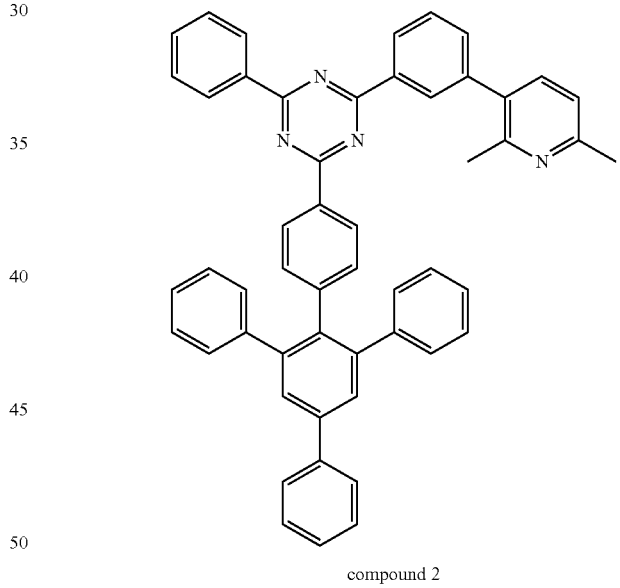

compound 2

Compound 2 was synthesized according to the general procedure and using reagent given in table below

| Step | Reagent1 | Reagent2 | Catalyst | Base | Ligand | Solvent Temp. | Amount HPLC/ ESI-MS |
|---|---|---|---|---|---|---|---|
| 1$^{st}$ | A2: 1.1 eq | 50 g | 14221-01-3 2 mol % | 584-08-7 2.0 eq. | x | THF/H$_2$O 4/1 66° C. | 59.8 g |
| 2$^{nd}$ | B1-2: 40 g | 73183-34-3 1.3 eq. | 51364-51-3 2.5 mol % | 127-08-2 3 eq. | 564483-18-7 5 mol % | Dioxane 90° C. | 41.9 g |
| 3$^{rd}$ | C1-2: 20 g | 3430-31-7 1.2 eq | 1798781-99-3 2 mol % | 7778-53-2 2.0 eq | x | Diox./H$_2$O 4/1 45° C. | 7.7 g HPLC/ ESI-MS: |

-continued

| Step | Reagent1 | Reagent2 | Catalyst | Base | Ligand | Solvent Temp. | Amount HPLC/ ESI-MS |
|---|---|---|---|---|---|---|---|
| | | | | | | | 99.95%, m/z = 719.2 ([M + H])+ |

Synthesis of 2-(2',6'-diphenyl-[1,1':4',1''-terphenyl]-4-yl)-4-(3-(2-methylpyridin-3-yl)phenyl)-6-phenyl-1,3,5-triazine (Compound 167)

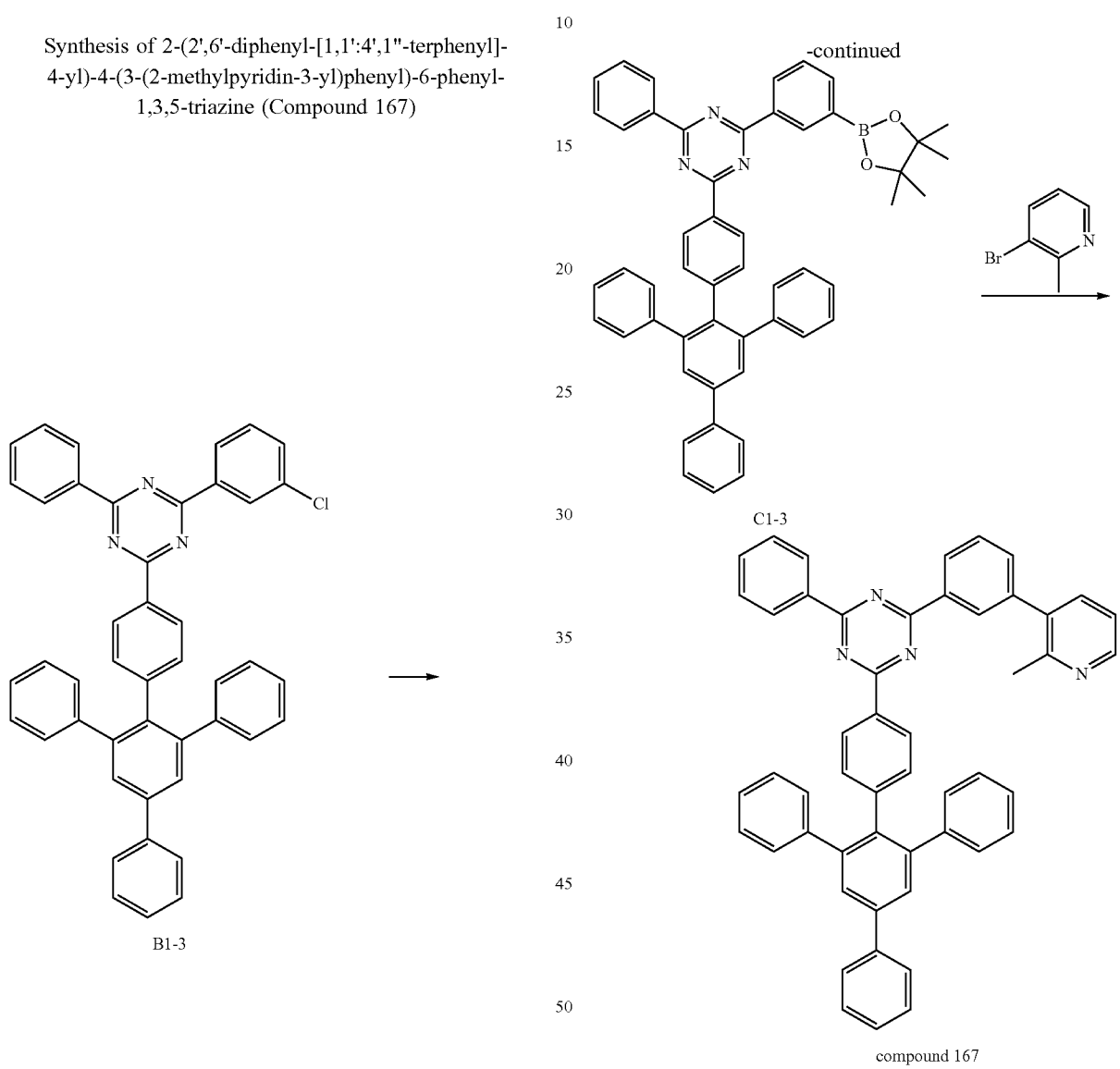

Compound 167 was synthesized according to the general procedure an using reagent given in table below

| Step | Reagent1 | Reagent2 | Catalyst | Base | Ligand | Solvent Temp. | Amount HPLC/ ESI-MS |
|---|---|---|---|---|---|---|---|
| 1st | A2: 1.1 eq | 50 g | 14221- 01-3 2 mol % | 584- 08-7 2.0 eq. | x | THF/H2O 4/1 66° C. | 59.8 g |
| 2nd | B1-3: 40 g | 73183- 34-3 1.3 eq. | 51364- 51-3 2.5 mol % | 127- 08-2 3 eq. | 564483- 18-7 5 mol % | Dioxane 90° C. | 41.9 g |

-continued

| Step | Reagent1 | Reagent2 | Catalyst | Base | Ligand | Solvent Temp. | Amount HPLC/ ESI-MS |
|---|---|---|---|---|---|---|---|
| 3rd | C1-3: 10 g | 38749-79-0 1.2 eq | 1798781-99-3 2 mol % | 7778-53-2 2.0 eq | x | Diox./H₂O 4/1 45° C. | 2.8 g (29%) HPLC/ ESI-MS: 99.95%, m/z = 705.3 ([M + H])⁺ |

2-(2',6'-diphenyl-[1,1':4',1"-terphenyl]-4-yl)-4,4,5,5-tetrmethyl-1,3,2-dioxaborolane was synthesized from 1093881-99-2, using standard borilation conditions described in WO2017135510A1.

Synthesis of 2-(2',6'-diphenyl-[1,1':4',1"-terphenyl]-4-yl)-4-(3-(2-methylpyridin-3-yl)phenyl)-6-phenyl-1,3,5-triazine (Compound 119)

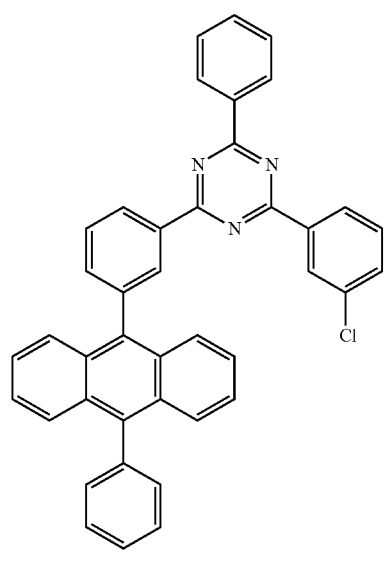

B1-4

-continued

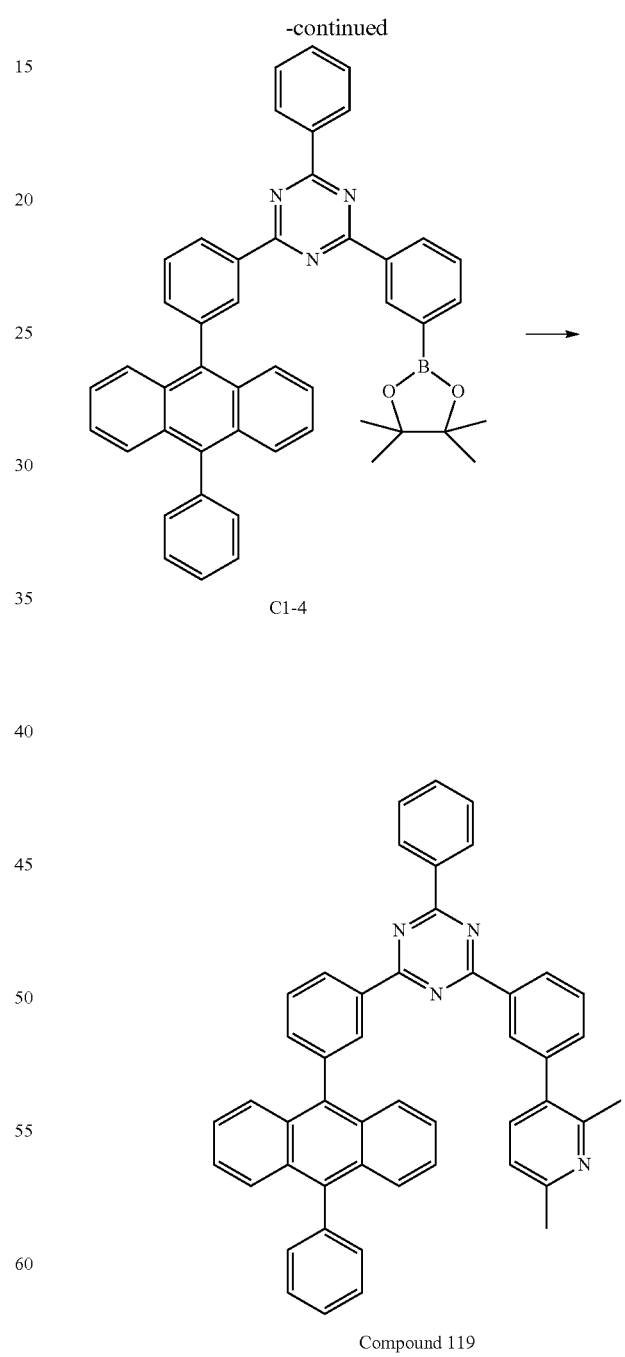

C1-4

Compound 119

Compound 119 was synthesized according to the general procedure and using reagent given in table below

| Step | Reagent1 | Reagent2 | Catalyst | Base | Ligand | Solvent Temp. | Amount (yield) HPLC/ ESI-MS |
|---|---|---|---|---|---|---|---|
| 1st | A2: 1.0 eq. | 1023674-81-8 45.3 g | 14221-01-3 2 mol % | 584-08-7 2.0 eq. | x | THF/H$_2$O 4/1 | 34.8 g |
| 2nd | B1-4: 28.8 g | 73183-34-3 1.3 eq. | 51364-51-3 2.5 mol % | 127-08-2 3 eq. | 564483-18-7 5 mol % | Dioxane 100° C. | 30.6 g |
| 3rd | C1-4: 15 g | 3430-31-7 1.2 eq | 1798781-99-3 2 mol % | 7778-53-2 2.0 eq | x | Diox./H$_2$O 4/1 45° C. | 6.0 g (41%) HPLC/ ESI-MS: 99.8%, m/z = 667.2 ([M + H])$^+$ |
Synthesis of 2-(3-(2,6-dimethylpyridin-3-yl)phenyl)-4-phenyl-6-(3-(3,5,6-triphenylpyrazin-2-yl)phenyl)-1,3,5-triazine (Compound 125)
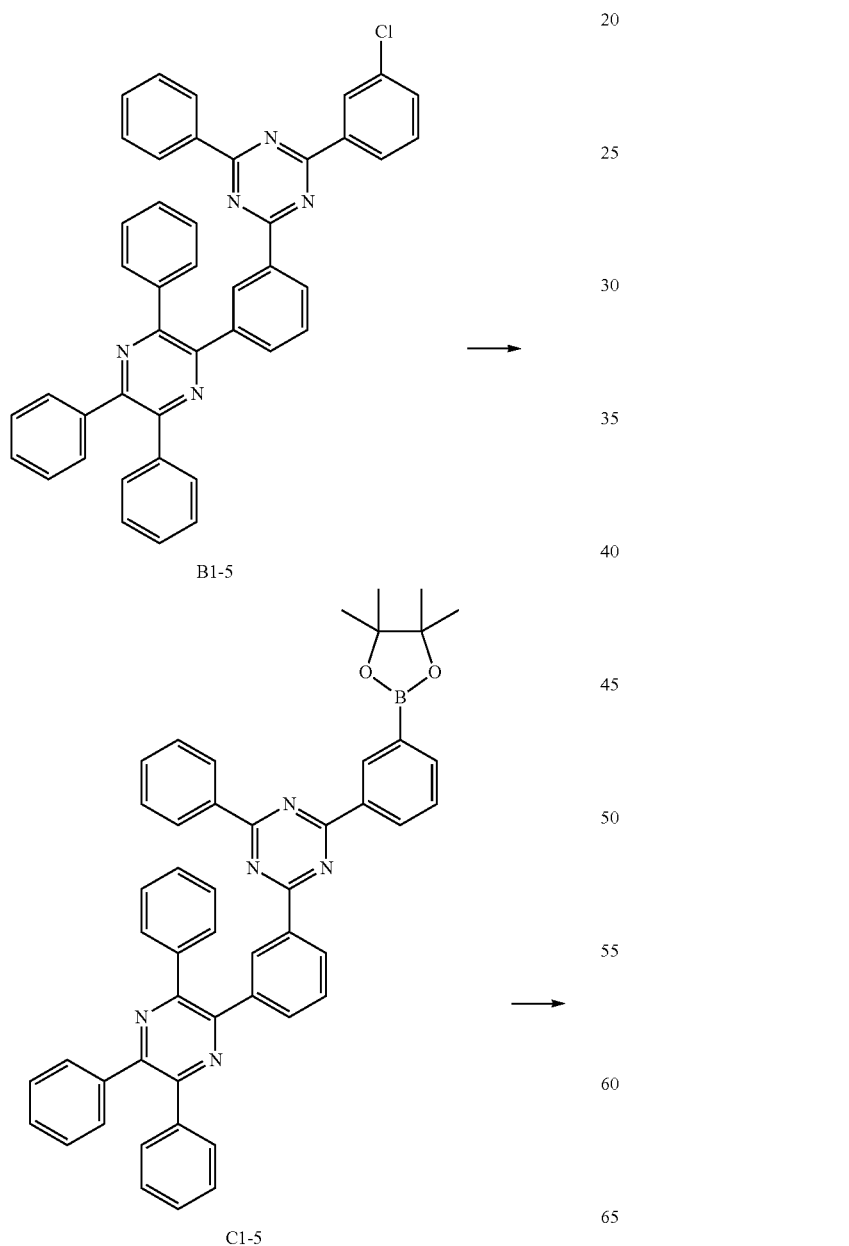

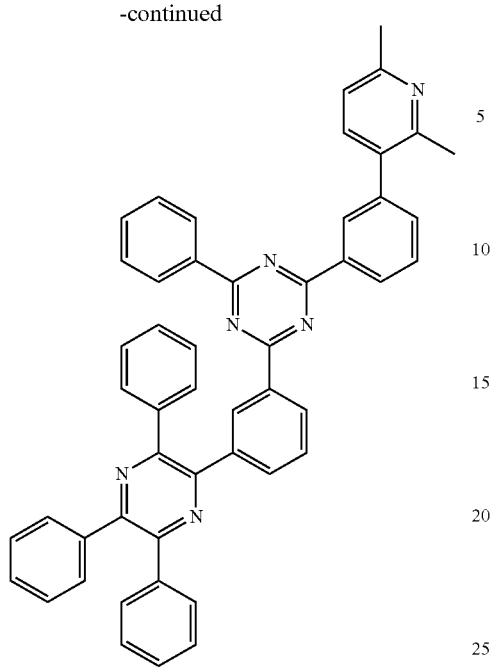

Compound 125

Compound 125 was synthesized according to the general procedure and using reagent given in table below

| Step | Reagent1 | Reagent2 | Catalyst | Base | Ligand | Solvent | Amount (yield) HPLC/ ESI-MS |
|---|---|---|---|---|---|---|---|
| $1^{st}$ | A2 2125473-29-0 | 15.3 g 1.0 eq. | 14221- 01-3 2 mol % | 584- 08-7 2.0 eq. | x | THF/$H_2O$ 4/1 | 19.3 g |
| $2^{nd}$ | B1-5 19.1 g | 73183- 34-3 1.1 eq. | 51364- 51-3: 2.5 mol % | 127- 08-2 3.0 eq. | 564483- 18-7 10 mol % | Dioxane | 19.0 g |
| $3^{rd}$ | C1-5 9.5 g | 3430- 31-7 1.1 eq. | 1798781- 99-3 2 mol % | 7778- 53-2 2.0 eq | x 4/145° C. | THF/$H_2O$ | 4.6 g (50%) HPLC/ ESI-MS: 99.6%, m/z 721.3 ([M + H])⁺ |

2,3,5-triphenyl-6-(3-(4,4,5,5-tetramethyl-1,3,2-dioxaborolan-2-yl)phenyl)pyrazine was synthesized from 2-(3-bromophenyl)-3,5,6-triphenylpyrazine, using standard borilation conditions described in WO17135510A1.

2-(3-bromophenyl)-3,5,6-triphenylpyrazine was synthesized in a similar way than 943442-81-7 (Journal of Materials Chemistry C: Materials for Optical and Electronic Devices, 4(14), 2901-2908, 2016)

Synthesis of 2-(3-(3-(4-(2,6-dimethylpyridin-3-yl)phenyl)-5,6-diphenylpyrazin-2-yl)phenyl)-4,6-diphenyl-1,3,5-triazine (Compound 130)
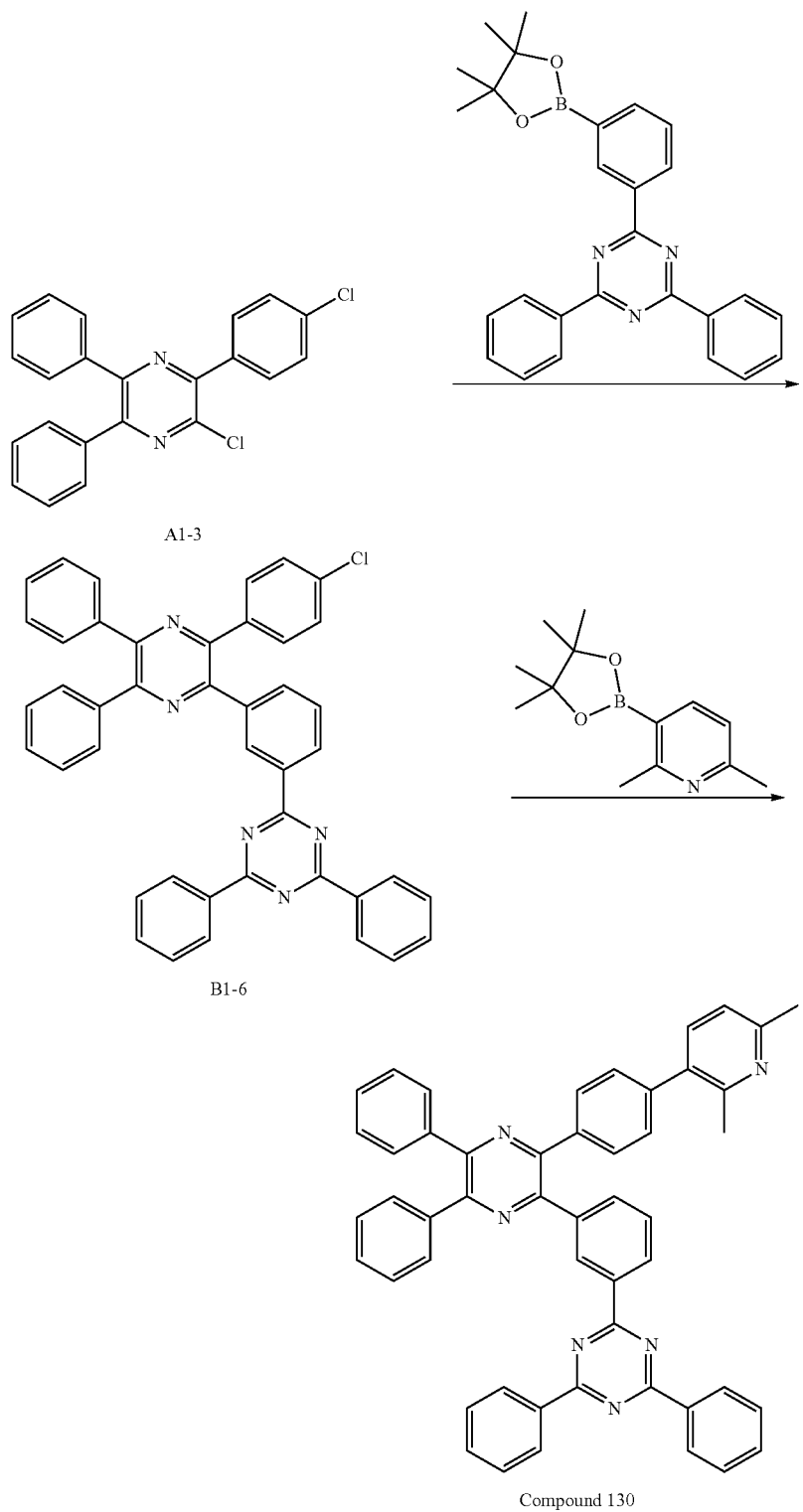
Compound 130 was synthesized according to the general procedure and using reagent given in table below

| | Reagent1 | Reagent2 | Catalyst | Base | Solvent Temp. | Amount (yield) HPLC/ ESI-MS |
|---|---|---|---|---|---|---|
| 1st step | A4: 21.9 g | 1269508-31-7 1.2 eq | 72287-26-4 0.5 mol % | 584-08-7 2.0 eq. | THF/H$_2$O 4/155° C. | 11.3 g |
| 2nd step | B4: 5.0 g | 3430-31-7 1.5 eq | Pd-172 1798781-99-32 mol % | 7778-53-2 2.0 eq | Tol/EtOH/H$_2$O 10/1/545° C. | 3.0 g (55%) HPLC/ ESI-MS: 99.9%, m/z = 721.2 ([M + H])$^+$ |

Synthesis of Compound A1-3

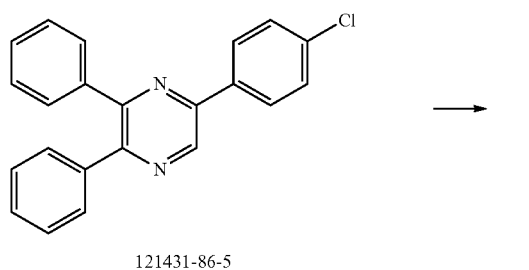

121431-86-5

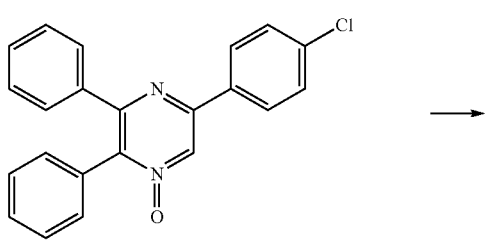

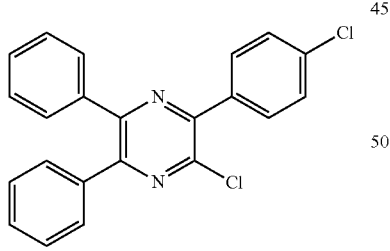

5-(4-chlorophenyl)-2,3-diphenylpyrazine (72.0 g, 207.7 mmol) was suspended in 1,2-dichloroethane (500 mL) and 3-Chloroperbenzoic acid (55.9 g, 249.4 mmol, 77% purity) was added at room temperature. The reaction mixture was then stirred at 65° C. for 4 h. 3-Chloroperbenzoic acid (23.3 g, 103.5 mmol) was added and the reaction was stirred overnight. 3-Chloroperbenzoic acid (23.3 g, 103-5 mmol) was added and the reaction was stirred overnight. Reaction was completed and cooled down to room temperature. Na$_2$S$_2$O$_3$ (aq.) was added and the mixture was stirred for 15 min. Organic phase was decanted and washed with K$_2$CO$_3$ (aq.), NaCl (aq.) and water. The organic phase was dried over Na$_2$SO$_4$ and solvent was removed under reduced pressure. Crude was dissolved in dichloromethane (0.5 L) and concentrated to 150 mL. Petroleum ether was added, and the precipitate was filtered off and washed with a mixture of 10% dichloromethane in petroleum ether (200 ml) and with 5% methanol in petroleum ether to afford 63.0 g of intermediate that was used directly for the next step.

5-(4-chlorophenyl)-2,3-diphenylpyrazine 1-oxide (63.0 g, 173.8 mmol), was refluxed in phosphoryl chloride (370 mL) for 30 min. Phosphoryl chloride was distilled off. The residue was suspended in dichlormethane (300 ml) and was carefully and slowly added to ice-cold K$_2$CO$_3$ (aq.). Then some NaCl(aq) was added and mixture was extracted with dichloromethane. Combined organic phases were washed with brine, dried, concentrated under reduced pressure to 700 mL and filtered through a pad of silicagel using dichloromethane as eluent. Solvent was partially removed under reduced pressure, hot methanol (300 mL) was added and the suspension was stirred at 90° C. without the cooler. Solvent was partially removed under reduced pressure and hot methanol (150 mL) was added. The suspension was stirred at room temperature for 40 min, and then cool down to 0° C. The precipitate was filtered off, washed with cold methanol and finally recrystallized from dichloromethane/petroleum ether to yield 47.72 g (61%) of 2-chloro-3-(4-chlorophenyl)-5,6-diphenylpyrazine.

Synthesis of 2-(2,6-dimethylpyridin-3-yl)-4-phenyl-6-(3-(10-phenylanthracen-9-yl)phenyl)-1,3,5-triazine (Compound 121)

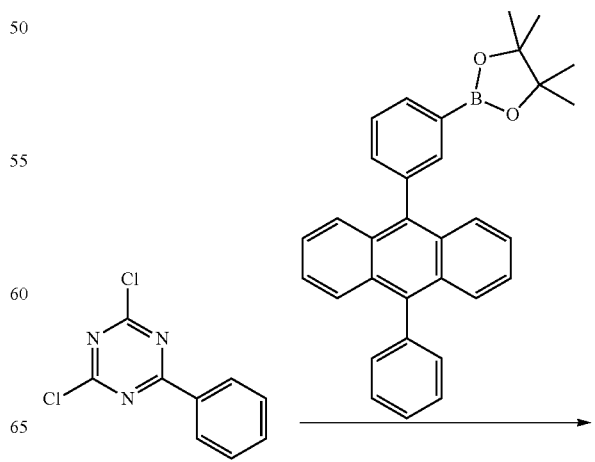

-continued
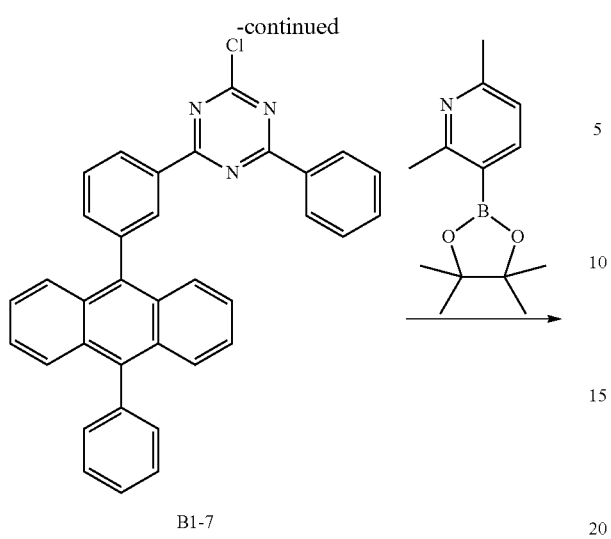
B1-7
Synthesis of 4-(3-(2,6-dimethylpyridin-3-yl)phenyl)-2-phenyl-6-(3-(3,5,6-triphenylpyrazin-2-yl)phenyl)pyrimidine (Compound 174)
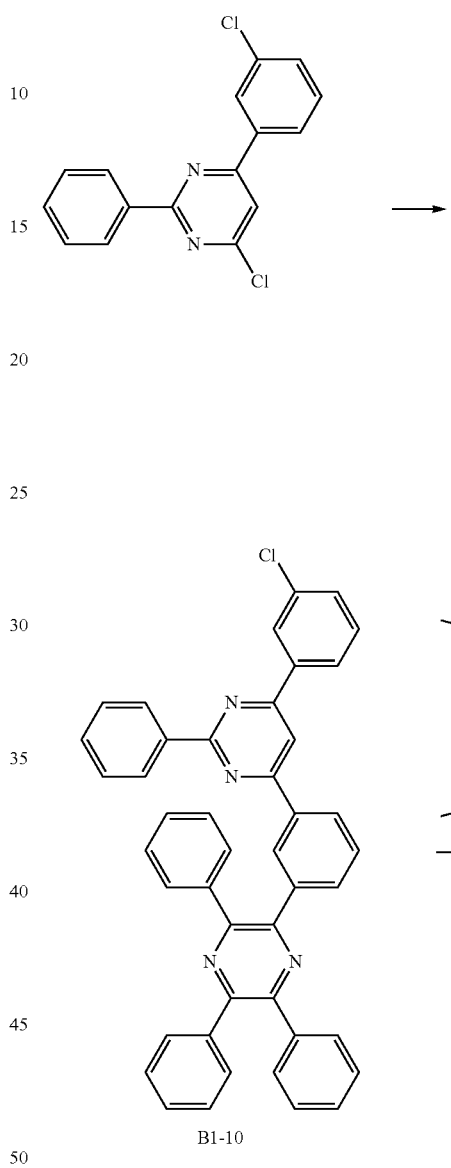
Compound 121
B1-10
| Step | Reagent1 | Reagent2 | Catalyst | Base | Solvent | Amount (yield) HPLC/ ESI-MS |
|---|---|---|---|---|---|---|
| 1st | E1 1700-02-3 100 g | 1023674-81-8 0.8 eq. | 14221-01-3 2 mol % | 584-08-7 2.0 eq. | THF/H₂O 4/1 75° C. | 27.1 g |
| 2nd | B1-7 9.1 g | 693774-10-6 1.5 eq | 1798781-99-3 2 mol % | 7778-53-2 2.0 eq | Tol/EtOH/H₂O 10/1/5 45° C. | 3.5 g (35%) HPLC/ESI-MS: 99.7%, m/z = 591.2 ([M + H]) |

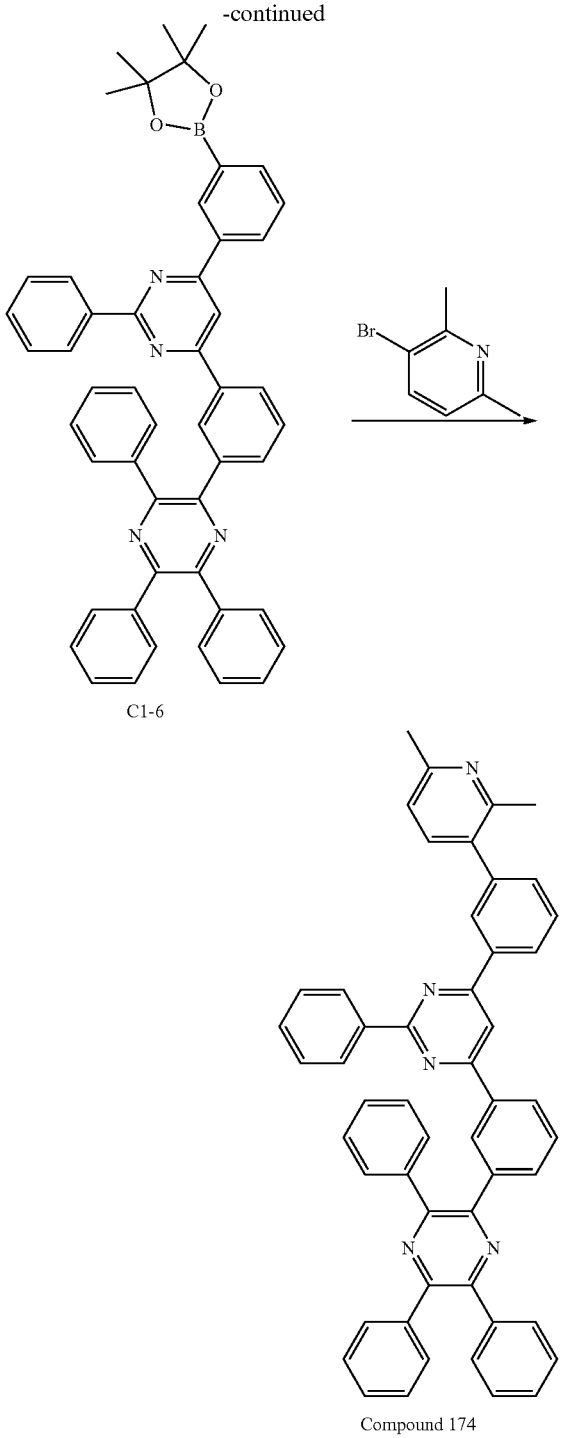

C1-6

Compound 174 atmosphere. After cooling down to room temperature, the resulting precipitate was isolated by suction filtration and washed with water (80 mL), methanol (30 mL) and hexane (30 mL). Then the crude product was additionally thoroughly washed with methanol (100 mL) and dried yielding 16.23 g of (B1-10).

2$^{nd}$ Step

To synthesis 2-phenyl-4-(3-(4,4,5,5-tetramethyl-1,3,2-dioxaborolan-2-yl)phenyl)-6-(3-(3,5,6-triphenylpyrazin-2-yl) phenyl)pyrimidine (C1-6), a flask was flushed with nitrogen and charged with 4-(3-chlorophenyl)-2-phenyl-6-(3-(3,5,6-triphenylpyrazin-2-yl)phenyl)pyrimidine (B1-10) (21.5 g, 33.1 mmol), 4,4,4',4',5,5,5',5'-octamethyl-2,2'-bi(1,3,2-dioxaborolane) (10.93 g, 43 mmol), 2-dicyclohexylphosphino-2',4',6'-triisopropylbiphenyl (0.79 g, 1.66 mmol), tris(dibenzylideneacetone)dipalladium(0) (0.61 g, 0.66 mmol) and potassium acetate (9.74 g, 99.3 mmol). Dry dioxane was added and the reaction mixture was heated 19 h at 100° C. under inert atmosphere. After cooling down to room temperature, the resulting mixture was concentrated under reduced pressure, then mixed with chloroform (400 mL), washed with water (3×80 mL), dried over MgSO$_4$ and filtered through a pad of silica gel/florisil (1:1). The filtrate was concentrated under reduced pressure to yield 20.7 g of (C1-6).

3$^{rd}$ Step

To synthesis 4-(3-(2,6-dimethylpyridin-3-yl)phenyl)-2-phenyl-6-(3-(3,5,6-triphenylpyrazin-2-yl)phenyl)pyrimidine (compound XXX), a flask was flushed with nitrogen and charged with 2-phenyl-4-(3-(4,4,5,5-tetramethyl-1,3,2-dioxaborolan-2-yl)phenyl)-6-(3-(3,5,6-triphenylpyrazin-2-yl)phenyl)pyrimidine (C1-6) (20.7 g, 27.9 mmol), 3-bromo-2,6-dimethylpyridine (6.24 g, 33.5 mmol), chloro(crotyl)(2-dicyclohexylphosphino-2',6'-dimethoxybiphenyl)palladium (II) (0.34 g, 0.56 mmol) and K3PO4 (11.9 g, 56 mmol). Deaerated mixture dioxane/water (8:1, 250 mL) was added and the reaction mixture was heated 20 h at 45° C. under inert atmosphere. After cooling down to room temperature, the resulting precipitate was isolated by suction filtration. The crude product was then dissolved in chloroform (700 mL), washed with water (4×120 mL), dried over MgSO$_4$ and filtered through a pad of silica gel. The filtrate was concentrated under reduced pressure, washed thoroughly with methanol (100 mL) and recrystallized from chlorobenzene to yield 12.7 g of (compound 174). m/z=720.2 ([M+H]$^+$).

Synthesis of 2-(3-(2,6-dimethylpyridin-3-yl)phenyl)-4-(3',5'-diphenyl-[1,1':4',1"-terphenyl]-4-yl)-6-phenyl-1,3,5-triazine (Compound 175)

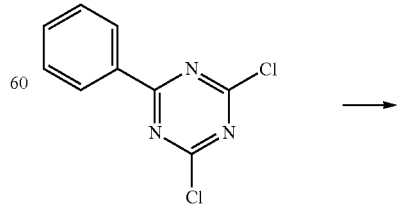

1$^{st}$ Step

To synthesis 4-(3-chlorophenyl)-2-phenyl-6-(3-(3,5,6-triphenylpyrazin-2-yl)phenyl)pyrimidine (B1-10) a flask was flushed with nitrogen and charged with 4-chloro-6-(3-chlorophenyl)-2-phenylpyrimidine (10 g, 33.2 mmol), 2,3,5-triphenyl-6-(3-(4,4,5,5-tetramethyl-1,3,2-dioxaborolan-2-yl)phenyl)pyrazine (16.95 g, 33.2 mmol), [1,1'-bis(diphenylphosphino)ferrocene]dichloropalladium(II) (0.49 g, 0.66 mmol) and K2CO3 (9.16 g, 66.4 mmol). Deaerated mixture dioxane/H2O (4:1, 100 mL) was added and the reaction mixture was heated 22 h at 55° C. under inert

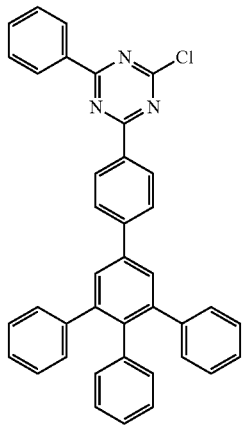

B1-11

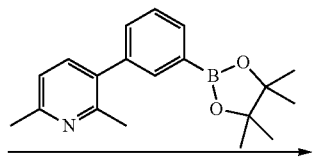

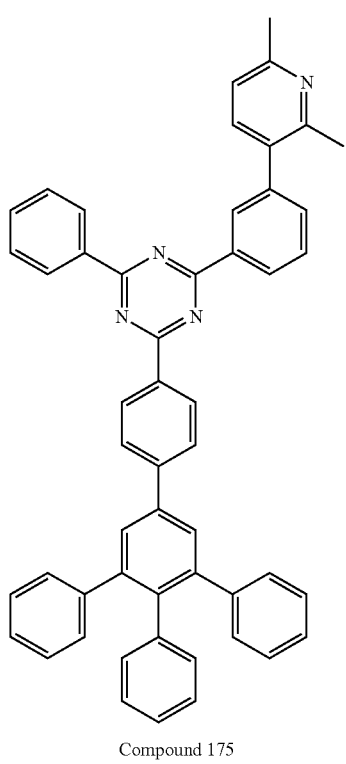

Compound 175

1<sup>st</sup> Step

To synthesis 2-chloro-4-(3',5'-diphenyl-[1,1':4',1''-terphenyl]-4-yl)-6-phenyl-1,3,5-triazine (B1-11), a flask was flushed with nitrogen and charged with 2-(3',5'-diphenyl-[1,1':4',1''-terphenyl]-4-yl)-4,4,5,5-tetramethyl-1,3,2-dioxaborolane (100 g, 196.7 mmol), 2,4-dichloro-6-phenyl-1,3,5-triazine (66.69 g, 295 mmol), K2CO3 (67.91 g, 491.7 mmol) and [1,1'-bis(diphenylphosphino)ferrocene]-dichloropalladium(II) (7.19 g, 9.83 mmol). Deaerated mixture toluene/THF/H2O (1:1:1, 1.2 L) was added and the reaction mixture was heated 5 h at 60° C. under inert atmosphere. After cooling down to room temperature, the resulting precipitate was isolated by suction filtration and washed with water (600 mL), methanol (100 mL) and hexane (100 mL). Then the crude product was additionally thoroughly washed with methanol (600 mL) and dried yielding 102.6 g of (B1-11).

2<sup>nd</sup> Step

To synthesis 2-(3-(2,6-dimethylpyridin-3-yl)phenyl)-4-(3',5'-diphenyl-[1,1':4',1''-terphenyl]-4-yl)-6-phenyl-1,3,5-triazine (compound XXX), a flask was flushed with nitrogen and charged with 2-chloro-4-(3',5'-diphenyl-[1,1':4',1''-terphenyl]-4-yl)-6-phenyl-1,3,5-triazine (B1-11) (20 g, 34.95 mmol), 2,6-dimethyl-3-(3-(4,4,5,5-tetramethyl-1,3,2-dioxaborolan-2-yl)phenyl)pyridine (11.89 g, 38.45 mmol), tetrakis(triphenylphosphin)palladium(0) (0.81 g, 0.7 mmol) and K2CO3 (9.65 g, 69.9 mmol). Deaerated mixture dioxane/H2O (4:1, 170 mL) was added and the reaction mixture was heated 8 h at 90° C. under inert atmosphere. After cooling down to room temperature, the resulting precipitate was isolated by suction filtration and washed with water (100 mL) and methanol (2×30 mL). The crude product was then dissolved in a mixture of DCM (600 mL) and hexane (600 mL), filtered through a pad of silica gel and dried over MgSO4. The filtrate was concentrated under reduced pressure and precipitated from hexane (350 mL) to yield 9.89 g of (compound 175). m/z=719.3 ([M+H]<sup>+</sup>).

Synthesis of 2-(2',6'-diphenyl-[1,1':4',1''-terphenyl]-4-yl)-4-(4-(2-methylpyridin-3-yl)phenyl)-6-phenyl-1,3,5-triazine (Compound 176)

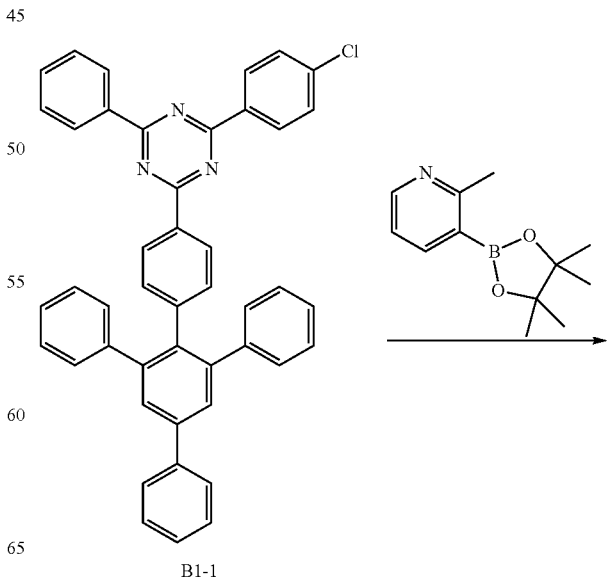

B1-1

-continued

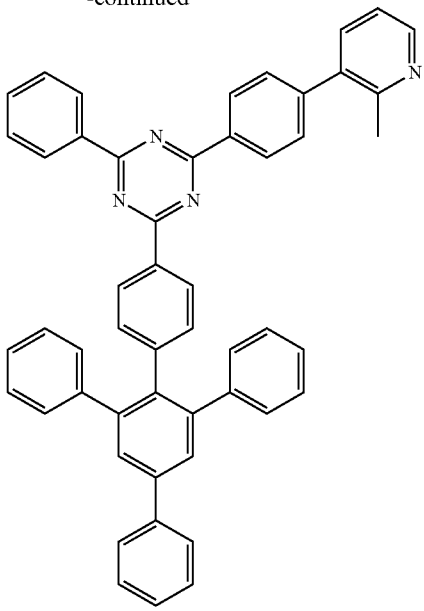

Compound 176

To synthesis 2-(2',6'-diphenyl-[1,1':4',1''-terphenyl]-4-yl)-4-(4-(2-methylpyridin-3-yl)phenyl)-6-phenyl-1,3,5-triazine (compound XXX), a flask was flushed with nitrogen and charged with 2-(4-chlorophenyl)-4-(2',6'-diphenyl-[1,1':4',1''-terphenyl]-4-yl)-6-phenyl-1,3,5-triazine (B1-1) (8.0 g, 12.34 mmol), 2-methyl-3-(4,4,5,5-tetramethyl-1,3,2-dioxaborolan-2-yl)pyridine (4.11 g, 18.76 mmol), chloro(crotyl)(2-dicyclohexylphosphino-2',6'-dimethoxybiphenyl)palladium(II) (0.15 g, 0.24 mmol) and K3PO4 (5.24 g, 24.7 mmol). Deaerated mixture THF/EtOH/H2O (10:1:5, 64 mL) was added and the reaction mixture was refluxed for 20 h under inert atmosphere. After cooling down to room temperature, the resulting precipitate was isolated by suction filtration and washed with water (50 mL) and methanol (200 mL). The crude product was then dissolved in toluene (500 mL), filtered through a pad of silica gel and evaporated under reduced pressure to yield 7.97 g of (compound 176). m/z=705.2 ([M+H]$^+$).

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 µL Mettler Toledo aluminum pan with lid, a <1 mm hole is pierced into the lid).

Glass Transition Temperature

The glass transition temperature (Tg) is measured under nitrogen and using a heating rate of 10 K per min in a Mettler Toledo DSC 822e differential scanning calorimeter as described in DIN EN ISO 11357, published in March 2010.

Reduction Potential

The reduction potential is determined by cyclic voltammetry with potenioststic device Metrohm PGSTAT30 and software Metrohm Autolab GPES at room temperature. The redox potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard Fc$^+$/Fc redox couple, afforded finally the values reported above. All studied compounds as well as the reported comparative compounds showed well-defined reversible electrochemical behaviour.

Dipole Moment

The dipole moment $|\vec{\mu}|$ of a molecule containing N atoms is given by:

$$\vec{\mu} = \sum_i^N q_i \vec{r_i}$$

$$|\vec{\mu}| = \sqrt{\mu_x^2 + \mu_y^2 + \mu_z^2}$$

where $q_i$ and $\vec{r_i}$ are the partial charge and position of atom i in the molecule.

The dipole moment is determined by a semi-empirical molecular orbital method.

The geometries of the molecular structures are optimized using the hybrid functional B3LYP with the 6-31G* basis set in the gas phase as implemented in the program package TURBOMOLE V6.5. If more than one conformation is viable, the conformation with the lowest total energy is selected to determine the bond lengths of the molecules.

Calculated HOMO and LUMO

The HOMO and LUMO are calculated with the program package TURBOMOLE V6.5. The optimized geometries and the HOMO and LUMO energy levels of the molecular structures are determined by applying the hybrid functional B3LYP with a 6-31G* basis set in the gas phase. If more than one conformation is viable, the conformation with the lowest total energy is selected.

General Procedure for Fabrication of OLEDs

For top emission devices, example 1 to example 5 and comparative example 1 in Table 2, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes. 100 nm Ag were deposited on the glass substrate at a pressure of 10-5 to 10-7 mbar to form the anode.

Then, 92 vol.-% N-([1,1'-biphenyl]-4-yl)-9,9-dimethyl-N-(4-(9-phenyl-9-carbazol-3-yl)phenyl)-9H-fluoren-2-amine (CAS 1242056-42-3) with 8 vol.-% 2,2',2''-(cyclopropane-1,2,3-triylidene)tris(2-(p-cyanotetrafluorophenyl)acetonitrile) was vacuum deposited on the anode, to form a HIL having a thickness of 10 nm. Then, N-([1,1'-biphenyl]-4-yl)-9,9-dimethyl-N-(4-(9-phenyl-9H-carbazol-3-yl)phenyl)-9H-fluoren-2-amine was vacuum deposited on the HIL, to form a HTL having a thickness of 128 nm.

Then, N,N-bis(4-(dibenzo[b,d]furan-4-yl)phenyl)-[1,1':4',1''-terphenyl]-4-amine (CAS 1198399-61-9) was vacuum deposited on the HTL, to form an electron blocking layer (EBL) having a thickness of 5 nm.

Then, 97 vol.-% H09 (Sun Fine Chemicals) as EML host and 3 vol.-% BD200 (Sun Fine Chemicals) as fluorescent blue dopant were deposited on the EBL, to form a blue-emitting EML with a thickness of 20 nm.

Then the auxiliary electron transport layer (ETL-1) was formed with a thickness of 5 nm by depositing 2-(3'-(9,9-dimethyl-9H-fluoren-2-yl)-[1,1'-biphenyl]-3-yl)-4,6-diphenyl-1,3,5-triazineon the emission layer (EML).

Then, the electron transporting layer 2 (ETL-2) was formed on the auxiliary electron transport layer (ETL-1) by depositing the compound of Formula (I) according to the inventive example 1 to example 5 and comparative compound 1 according to the comparative example 1 with a the thickness of 31 nm. The electron transport layer 2 (ETL-2) comprises 50 wt.-% matrix compound and 50 wt.-% of LiQ, see Table 2.

Then, the electron injection layer was formed on the electron transporting layer 2 by deposing Yb with a thickness of 2 nm.

Ag:Mg (90:10) was co-deposited at a rate of 0.01 to 1 Å/s at 10-7 mbar to form a cathode with a thickness of 13 nm.

The OLED stack is protected from ambient conditions by encapsulation of the device with a glass slide. Thereby, a cavity is formed, which includes a getter material for further protection.

To assess the performance of the inventive examples compared to the prior art, the current efficiency is measured at 20° C. The current-voltage characteristic is determined using a Keithley 2635 source measure unit, by sourcing a voltage in V and measuring the current in mA flowing through the device under test. The voltage applied to the device is varied in steps of 0.1V in the range between 0V and 10V. Likewise, the luminance-voltage characteristics and CIE coordinates are determined by measuring the luminance in cd/m$^2$ using an Instrument Systems CAS-140CT array spectrometer for each of the voltage values. The cd/A efficiency at 10 mA/cm2 is determined by interpolating the luminance-voltage and current-voltage characteristics, respectively.

Lifetime LT of the device is measured at ambient conditions (20° C.) and 30 mA/cm$^2$, using a Keithley 2400 sourcemeter, and recorded in hours.

The brightness of the device is measured using a calibrated photo diode. The lifetime LT is defined as the time till the brightness of the device is reduced to 97% of its initial value.

The light output in external efficiency EQE and power efficiency (lm/W efficiency) are determined at 10 mA/cm2 for top emission devices.

To determine the efficiency EQE in % the light output of the device is measured using a calibrated photodiode.

To determine the power efficiency in lm/W, in a first step the luminance in candela per square meter (cd/m2) is measured with an array spectrometer CAS140 CT from Instrument Systems which has been calibrated by Deutsche Akkreditierungs-stelle (DAkkS). In a second step, the luminance is then multiplied by π and divided by the voltage and current density.

Technical Effect of the Invention

The OLED device comprising electron transport layer 2 comprising compound of formula 1 showed an improved efficiency (cd/A at 10 mA/cm$^2$) as compared to the OLED device with electron transport layer 2 comprising comparative compound 1 with a comparable OLED performance parameters e.g. low voltage.

TABLE 1

| Referred to as: | Structure | mp (° C.) | Tg (° C.) | T$_{RO}$ (° C.) | HOMO (eV) | LUMO (eV) | Diplole moment (Debye) |
|---|---|---|---|---|---|---|---|
| Comparative compound 1 | 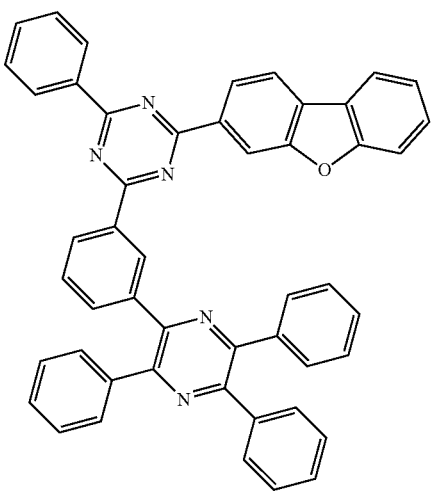 [SMILES: c1ccc(-c2nc(-c3cccc(-c4nc(-c5ccccc5)c(-c5ccccc5)nc4-c4ccccc4)c3)nc(-c3ccc4c(c3)oc3ccccc34)n2)cc1] | 295 | 136 | 258 | −5.77 | −1.97 | 1.07 |

TABLE 1-continued
Properties of the compounds of formula 1
| Referred to as: | Structure | mp (° C.) | Tg (° C.) | T$_{RO}$ (° C.) | HOMO (eV) | LUMO (eV) | Diplole moment (Debye) |
|---|---|---|---|---|---|---|---|
| Compound 1 | 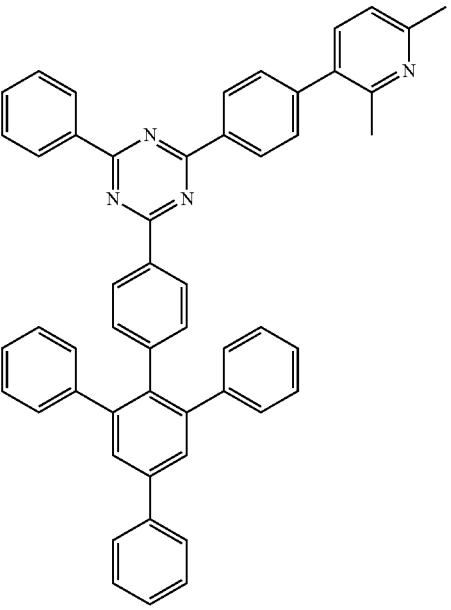 [SMILES: Cc1ccc(-c2ccc(-c3nc(-c4ccccc4)nc(-c4ccc(-c5c(-c6ccccc6)cc(-c6ccccc6)cc5-c5ccccc5)cc4)n3)cc2)c(C)n1] | 329 | 148 | 268 | −5.83 | −1.88 | 1.39 |
| Compound 2 | 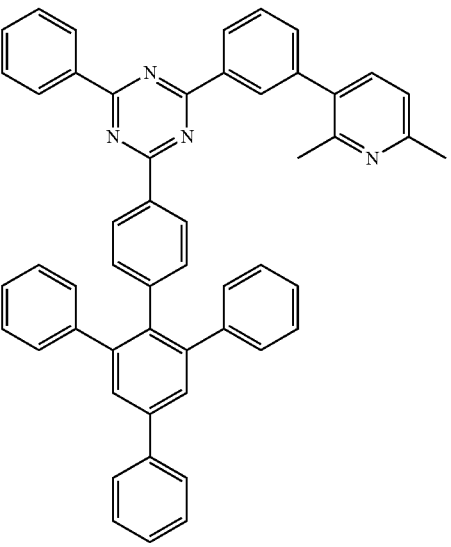 [SMILES: Cc1ccc(-c2cccc(-c3nc(-c4ccccc4)nc(-c4ccc(-c5c(-c6ccccc6)cc(-c6ccccc6)cc5-c5ccccc5)cc4)n3)c2)c(C)n1] | 271 | — | 252 | −5.82 | −1.85 | 1.21 |

TABLE 1-continued
Properties of the compounds of formula 1
| Referred to as: | Structure | mp (° C.) | Tg (° C.) | $T_{RO}$ (° C.) | HOMO (eV) | LUMO (eV) | Diplole moment (Debye) |
|---|---|---|---|---|---|---|---|
| Compound 119 | 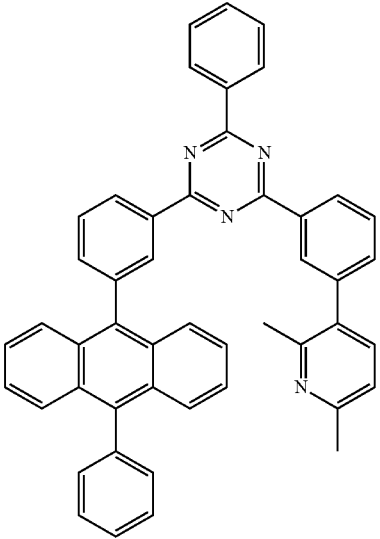 [SMILES: Cc1ccc(-c2cccc(-c3nc(-c4ccccc4)nc(-c4cccc(-c5c6ccccc6c(-c6ccccc6)c6ccccc56)c4)n3)c2)c(C)n1] | — | 135 | — | −5.13 | −1.88 | 1.76 |
| Compound 121 | 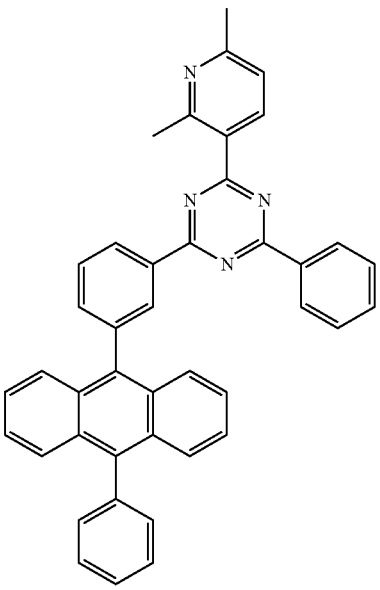 [SMILES: Cc1ccc(-c2nc(-c3ccccc3)nc(-c3cccc(-c4c5ccccc5c(-c5ccccc5)c5ccccc45)c3)n2)c(C)n1] | 255 | 121 | 216 | −5.10 | −1.92 | 1.22 |

TABLE 1-continued
Properties of the compounds of formula 1
| Referred to as: | Structure | mp (° C.) | Tg (° C.) | $T_{RO}$ (° C.) | HOMO (eV) | LUMO (eV) | Diplole moment (Debye) |
|---|---|---|---|---|---|---|---|
| Compound 125 | 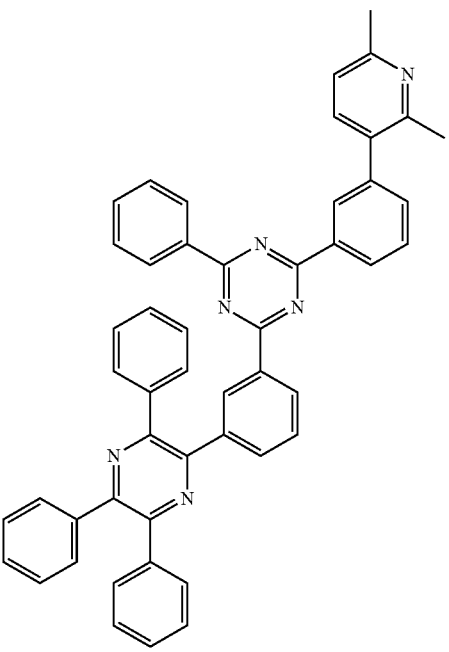 [SMILES: Cc1ccc(-c2cccc(-c3nc(-c4ccccc4)nc(-c4cccc(-c5nc(-c6ccccc6)c(-c6ccccc6)nc5-c5ccccc5)c4)n3)c2)c(C)n1] | — | 117 | 254 | −5.82 | −1.85 | 1.80 |
| Compound 130 | 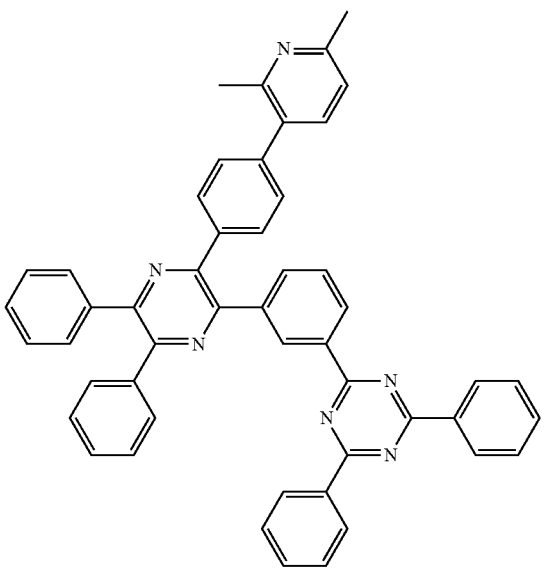 [SMILES: Cc1ccc(-c2ccc(-c3nc(-c4ccccc4)c(-c4ccccc4)nc3-c3cccc(-c4nc(-c5ccccc5)nc(-c5ccccc5)n4)c3)cc2)c(C)n1] | 242 | 126 | 242 | −5.63 | −1.87 | 1.53 |

TABLE 1-continued

Properties of the compounds of formula 1

| Referred to as: | Structure | mp (° C.) | Tg (° C.) | T$_{RO}$ (° C.) | HOMO (eV) | LUMO (eV) | Diploe moment (Debye) |
|---|---|---|---|---|---|---|---|
| Compound 174 | | 248 | 116 | 246 | −5.82 | −1.70 | 2.95 |
| Compound 175 | | — | 122 | 249 | −5.81 | −1.93 | 1.04 |

TABLE 1-continued

Properties of the compounds of formula 1

| Referred to as: | Structure | mp (° C.) | Tg (° C.) | $T_{RO}$ (° C.) | HOMO (eV) | LUMO (eV) | Diplole moment (Debye) |
|---|---|---|---|---|---|---|---|
| Compound 176 | 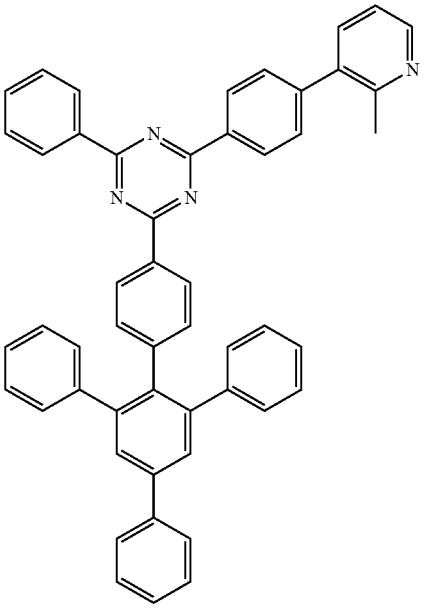 [SMILES: Cc1ncccc1-c1ccc(-c2nc(-c3ccccc3)nc(-c3ccc(-c4c(-c5ccccc5)cc(-c5ccccc5)cc4-c4ccccc4)cc3)n2)cc1] | 325 | 149 | 279 | −5.84 | −1.92 | 1.94 |

TABLE 2

Performance of an organic electroluminescent device comprising an electron transport layer 2 comprising a compound of formula 1

| Example | Matrix compound | Concentration of matrix compound in ETL 2 (vol.-%) | Alkali organic complex | Concentration of alkali organic complex (vol.-%) | Thickness electron transport layer 2 (nm) | Operating voltage at 10 mA/cm² (V) | cd/A efficiency at 10 mA/cm² (cd/A) |
|---|---|---|---|---|---|---|---|
| example 1 (Comparative) | | 50 | LiQ | 50 | 31 | 3.6 | 7.4 |
| Example 1 | 1 | 50 | LiQ | 50 | 31 | 3.5 | 7.9 |
| Example 2 | 125 | 50 | LiQ | 50 | 31 | 3.5 | 7.9 |
| Example 3 | 130 | 50 | LiQ | 50 | 31 | 3.5 | 7.9 |
| Example 4 | 119 | 50 | LiQ | 50 | 31 | 3.5 | 7.7 |
| Example 5 | 2 | 50 | LIQ | 50 | 31 | 3.5 | 7.6 |

Table 2 shows that the OLED device with electron transport layer 2 comprising compound of formula 1 showed improved efficiency (cd/A at 10 mA/cm²) as compared to the OLED device with electron transport layer 2 comprising comparative compound 1.

The features disclosed in the foregoing description and in the dependent claims may, both separately and in any combination thereof, be material for realizing the aspects of the disclosure made in the independent claims, in diverse forms thereof.

The invention claimed is:

1. Compound represented by the following Formula (I)

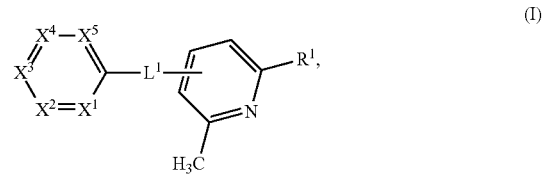

(I)

wherein
R¹ is selected from the group consisting of H, CH₃, ethyl, n-propyl, iso-propyl, n-butyl, sec-butyl, iso-butyl and tert-butyl;
L¹ represents a direct bond or is $C_6$ to $C_{18}$ arylene;
X¹ to X⁵ are independently selected from the group consisting of CR² and N, wherein 2 to 4 of X¹ to X⁵ are N and 1 to 3 of X¹ to X⁵ are independently selected CR²;
R² is independently selected from the group consisting of H, substituted or unsubstituted $C_6$ to $C_{36}$ aryl, substituted or unsubstituted $C_3$ to $C_{36}$ heteroaryl, and a group represented by the following Formula (II)

$$*-L^2-Ar^1 \quad (II)$$

wherein the asterisk symbol "*" represents the binding position of the structure according to Formula II to the C-atom in the respective group CR²;
two adjacent R² can be linked together to form a ring;
the one or more substituent(s), if present in one or more of the groups R² are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$; wherein Y is O or S, and R³ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl, and $C_3$-$C_{20}$ heteroaryl;
at least one of R² is represented by the Formula (II);
in Formula (II) L² represents a direct bond or is a substituted or unsubstituted $C_6$ to $C_{24}$ arylene group or a substituted or unsubstituted $C_3$ to $C_{20}$ heteroarylene;
Ar¹ is selected from the group consisting of

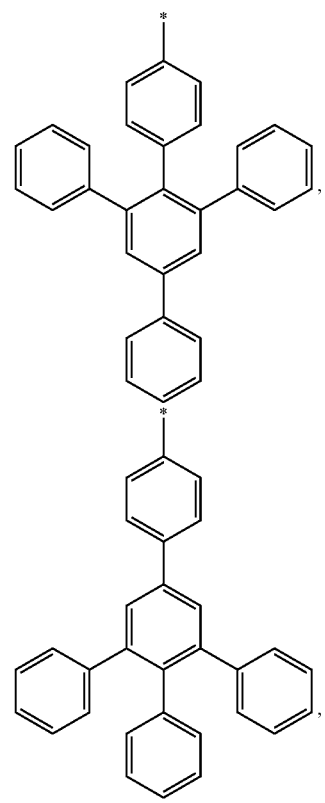

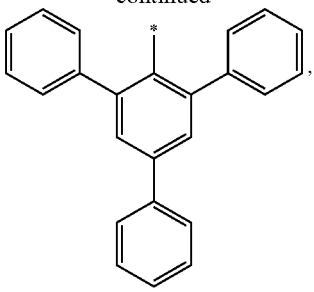

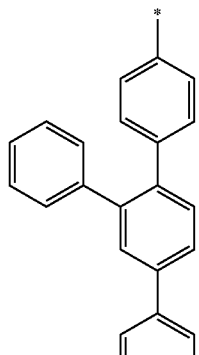

, and 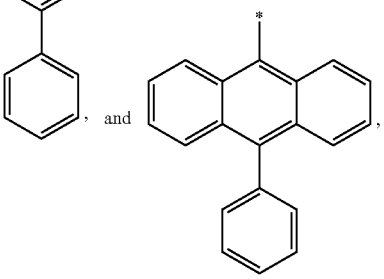

wherein the one or more substituent(s), if present in L², are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$, wherein Y is O or S, and R³ are independently selected from the group consisting of $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl.

2. Compound according to claim 1, wherein the compound of formula (I) is represented by one of the following formulas (III) to (IX)

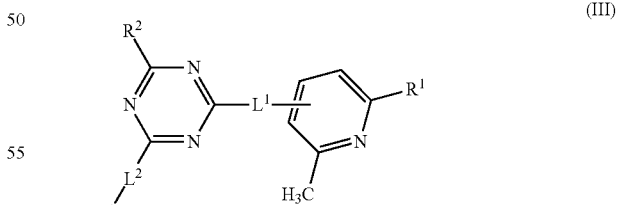

(III)

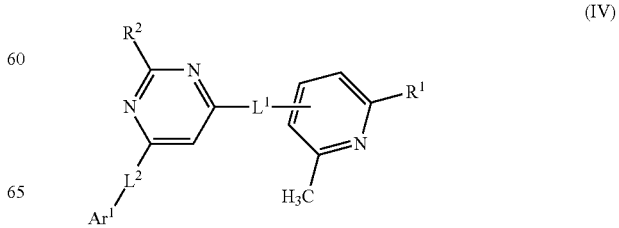

(IV)

quinoxalinyl, quinolinyl, and the group represented by the Formula (II)

$$*\text{-}L^2\text{-}Ar^1 \quad (II),$$

wherein the respective groups may independently be substituted or unsubstituted, wherein the one or more substituent(s), if present in one or more of the groups $R^2$, are independently selected from the group consisting of D, F, CN, $C_1$ to $C_{16}$ alkyl, $C_1$ to $C_{16}$ alkoxy, $C_6$ to $C_{24}$ aryl, $C_3$ to $C_{20}$ heteroaryl, nitrile, and $PY(R^3)_2$, wherein Y is O or S, and $R^3$ are independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl.

8. Compound according to claim 1, wherein $L^2$ represents a direct bond or is selected from the group consisting of phenylene, biphenylene, triphenylene, naphthylene, dibenzofurene, dibenzothiophene, carbazolene, pyridine, phenylpyridine, quinoline.

9. Compound according to claim 1, wherein the compound of formula (I) is represented by one of the following formulas (I-a) or (I-b) or (I-c) or (I-d)

3. Compound according to claim 1, wherein $R^1$ is H or $CH_3$.

4. Compound according to claim 1, wherein $L^1$ represents a single bond or is selected from the group consisting of phenylene, biphenylene, triphenylene, and naphthylene.

5. Compound according to claim 1, wherein $L^1$ represents a direct bond or is phenylene.

6. Compound according to claim 1, wherein two or three of $X^1$ to $X^5$ are N.

7. Compound according to claim 1, wherein $R^2$ is independently selected from the group consisting of phenyl, biphenyl, terphenyl, phenantherenyl, benzophenantherenyl, naphthyl, fluorenyl, dimethyl fluorenyl, diphenylfluorenyl, 9,9'-spirobi[fluorene], pyrenyl, crysenyl, fluoranthenyl, tetraphenylethenyl, nitrile, spiro[fluorene-9,9'-xanthene], benzothiophenyl, dibenzofuranyl, carbazolyl, benzothiphenyl, benzofuranyl, benzooxazolyl, benzothiazolyl, quinazolinyl, 10. Organic semiconducting layer comprising the compound of Formula (I) according to claim 1.

11. Organic semiconducting layer according to claim 10, wherein the organic semiconducting layer further comprises a metal, a metal salt or an organic metal complex.

12. Organic electronic device comprising the organic semiconducting layer according to claim 11.

13. Organic electronic device according to claim 12, wherein the organic electronic device further comprises an anode, a cathode and an emission layer, wherein the emission layer is arranged between the anode and the cathode and the organic semiconducting layer is arranged between the emission layer and the cathode.

14. Organic electronic device according to claim 11, wherein the organic semiconducting layer is an electron transport layer.

* * * * *